US009630994B2

(12) United States Patent
Baker et al.

(10) Patent No.: US 9,630,994 B2
(45) Date of Patent: Apr. 25, 2017

(54) POLYPEPTIDES FOR USE IN SELF-ASSEMBLING PROTEIN NANOSTRUCTURES

(71) Applicant: UNIVERSITY OF WASHINGTON, Seattle, WA (US)

(72) Inventors: David Baker, Seattle, WA (US); Jacob B. Bale, Seattle, WA (US); Neil P. King, Seattle, WA (US); William H. Sheffler, Seattle, WA (US); Daniel Ellis, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 14/930,792

(22) Filed: Nov. 3, 2015

(65) Prior Publication Data

US 2016/0122392 A1    May 5, 2016

Related U.S. Application Data

(60) Provisional application No. 62/074,167, filed on Nov. 3, 2014.

(51) Int. Cl.
*A61K 38/16*    (2006.01)
*C07K 14/00*    (2006.01)

(52) U.S. Cl.
CPC ................................. *C07K 14/00* (2013.01)

(58) Field of Classification Search
None
See application file for complete search history.

(56) References Cited

U.S. PATENT DOCUMENTS

| 6,929,933 | B1 * | 8/2005 | Revuelta Doval | ....... | C12N 9/00 435/119 |
| 8,969,521 | B2 | 3/2015 | Baker et al. | | |
| 2011/0200560 | A1 | 8/2011 | Zhang | | |
| 2015/0356240 | A1 | 12/2015 | Baker et al. | | |

FOREIGN PATENT DOCUMENTS

| EP | 1010760 | * | 6/2000 |
| WO | 2006033679 | A2 | 3/2006 |
| WO | 2010019725 | A2 | 2/2010 |
| WO | 2010035009 | A1 | 4/2010 |
| WO | 2011019585 | A1 | 2/2011 |
| WO | 2013056122 | A1 | 4/2013 |
| WO | 2014124301 | A1 | 8/2014 |
| WO | 2016138525 | A1 | 9/2016 |

OTHER PUBLICATIONS

Website: http://www.genisphere.com/, 1 page retreived on Sep. 12, 2016.*
AfosrApan, "Computational design of self- and co-assembling protein nanomaterials with atomic level accuracy" available online at: https://community.apan.org/afosr/w/researchareas/7659.human-performance-and-biosystems.aspx, 2014.
Andersen, et al., "Self-assembly of a nanoscale DNA box with a controllable lid," Nature, vol. 459, No. 7243, pp. 73-76, 2009.
Apolonia, et al., "Promiscuous RNA binding ensures effective encapsidation of APOBEC3 proteins by HIV-1," PLoS Pathogens, vol. 11, No. 1, e1004609, 2015.
Bagby, et al., "[2]—Optimization of Protein Solubility and Stability for Protein Nuclear Magnetic Resonance," Methods in Enzymology, vol. 339, pp. 20-41, 2001.
Ballister, et al., "In vitro self-assembly of tailorable nanotubes from a simple protein building block," Proceedings of the National Academy of Sciences USA, vol. 105, No. 10, pp. 3733-3738, 2008.
Bieniasz, "Late budding domains and host proteins in enveloped virus release," Virology, vol. 344, No. 1, pp. 55-63, 2006.
Biswas, et al., "The human immunodeficiency virus type 1 ribosomal frameshifting site is an invariant sequence determinant and an important target for antiviral therapy," Journal of Virology, vol. 78, No. 4, pp. 2082-2087, 2004.
Blanc, et al., "Refinement of severely incomplete structures with maximum likelihood in BUSTER-TNT," Acta Carystallographica, Section D: Biological Crystallography, vol. 60, Pt 12, Pt 1, pp. 2210-2221, 2004.
Bondos, et al., "Detection and Prevention of Protein Aggregation Before, During, and After Purification," Analytical Biochemistry, vol. 316, No. 2, pp. 223-231, 2003.
Bridgeman, et al., "Viruses transfer the antiviral second messenger cGAMP between cells," Science, vol. 349, No. 6253, pp. 1228-1232, 2015.
Cavrois, et al., "A sensitive and specific enzyme-based-assay detecting HIV-1 virion fusion in primary T lymphocytes," Nature Biotechnology, vol. 20, No. 11, pp. 1151-1154, 2002.
Chao, et al., "Isolating and Engineering Human Antibodies Using Yeast Surface Display," Nature Protocols, vol. 1, No. 2, pp. 755-768, 2016.
Chao, et al., "Structural basis for the coevolution of a viral RNA-protein complex," Nature Structural & Molecular Biology, vol. 15, No. 1, pp. 103-105, 2008.
Colovos, et al., "Verification of protein structures: patterns of nonbonded atomic interactions," Protein Science, vol. 2, No. 9, pp. 1511-1519, 1993.
Cooper, et al., "Predicting protein structures with a multiplayer online game," Nature, vol. 466, No. 7307, pp. 756-760, 2010.
Crowley, et al., "Structural insight into the mechanisms of transport across the *Salmonella enterica* Pdu microcompartment shell," Journal of Biological Chemistry, vol. 285, No. 48, pp. 37838-37846, 2010.
Das, et al., "Simultaneous prediction of protein folding and docking at high resolution," Proceedings of the National Academy of Sciences USA, vol. 106, No. 45, pp. 18978-18983, 2009.
De Guzman, et al., "Structure of the HIV-1 nucleocapsid protein bound to the SL3 psi-RNA recognition element," Science, vol. 279, No. 5349, pp. 384-388, 1998.
DiMaio, et al., "Modeling symmetric macromolecular structures in Rosetta3," PLoS One, vol. 6, No. 6, e20450, pp. 1-13, 2011.

(Continued)

*Primary Examiner* — Satyanarayana R Gudibande
(74) *Attorney, Agent, or Firm* — McDonnell Boehnen Hulbert & Berghoff LLP

(57) ABSTRACT

Synthetic nanostructures, polypeptides that are useful, for example, in making synthetic nanostructures, and methods for using such synthetic nanostructures are disclosed herein.

17 Claims, 7 Drawing Sheets

(56) References Cited

OTHER PUBLICATIONS

Douglas, et al., "Viruses: making friends with old foes," Science, vol. 312, No. 5775, pp. 873-875, 2006.
Emsley, et al., "Features and development of Coot," Acta Crystallographica, Section D: Biological Crystallography, vol. 66, Pt 4, pp. 486-501, 2010.
Fleishman, et al., "Community-wide assessment of protein-interface modeling suggests improvements to design methodology," Journal of Molecular Biology, vol. 414, No. 2, pp. 289-302, 2011.
Fleishman, et al., "Computational design of proteins targeting the conserved stem region of influenza hemagglutinin," Science, vol. 332, No. 6031, pp. 816-821, 2011.
Fleishman, et al., "Hotspot-centric de novo design of protein binders," Journal of Molecular Biology, vol. 413, No. 5, pp. 1047-1062, 2011.
Fleishman, et al., "Restricted sidechain plasticity in the structures of native proteins and complexes," Protein Science, vol. 20, No. 4, pp. 753-757, 2011.
Freed, et al., "Single amino acid changes in the human immunodeficiency virus type 1 matrix block virus particle production," Journal of Virology, vol. 68, No. 8, pp. 5311-5320, 1994.
Gentili, et al., "Transmission of innate immune signaling by packaging of cGAMP in viral particles," Science, vol. 349, No. 6253, pp. 1232-1236, 2015.
Golovanov, et al., "A Simple Method for Improving Protein Solubility and Long-Term Stability," Journal of the American Chemical Society, vol. 126, No. 29, pp. 8933-8939, 2004.
Gosser, et al., "Peptide-triggered conformational switch in HIV-1 RRE RNA complexes," Nature Structural Biology, vol. 8, No. 2, pp. 146-150, 2001.
Gray et al., "Cutting Edge: cGAS is Required for Lethal Autoimmune Disease in the Trex1-Deficient Mouse Model of Aicardi-Goutiéres Syndrome," Journal of Immunology, vol. 195, No. 5, pp. 1939-1943, 2015.
Gribbon, et al., "MagicWand: a single, designed peptide that assembles to stable, ordered alpha-helical fibers," Biochemistry, vol. 47, No. 39, pp. 10365-10371, 2008.
Griffiths, et al., "Cloning, isolation and characterization of the Thermotoga maritima KDPG aldolase," Bioorganic & Medicinal Chemistry, vol. 10, No. 3, pp. 545-550, 2002.
Grigorieff, "FREALIGN: high-resolution refinement of single particle structures," Journal of Structural Biology, vol. 157, No. 1, pp. 117-125, 2007.
Grigoryan, et al., "Computational design of virus-like protein assemblies on carbon nanotube surfaces," Science, vol. 332, No. 6033, pp. 1071-1076, 2011.
Grueninger, et al., "Designed protein-protein association," Science, vol. 319, No. 5860, pp. 206-209, 2008.
Harbury, et al., "High-resolution protein design with backbone freedom," Science, vol. 282, No. 5393, pp. 1462-1467, 1998.
Huang, et al., "A de novo designed protein protein interface," Protein Science, vol. 16, No. 12, pp. 2770-2774, 2007.
Hurley, et al., "Membrane Budding and Scission by the ESCRT Machinery: It's All in the Neck," Nature Reviews Molecular Cell Biology, vol. 11, No. 8, pp. 556-566, 2010.
Ishikawa, et al., "STING is an endoplasmic reticulum adaptor that facilitates innate immune signalling," Nature, vol. 455, No. 7213, pp. 674-678, 2008.
Jacak, et al., "Computational Protein Design with Explicit Consideration of Surface Hydrophobic Patches," Proteins: Structure, Function, and Bioinformatics, vol. 80, No. 3, pp. 825-838, 2012.
Jäckel, et al., "Consensus Protein Design Without Phylogenetic Bias," Journal of Molecular Biology, vol. 399, No. 4, pp. 541-546, 2010.
Janin, et al., "Protein-protein interaction and quaternary structure," Quarterly Reviews of Biophysics, vol. 41, No. 2, pp. 133-180, 2008.
Jha, et al., "Computational design of a PAK1 binding protein," Journal of Molecular Biology, vol. 400, No. 2, pp. 257-270, 2010.
Julien, et al., "Crystal structure of a soluble cleaved HIV-1 envelope trimer," Science, vol. 342, No. 6165, pp. 1477-1483, 2013.
Kabsch, "XDS," Acta Crystallographica, Section D: Biological Crystallography, vol. 66, Pt 2, pp. 125-132, 2010.
Karanicolas, et al., "A de novo protein binding pair by computational design and directed evolution," Molecular Cell, vol. 42, No. 2, pp. 250-260, 2011.
King, et al., "Accurate design of co-assembling multi-component protein nanomaterials," Nature, vol. 510, No. 7503, pp. 103-108, 2014.
King, et al., "Computational design of self-assembling protein nanomaterials with atomic level accuracy," Science, vol. 336, No. 6085, pp. 1171-1174, 2012.
Koder, et al., "Design and engineering of an O(2) transport protein," Nature, vol. 458, No. 7236, pp. 305-309, 2009.
Kortemme, et al., "Computational redesign of protein-protein interaction specificity," Nature Structural & Molecular Biology, vol. 11, No. 4, pp. 371-379, 2004.
Kremer, et al., "Computer visualization of three-dimensional image data using IMOD," Journal of Structural Biology, vol. 116, No. 1, pp. 71-76, 1996.
Krissinel, et al., "Inference of macromolecular assemblies from crystalline state," Journal of Molecular Biology, vol. 372, No. 3, pp. 774-797, 2007.
Kuhlman, et al., "Native protein sequences are close to optimal for their structures," Proceedings of the National Academy of Sciences USA, vol. 97, No. 19, pp. 10383-10388, 2000.
Kumar, et al., "Crystal structure analysis of icosahedral lumazine synthase from *Salmonella typhimurium*, an antibacterial drug target," Acta Crystallographica, Section D: Biological Crystallography, vol. 67, Pt 2, pp. 131-139, 2011.
Lai, et al., "Principles for designing ordered protein assemblies," Trends in Cell Biology, vol. 22, No. 12, pp. 653-661, 2012.
Lai, et al., "Structure of a 16-nm Cage Designed by Using Protein Oligomers," Science, vol. 336, No. 6085, pp. 1129, 2012.
Lanci, et al., "Computational design of a protein crystal," Proceedings of the National Academy of Sciences USA, vol. 109, No. 19, pp. 7304-7309, 2012.
Laskowski, et al., "PROCHECK: a program to check the stereochemical quality of protein structures," Journal of Applied Crystallography, 26:283-291, 1993.
Lawrence, et al., "Shape complementarity at protein/protein interfaces," Journal of Molecular Biology, vol. 234, No. 4, pp. 946-950 1993.
Lemmon, "Membrane recognition by phospholipid-binding domains." Nature Reviews Molecular Cell Biology, vol. 9, No. 2, pp. 99-111, 2008.
Levy, et al., "3D complex: a structural classification of protein complexes," PLoS Computational Biology, vol. 2, No. 11, e155, pp. 1395-1406, 2006.
Lovejoy, et al., "Crystal structure of a synthetic triple-stranded alpha-helical bundle," Science, vol. 259, No. 5099, pp. 1288-1293, 1993.
Ludtke et al., "EMAN: semiautomated software for high-resolution single-particle reconstructions," Journal of Structural Biology, vol. 128, No. 1, pp. 82-97, 1999.
Lüthy, et al., "Assessment of protein models with three-dimensional profiles," Nature, vol. 356, No. 6364, pp. 83-85, 1992.
Lyumkis, et al., "Cryo-EM structure of a fully glycosylated soluble cleaved HIV-1 envelope timer," Science, vol. 342, No. 6165, pp. 1484-1490, 2013.
Mangeot, et al., "Protein transfer into human cells by VSV-G-induced nanovesicles," Molecular Therapy, vol. 19, No. 9, pp. 1656-1666, 2011.
McCoy, et al., "Phaser crystallographic software," Journal of Applied Crystallography, vol. 40, Pt 4, pp. 658-674, 2007.
McCullough, et al., "Membrane Fission Reactions of the Mammalian ESCRT Pathway," Annual Review of Biochemistry, vol. 82, pp. 663-692, 2013.
McDonald, et al., "No strings attached: the ESCRT machinery in viral budding and cytokinesis," Journal of Cell Science, vol. 122, Pt 13, pp. 2167-2177, 2009.

(56) References Cited

OTHER PUBLICATIONS

Mindell, et al., "Accurate determination of local defocus and specimen tilt in electron microscopy," Journal of Structural Biology, vol. 142, No. 3, pp. 334-347, 2003.
Murshudov, et al., "Refinement of macromolecular structures by the maximum-likelihood method," Acta Crystallographica, Section D: Biological Crystallography, vol. 53, Pt 3, pp. 240-255, 1997.
Nam, et al., "Molecular basis for interaction of let-7 microRNAs with Lin28," Cell, vol. 147, No. 5, pp. 1080-1091, 2011.
Ni, et al., "Crystal structure of the MS2 coat protein dimer: implication for RNA binding and virus assembly," Structure, vol. 3, No. 3, pp. 255-263, 1995.
Ohi, et al., "Negative staining and image classification—powerful tools in modern electron microscopy," Biological Procedures Online, vol. 6, pp. 23-34, 2004.
Olsen, "Gene transfer vectors derived from equine infectious anemia virus," Gene Therapy, vol. 5, No. 11, pp. 1481-1487, 1998.
Otwinowski, et al., "[20] Processing of X-ray diffraction data collected in oscillation mode," Methods in Enzymology, vol. 276, pp. 307-326, 1997.
Oubridge, et al., "Crystal structure at 1.92 A resolution of the RNA-binding domain of the U1A spliceosomal protein complexed with an RNA hairpin," Nature, vol. 372, No. 6505, pp. 432-438, 1994.
Padilla, et al., "Nanohedra: using symmetry to design self assembling protein cages, layers, crystals, and filaments," Proceedings of the National Academy of Sciences USA, vol. 98, No. 5, pp. 2217-2221, 2001.
Pancera, et al., "Structure and immune recognition of trimeric pre-fusion HIV-1 Env.," Nature, vol. 514, No. 7523, pp. 455-461, 2014.
Parent, et al., "Positionally independent and exchangeable late budding functions of the Rous Sarcoma Virus and Human Immunodeficiency Virus Gag proteins," Journal of Virology, vol. 69, No. 9, pp. 5455-5460, 1995.
Patterson, et al., "Characterization of a highly flexible self-assembling protein system designed to form nanocages," Protein Science, vol. 23, No. 2, pp. 190-199, 2014.
PCT/US2014/015371 International Search Report and Written Opinion, 2014.
PCT/US2016/020090, International Search Report and Written Opinion, 10 pages, 2016.
Pesarrodona, et al., "Intracellular targeting of CD44+ cells with self-assembling, protein only nanoparticles," International Journal of Pharmaceutics, vol. 473, No. 1-2, pp. 286-295, 2014.
Pettersen, et al., "UCSF Chimera—a visualization system for exploratory research and analysis," Journal of Computational Chemistry, vol. 25, No. 13, pp. 1605-1612, 2004.
Prodromou, et al, "Recursive PCR: a novel technique for total gene synthesis," Protein Engineering, vol. 5, No. 8, pp. 327-829, 1992.
Puglisi, et al., "Solution structure of a bovine immunodeficiency virus Tat-TAR peptide-RNA complex," Science, vol. 270, No. 5239, pp. 1200-1203, 1995.
Raman, et al., "Design of Peptide Nanoparticles Using Simple Protein Oligomerization Domains," The Open Nanomedicine Journal, vol. 2, pp. 15-26, 2009.
Resh, "Covalent lipid modifications of proteins," Current Biology, vol. 23, No. 10, pp. R431-R435, 2013.
Resh, "Fatty acylation of proteins: new insights into membrane targeting of myristoylated and palmitoylated proteins," Biochimica et Biophysica Acta, vol. 1451, No. 1, pp. 1-16, 1999.
Ringler, et al., "Self-assembly of proteins into designed networks," Science, vol. 302, No. 5642, pp. 106-109, 2003.
Rosa, et al., "HIV-1 Nef promotes infection by excluding SERINC5 from virion incorporation," Nature, vol. 526, No. 1572, pp. 212-217, 2015.
Rothemund, "Folding DNA to create nanoscale shapes and patterns," Nature, vol. 440, No. 7082, pp. 297-302, 2006.
Salgado, et al., "Controlling protein-protein interactions through metal coordination: assembly of a 16-helix bundle protein," Journal of the American Chemical Society, vol. 129, No. 44, pp. 13374-13375, 2007.
Salgado, et al., "Metal-directed protein self-assembly," Accounts of Chemical Research, vol. 43, No. 5, pp. 661-672, 2010.
Schrödinger, LLC, "The PyMOL Molecular Graphics System, Version 1.4," available online at: http://www.pymol.org, 2011.
Schuck, "Size-distribution analysis of macromolecules by sedimentation velocity ultracentrifugation and lamm equation modeling," Biophysical Journal, vol. 78, No. 3, pp. 1606-1619, 2000.
Seeman, "Nanomaterials based on DNA," Annual Review of Biochemistry, vol. 79, pp. 65-87, 2010.
Sheffler, et al., "RosettaHoles2: a volumetric packing measure for protein structure refinement and validation," Protein Science, vol. 19, No. 10, pp. 1991-1995, 2010.
Sinclair, et al., "Generation of protein lattices by fusing proteins with matching rotational symmetry," Nature Nanotechnology, vol. 6, No. 9, pp. 558-562, 2011.
Smith, "XIMDISP—A visualization tool to aid structure determination from electron microscope images," Journal of Structural Biology, vol. 125, No. 2-3, pp. 223-228, 1999.
Stahelin, "Lipid binding domains: more than simple lipid effectors," Journal of Lipid Research, vol. 50, Suppl S299-S304, 2009.
Stranges, et al., "Computational design of a symmetric homodimer using β-strand assembly," Proceedings of the National Academy of Sciences USA, vol. 108, No. 51, pp. 20562-20567, 2011.
Sun, et al., "Cyclic GMP-AMP synthase is a cytosolic DNA sensor that activates the type I interferon pathway," Science, vol. 339, No. 6121, pp. 786-791, 2013.
Théry, et al., "Isolation and Characterization of Exosomes from Cell and Culture Supernatants and Biological Fluids," Current Protocols in Cell Biology, Chapter 3, Unit 3.22, pp. 3.22.1-3.22.19, 2006.
Tobiume, et al., "Nef does not affect the efficiency of human immunodeficiency virus type 1 fusion with target cells," Journal of Virology, vol. 77, No. 19, pp. 10645-10650, 2003.
Tsai, et al., "Analysis of lattice-translocation disorder in the layered hexagonal structure of carboxysome shell protein CsoS1C," Acta Crystallographica, Section D: Biological Crystallography, vol. 65, Pt 9, pp. 980-988, 2009.
Tsvetkova, et al., "Cutting edge: an NK cell-independent role for Slamf4 in controlling humoral autoimmunity," Protein Cages, Methods in Molecular Biology, 1252:1-15, 2014.
Usami, et al., "SERINC3 and SERINC5 restrict HIV-1 infectivity and are counteracted by Nef," Nature, vol. 526, No. 1572, pp. 218-223, 2015.
Usui, et al., "Nanoscale elongating control of the self-assembled protein filament with the cysteine-introduced building blocks," Protein Science, vol. 18, No. 5, pp. 960-969, 2009.
van Heel, et al., "A new generation of the IMAGIC image processing system," Journal of Structural Biology, vol. 116, No. 1, pp. 17-24, 1996.
Votteler, et al., "Virus budding the ESCRT pathway," Cell Host & Microbe, vol. 14, No. 3, pp. 232-241, 2013.
Wang, et al., "Expanding the genetic code of *Escherichia coli*," Science, vol. 292, No. 5516, pp. 498-500, 2001.
Nhitehead, et al., "Optimization of Affinity, Specificity and Function of Designed Influenza Inhibitors Using Deep Sequencing," Nature Biotechnology, vol. 30, No. 6, pp. 543-548, 2012.
Winn, et al., "Macromolecular TLS refinement in REFMAC at moderate resolutions," Methods in Enzymology, vol. 374, pp. 300-321, 2003.
Wu, et al., "Cyclic GMP-AMP is an endogenous second messenger in innate immune signaling by cytosolic DNA," Science, vol. 339, No. 6121, pp. 826-830, 2013.
Yeates et al., "Bacterial microcompartment organelles: protein shell structure and evolution," Annual Review of Biophysics, vol. 39, pp. 185-205, 2010.
Yee et al., "Generation of high-titer pseudotyped retroviral vectors with very broad host range," Methods in Cell Biology, vol. 43, Pt A, pp. 99-112, 1994.
Zaccai, et al., "A de novo peptide hexamer with a mutable channel," Nature Chemical Biology, vol. 7, No. 12, pp. 935-941, 2011.

(56) References Cited

OTHER PUBLICATIONS

Zacharias, et al., "Partitioning of lipid-modified GFPs into membrane microdomains in live cells," Science, vol. 296, No. 5569, pp. 913-916, 2002.

Zhang, "Fabrication of novel biomaterials through molecular self-assembly," Nature Biotechnology, vol. 21, No. 10, pp. 1171-1178, 2003.

Zhao, et al., "A simple guide to biochemical approaches for analyzing lipid-protein interactions," Molecular Biology of the Cell, vol. 23, No. 15, pp. 2823-2830, 2012.

Zheng, et al., "From molecular to macroscopic via the rational design of a self-assembled 3D DNA crystal," Nature, vol. 461, No. 7260, pp. 74-77, 2009.

Zhou, et al., "Genetically encoded short peptide tags for orthogonal protein labeling by Sfp and AcpS phosphopantetheinyl transferases," ACS Chemical Biology, vol. 2, No. 5, pp. 337-346, 2007.

* cited by examiner

POLYPEPTIDES FOR USE IN SELF-ASSEMBLING PROTEIN NANOSTRUCTURES

CROSS REFERENCE

This application claims priority to U.S. Provisional Patent Application Ser. No. 62/074,167 filed Nov. 3, 2014, incorporated by reference herein in its entirety.

STATEMENT REGARDING FEDERALLY SPONSORED RESEARCH

This invention was made with U.S. government support under CHE-1332907, awarded by the National Science Foundation, and DGE-0718124, awarded by the National Science Foundation. The U.S. Government has certain rights in the invention.

BACKGROUND

Molecular self- and co-assembly of proteins into highly ordered, symmetric supramolecular complexes is an elegant and powerful means of patterning matter at the atomic scale. Recent years have seen advances in the development of self-assembling biomaterials, particularly those composed of nucleic acids. DNA has been used to create, for example, nanoscale shapes and patterns, molecular containers, and three-dimensional macroscopic crystals. Methods for designing self-assembling proteins have progressed more slowly, yet the functional and physical properties of proteins make them attractive as building blocks for the development of advanced functional materials.

SUMMARY OF THE INVENTION

In a first aspect, the invention provides isolated polypeptides comprising an amino acid sequence that is at least 75% identical over its length, and identical at least at one identified interface position, to the amino acid sequence of a polypeptide selected from the group consisting of SEQ ID NOS:1-34.

In a second aspect, the invention provides nanostructures, comprising:

(a) a plurality of first assemblies, each first assembly comprising a plurality of identical first polypeptides, wherein the first polypeptides comprise the polypeptide of claim 1; and (b) a plurality of second assemblies, each second assembly comprising a plurality of identical second polypeptides, wherein the second polypeptides comprise the polypeptide of claim 1, and wherein the second polypeptide differs from the first polypeptide;

wherein the plurality of first assemblies non-covalently interact with the plurality of second assemblies to form a nanostructure.

In another aspect, the present invention provides isolated nucleic acids encoding the polypeptides of the invention. In a further aspect, the invention provides nucleic acid expression vectors comprising isolated nucleic acids of the invention. In another aspect, the present invention provides recombinant host cells, comprising a nucleic acid expression vector according to the invention.

In a further aspect, the present invention provides a kit, comprising one or more isolated nanostructures of the invention; one or more of the isolated proteins of the present invention or the assemblies of the present invention; one or more recombinant nucleic acids of the present invention; one or more recombinant expression vectors of the present invention; and/or one or more recombinant host cells of the present invention.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION

Figure 1:
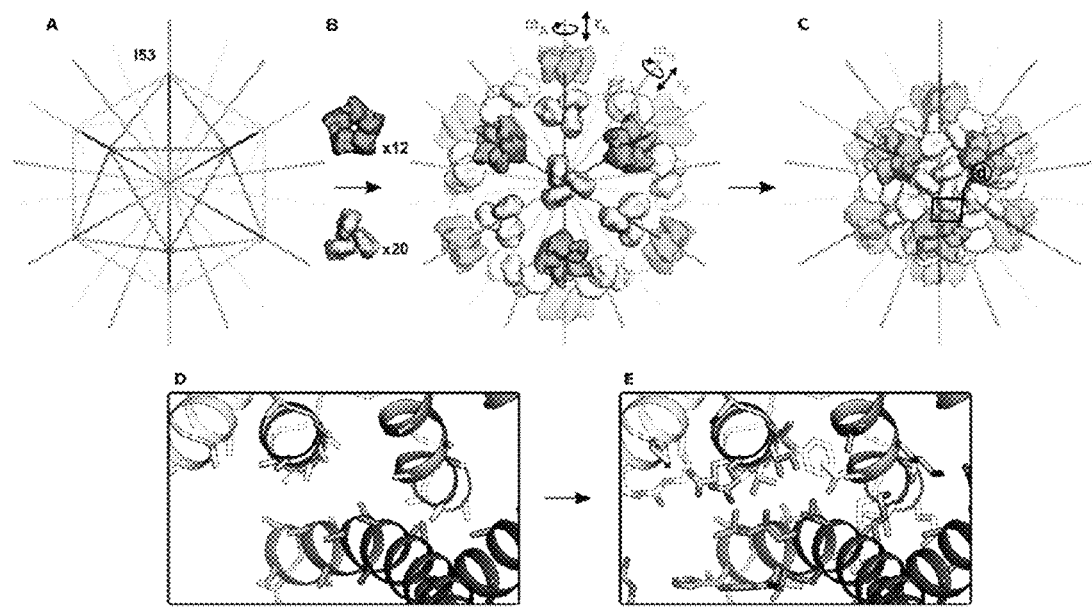
FIG. 1. Overview of the design method utilized to produce the exemplary nanostructures and sequences, illustrated with the I53 icosahedral architecture. (A) A schematic illustration of icosahedral symmetry outlined with dashed lines, with the five-fold symmetry axes shown going through each vertex and three-fold symmetry axes going through each face of the icosahedron. (B) 12 pentamers (dark grey) and 20 trimers (light grey) are aligned along the 5-fold and 3-fold symmetry axes, respectively. Each oligomer possesses two rigid body degrees of freedom, one translational (r) and one rotational (w) that are systematically sampled to identify configurations with large interfaces and high densities of contacting residues suitable for protein-protein interface design. (C) Example of such a docked configuration with a large interface and high density of contacting residues suitable for protein-protein interface design. (D) Close-up of the docked interface between the pentameric and trimeric subunits, as outlined in panel C. Side chains atoms beyond the beta carbon are ignored at this stage of design. (E) New amino acid sequences are designed at the interface to stabilize the modeled configuration.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.). As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). As used herein, "about" means+/−5% of the recited parameter.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the invention provides isolated polypeptide comprising an amino acid sequence that is at least 75% identical over its length, and identical at least at one identified interface position, to the amino acid sequence of a polypeptide selected from the group consisting of SEQ ID NOS: 1-34. The isolated polypeptides of the invention can be used, for example, to prepare the nanostructures of the invention. As described in the examples that follow, the polypeptides of the invention were designed for their ability to self-assemble in pairs to form nanostructures, such as icosahedral nanostructures. The design involved design of suitable interface residues for each member of the polypeptide pair that can be assembled to form the nanostructure. The nanostructures of the invention include symmetrically repeated, non-natural, non-covalent polypeptide-polypeptide interfaces that orient a first assembly and a second assembly into a nanostructure, such as one with an icosahedral symmetry. Starting proteins were those derived from pentameric, trimeric, and dimeric crystal structures from the Protein Data Bank (PDB), along with a small number of crystal structures of de novo designed proteins not yet deposited in the PDB. Thus, each of the polypeptides of the present invention includes one or more modifications at "interface residues" compared to the starting proteins, permitting the polypeptides of the invention to, for example, form icosahedral nanostructures as described herein. Table 1 provides the amino acid sequence of exemplary polypeptides of the invention; the right hand column in Table 1 identifies the residue numbers in each exemplary polypeptide that were identified as present at the interface of resulting assembled nanostructures (i.e.: "identified interface residues"). As can be seen, the number of interface residues for the exemplary polypeptides of SEQ ID NO:1-34 range from 4-13. In various embodiments, the isolated polypeptides of the invention comprise an amino acid sequence that is at least 75%, 80%, 85%, 90%, 91%, 92%, 93%, 94%, 95%, 96%, 97%, 98%, or 99% identical over its length, and identical at least at 1, 2, 3, 4, 5, 6, 7, 8, 9, 10, 11, 12, or 13 identified interface positions (depending on the number of interface residues for a given polypeptide), to the amino acid sequence of a polypeptide selected from the group consisting of SEQ ID NOS: 1-34. In other embodiments, the isolated polypeptides of the invention comprise an amino acid sequence that is at least 75%, 80%, 85%, 90%, 91%, 92%, 93%, 94%, 95%, 96%, 97%, 98%, or 99% identical over its length, and identical at least at 20%, 25%, 33%, 40%, 50%, 60%, 70%, 75%, 80%, 90%, or 100% of the identified interface positions, to the amino acid sequence of a polypeptide selected from the group consisting of SEQ ID NOS: 1-34. In further embodiments, the polypeptides of the invention comprise or consist of a polypeptide having the amino acid sequence of a polypeptide selected from the group consisting of SEQ ID NOS:1-40.

TABLE 1

| Name | Amino Acid Sequence | Identified interface residues |
|---|---|---|
| I53-34A SEQ ID NO: 1 | MEGMDPLAVLAESRLLPLLTVRGGEDLAG LATVLELMGVGALEITLRTEKGLEALKAL RKSGLLLGAGTVRSPKEAEAALEAGAAFL VSPGLLEEVAALAQARGVPYLPGVLTPTE VERALALGLSALKFFPAEPFQGVRVLRAY AEVFPEVRFLPTGGIKEEHLPHYAALPNL LAVGGSWLLQGDLAAVMKKVKAAKALLSP QAPG | I53-34A: 28,32,36, 37,186, 188,191, 192,195 |
| I53-34B SEQ ID NO: 2 | MTKKVGIVDTTFARVDMAEAAIRTLKALS PNIKIIRKTVPGIKDLPVACKKLLEEEGC DIVMALGMPGKAEKDKVCAHEASLGLMLA QLMTNKHIIEVFVHEDEAKDDDELDILAL VRAIEHAANVYYLLFKPEYLTRMAGKGLR QGREDAGPARE | I53-34B: 19,20,23, 24,27, 109,113, 116,117, 120,124, 148 |
| I53-40A SEQ ID NO: 3 | MTKKVGIVDTTFARVDMASAAILTLKMES PNIKIIRKTVPGIKDLPVACKKLLEEEGC DIVMALGMPGKAEKDKVCAHEASLGLMLA QLMTNKHIIEVFVHEDEAKDDAELKILAA RRAIEHALNVYYLLFKPEYLTRMAGKGLR QGFEDAGPARE | I53-40A: 20,23,24, 27,28, 109,112, 113,116, 120,124 |
| I53-40B SEQ ID NO: 4 | MSTINNQLKALKVIPVIAIDNAEDIIPLG KVLAENGLPAAEITFRSSAAVKAIMLLRS AQPEMLIGAGTILNGVQALAAKEAGATFV VSPGFNPNTVRACQIIGIDIVPGVNNPST VEAALEMGLTTLKFFPAEASGGISMVKSL VGPYGDIRLMPTGGITPSNIDNYLAIPQV LACGGTWMVDKKLVTNGEWDEIARLTREI VEQVNP | I53-40B: 47,51,54, 58,74,102 |
| I53-47A SEQ ID NO: 5 | MPIFTLNTNIKATDVPSDFLSLTSRLVGL ILSKPGSYVAVHINTDQQLSFGGSTNPAA FGTLMSIGGIEPSKNRDHSAVLFDHLNAM LGIPKNRMYIHFVNLNGDDVGWNGTTF | I53-47A: 22,25,29, 72,79,86, 87 |
| I53-47B SEQ ID NO: 6 | MNQHSHKDYETVRIAVVRARWHADIVDAC VEAFEIAMAAIGGDRFAVDVFDVPGAYEI PLHARTLAETGRYGAVLGTAFVVNGGIYR HEFVASAVIDGMMNVQLSTGVPVLSAVLT PHRYRDSAEHHRFFAAHFAVKGVEAARAC IEILAAREKIAA | I53-47B: 28,31,35, 36,39, 131,132, 135,139, 146 |
| I53-50A SEQ ID NO: 7 | MKMEELFKKHKIVAVLRANSVEEAIEKAV AVFAGGVHLIEITFTVPDADTVIKALSVL KEKGAIIGAGTVTSVEQCRKAVESGAEFI VSPHLDEEISQFCKEKGVFYMPGVMTPTE LVKAMKLGHTILKLFPGEVVGPQFVKAMK GPFPNVKFVPTGGVNLDNVCEWFKAGVLA VGVGSALVKGTPDEVREKAKAFVEKIRGC TE | I53-50A: 25,29,33, 54,57 |
| I53-50B SEQ ID NO: 8 | MNQHSHKDYETVRIAVVRARWHAEIVDAC VSAFEAAMADIGGDRFAVDVFDVPGAYEI PLHARTLAETGRYGAVLGTAFVVNGGIYR HEFVASAVIDGMMNVQLSTGVPVLSAVLT PHRYRDSDAHTLLFLALFAVKGMEAARAC VEILAAREKIAA | I53-50B: 24,28,36, 124,125, 127,128, 129,131, 132,133, 135,139 |
| I53-51A SEQ ID NO: 9 | MFTKSGDDGNTNVINKRVGKDSPLVNFLG DLDELNSFIGFAISKIPWEDMKKDLERVQ VELFEIGEDLSTQSSKKKIDESYVLWLLA ATAIYRIESGPVKLFVIPGGSEEASVLHV TRSVARRVERNAVKYTKELPEINRMIIVY LNRLSSLLFAMALVANKRRNQSEKIYEIG KSW | I53-51A: 80,83,86, 87,88,90, 91,94, 166,172, 176 |

TABLE 1-continued

| Name | Sequence | Positions |
|---|---|---|
| I53-51B SEQ ID NO: 10 | MNQHSHKDYETVRIAVVRARWHADIVDQC VRAFEEAMADAGGDRFAVDVFDVPGAYEI PLHARTLAETGRYGAVLGTAFVVNGGIYR HEFVASAVIDGMMNVQLSTGVPVLSAVLT PHRYRSSREHHEFFREHFMVKGVEAAAAC ITILAAREKIAA | I53-51B: 31,35,36, 40,122, 124,128, 131,135, 139,143, 146,147 |
| I52-03A SEQ ID NO: 11 | MGHTKGPTPQQHDGSALRIGIVHARWNKT IIMPLLIGTIAKLLECGVKASNIVVQSVP GSWELPIAVQRLYSASQLQTPSSGPSLSA GDLLGSSTTDLTALPTTTASSTGPFDALI AIGVLIKGETMHFEYIADSVSHGLMRVQL DTGVPVIFGVLTVLTDDQAKARAGVIEGS HNHGEDWGLAAVEMGVRRRDWAAGKTE | I52-03A: 28,32,36, 39,44,49 |
| I52-03B SEQ ID NO: 12 | MYEVDHADVYDLFYLGRGKDYAAEASDIA DLVRSRTPEASSLLDVACGTGTHLEHFTK EFGDTAGLELSEDMLTHARKRLPDATLHQ GDMRDFQLGRKFSAVVSMFSSVGYLKTVA ELGAAVASPAEHLEPGGVVVVEPWWFPET FADGWVSADVVRRDGRTVARVSHSVREGN ATRMEVHFTVADPGKGVRHFSDVHLITLF HQREYEAAFMAAGLRVEYLEGGPSGRGLF VGVPA | I52-03B: 94,115, 116,206, 213 |
| I52-32A SEQ ID NO: 13 | MGMKEKFVLIITHGDFGKGLLSGAEVIIG KQENVHTVGLNLGDNIEKVAKEVMRIIIA KLAEDKEIIIVVDLFGGSPFNIALEMMKT FDVKVITGINMPMLVELLTSINVYDTTEL LENISKIGKDGIKVIEKSSLKM | I52-32A: 47,49,53, 54,57,58, 61,83,87, 88 |
| I52-32B SEQ ID NO: 14 | MKYDGSKLRIGILHARWNLEIIAALVAGA IKRLQEFGVKAENIIIETVPGSFELPYGS KLFVEKQKRLGKPLDAIIPIGVLIKGSTM HFEYICDSTTHQLMKLNFELGIPVIFGVL TCLTDEQAERAGLIEGKMHNHGEDWGAA AVEMATKFN | I52-32B: 19,20,23, 30,40 |
| I52-33A SEQ ID NO: 15 | MAVKGLGEVDQKYDGSKLRIGILHARWNR KIILALVAGAVLRLLEFGVKAENIIIETV PGSFELPYGSKLFVEKQKRLGKPLDAIIP IGVLIKGSTMHFEYICDSTTHQLMKLNFE LGIPVIFGVLTCLTDEQAERAGLIEGKM HNHGEDWGAAAVEMATKFN | I52-33A: 33,41,44, 50 |
| I52-33B SEQ ID NO: 16 | MGANWYLDNESSRLSFTSTKNADIAEVHR FLVLHGKVDPKGLAEVEVETESISTGIPL RDMLLRVLVFQVSKFPVAQINAQLDMRPI NNLAPGAQLELRLPLTVSLRGKSHSYNAE LLATRLDERRFQVVTLEPLVIHAQDFDMV RAFNALRLVAGLSAVSLSVPGGAVLIFTA R | I52-33B: 61,63,66, 67,72, 147,148, 154,155 |
| I32-06A SEQ ID NO: 17 | MTDYIRDGSAIKALSFAIILAEADLRHIP QDLQRLAVRVIHACGMVDVANDLAFSEGA GKAGRNALLAGAPILCDARMVAEGITRSR LPADNRVIYTLSDPSVPELAKKIGTNSAA AALDLWLPHIEGSIVAIGNAPTALFRLFE LLDAGAPKPALIIGMPVGPVGAAESKDEL AANSRGVPYVIVRGRRGGSAMTAAAVNAL ASERE | I32-06A: 9,12,13, 14,20,30, 33,34 |
| I32-06B SEQ ID NO: 18 | MITVFGLKSKLAPRREKLAEVIYSSLHLG LDIPKGKHAIRFLCLEKEDFYYPFDRSDD YTVIEINLMAGRSEETKMLLIFLLFIALE RKLGIRAHDVEITIKEQPAHCWGFRGRTG DSARDLDYDIYV | I32-06B: 24,71,73, 76,77,80, 81,84,85, 88,114, 118 |
| I32-19A SEQ ID NO: 19 | MGSDLQKLQRFSTCDISDGLLNVYNIPTG GYFPNLTAISPPQNSSIVGTAYTVLFAPI DDPRPAVNYIDSVPPNSILVLALEPHLQS QFHPFIKITQAMYGGLMSTRAQYLKSNGT VVFGRIRDVDEHRTLNVPFAYGVSCAP KAVVKAVGTNVQLKILTSDGVTQTICPGD YIAGDNNGIVRIPVQETDISKLVTYIEKS IEVDRLVSEAIKNGLPAKAAQTARRMVLK DYI | I32-19A: 208,213, 218,222, 225,226, 229,233 |
| I32-19B SEQ ID NO: 20 | MSGMRVYLGADHAGYELKQAIIAFLKMTG HEPIDCGALRYDADDDYPAFCIAAATRTV ADPGSLGIVLGGSGNGEQIAANKVPGARC ALAWSVQTAALAREHNNAQLIGIGGRMHT LEEALRIVKAFVTTPWSKAQRHQRRIDIL AEYERTHEAPPVPGAPA | I32-19B: 20,23,24, 27,117, 118,122, 125 |
| I32-28A SEQ ID NO: 21 | MGDDARIAAIGDVDELNSQIGVLLAEPLP DDVRAALSAIQHDLFDLGGELCIPGHAAI TEDHLLRLALWLVHYNGQLPPLEEFILPG GARGAALAHVCRTVCRRAERSIKALGASE PLNIAPAAYVNLLSDLLFVLARVLNRAAG GADVLWDRTRAH | I32-28A: 60,61,64, 67,68,71, 110,120, 123,124, 128 |
| I32-28B SEQ ID NO: 22 | MILSAEQSFTLRHPHGQAAALAFVREPAA ALAGVQRLRGLDSDGEQVWGELLVRVPLL GEVDLPFRSEIVRTPQGAELRPLTLTGER AWVAVSGQATAAEGGEMAFAFQFQAHLAT PEAEGEGGAAPFEVMVQAAAGVTLLLVAMA LPQGLAAGLPPA | I32-28B: 35,36,54, 122,129, 137,140, 141,144, 148 |
| I53-40A.1 SEQ ID NO: 23 | MTKKVGIVDTTFARVDMASAAILTLKMES PNIKIIRKTVPGIKDLPVACKKLLEEEGC DIVMALGMPGKKEKDKVCAHEASLGLMLA QLMTNKHIIEVFVHDEDEAKDDAELKILAA RRAIEHALNVYYLLFKPEYLTRMAGKGLR QGFEDAGPARE | I53-40A: 20,23,24, 27,28, 109,112, 113,116, 120,124 |
| I53-40B.1 SEQ ID NO: 24 | MDDINNQLKRLKVIPVIAIDNAEDIIPLG KVLAENGLPAAEITFRSSAAVKAIMLLRS AQPEMLIGAGTILNGVQALAAKEAGADFV VSPGFNPNTVRACQIIGIDIVPGVNNPST VEQALEMGLTTLKFPPAEASGGISMVKSL VGPYGDIRLMPTGGITPDNIDNYLAIPQV LACGGTWMVDKKLVRNGEWDEIARLTREI VEQVNP | I53-40B: 47,51,54, 58,74,102 |
| I53-47A.1 SEQ ID NO: 25 | MPIFTLNTNIKADDVPSDFLSLTSRLVGL ILSKPGSYVAVHINTDQQLSFGGSTNPAA FGTLMSIGGIEPDKNRDHSAVLFDHLNAM LGIPKNRMYIHFVNLNGDDVGWNGTTF | I53-47A: 22,25,29, 72,79,86, 87 |
| I53-47A.1 NegT2 SEQ ID NO: 26 | MPIFTLNTNIKADDVPSDFLSLTSRLVGL ILSEPGSYVAVHINTDQQLSFGGSTNPAA FGTLMSIGGIEPDKNEDHSAVLFDHLNAM LGIPKNRMYIHFVDLDGDDVGWNGTTF | I53-47A: 22,25,29, 72,79,86, 87 |
| I53-47B.1 SEQ ID NO: 27 | MNQHSHKDHETVRIAVVRARWHADIVDAC VEAFEIAMAAIGGDRFAVDVFDVPGAYEI PLHARTLAETGRYGAVLGTAFVVNGGIYR HEFVASAVIDGMMNVQLDTGVPVLSAVLT PHRYRDSDEHHRFFAAHFAVKGVEAARAC IEILNAREKIAA | I53-47B: 28,31,35, 36,39, 131,132, 135,139, 146 |
| I53-47B.1 NegT2 SEQ ID NO: 28 | MNQHSHKDHETVRIAVVRARWHADIVDAC VEAFEIAMAAIGGDRFAVDVFDVPGAYEI PLHARTLAETGRYGAVLGTAFVVNGGIYR HEFVASAVIDGMMNVQLDTGVPVLSAVLT PHEYEDSDEHEFFAAHFAVKGVEAARAC IEILNAREKIAA | I53-47B: 28,31,35, 36,39, 131,132, 135,139, 146 |
| I53-50A.1 SEQ ID NO: 29 | MKMEELFKKHKIVAVLRANSVEEAIEKAV AVFAGGVHLIEITFTVPDADTVIKALSVL KEKGAIIGAGTVTSVEQCRKAVESGAEFI VSPHLDEEISQFCKEKGVFYMPGVMTPTE LVKAMKLGHDILKLFPGEVVGPQFVKAMK GPFPNVKFVPTGGVNLDNVCEWFKAGVLA VGVGDALVKGDPDEVREKAKKFVEKIRGC TE | I53-50A: 25,29,33, 54,57 |
| I53-50A.1 NegT2 SEQ ID NO: 30 | MKMEELFKKHKIVAVLRANSVEEAIEKAV AVFAGGVHLIEITFTVPDADTVIKALSVL KEKGAIIGAGTVTSVEQCRKAVESGAEFI VSPHLDEEISQFCKEKGVFYMPGVMTPTE LVKAMKLGHDILKLFPGEVVGPEFVEAMK GPFPNVKFVPTGGVDLDDVCEWFDAGVLA VGVGDALVEGDPDEVREDAKEFVEEIRGC TE | I53-50A: 25,29,33, 54,57 |

TABLE 1-continued

| | | |
|---|---|---|
| I53-50A.1<br>PosT1<br>SEQ ID<br>NO: 31 | MKMEELFKKHKIVAVLRANSVEEAIEKAV<br>AVFAGGVHLIEITFTVPDADTVIKALSVL<br>KEKGAIIGAGTVTSVEQCRKAVESGAEFI<br>VSPHLDEEISQFCKEKGVFYMPGVMTPTE<br>LVKAMKLGHDILKLFPGEVVGPQFVKAMK<br>GPFPNVKFVPTGGVNLDNVCKWFKAGVLA<br>VGVGKALVKGKPDEVREKAKKFVKKIRGC<br>TE | I53-50A:<br>25,29,33,<br>54,57 |
| I53-50B.1<br>SEQ ID<br>NO: 32 | MNQHSHKDHETVRIAVVRARWHAEIVDAC<br>VSAFEAAMRDIGGDRFAVDVFDVPGAYEI<br>PLHARTLAETGRYGAVLGTAFVVNGGIYR<br>HEFVASAVIDGMMNVQLDTGVPVLSAVLT<br>PHRYRDSDAHTLLFLALFAVKGMEAARAC<br>VEILAAREKIAA | I53-50B:<br>24,28,36,<br>124,125,<br>127,128,<br>129,131,<br>132,133,<br>135,139 |
| I53-50B.1<br>NegT2<br>SEQ ID<br>NO: 33 | MNQHSHKDHETVRIAVVRARWHAEIVDAC<br>VSAFEAAMRDIGGDRFAVDVFDVPGAYEI<br>PLHARTLAETGRYGAVLGTAFVVDGGIYD<br>HEFVASAVIDGMMNVQLDTGVPVLSAVLT<br>PHEYEDSDADTLLFLALFAVKGMEAARAC<br>VEILAAREKIAA | I53-50B:<br>24,28,36,<br>124,125,<br>127,128,<br>129,131,<br>132,133,<br>135,139 |
| I53-50B.4<br>PosT1<br>SEQ ID<br>NO: 34 | MNQHSHKDHETVRIAVVRARWHAEIVDAC<br>VSAFEAAMRDIGGDRFAVDVFDVPGAYEI<br>PLHARTLAETGRYGAVLGTAFVVNGGIYR<br>HEFVASAVINGMMNVQLNTGVPVLSAVLT<br>PHNYDKSKAHTLLFLALFAVKGMEAARAC<br>VEILAAREKIAA | I53-50B:<br>24,28,36,<br>124,125,<br>127,128,<br>129,131,<br>132,133,<br>135,139 |

I53-40 A genus
(SEQ ID NO: 35)
MTKKVGIVDTTFARVDMASAAILTLKMESPNIKIIRKTVPGIKDL

PVACKKLLEEEGCDIVMALGMPGK(A/K)EKDKVCAHEASLGLML

AQLMTNKHIIEVFVHEDEAKDDAELKILAARRAIEHALNVYYLLF

KPEYLTRMAGKGLRQGFEDAGPARE

I53-40 B genus
(SEQ ID NO: 36)
M(S/D)(T/D)INNQLK(A/R)LKVIPVIAIDNAEDIIPLGKVLA

ENGLPAAEITFRSSAAVKAIMLLRSAQPEMLIGAGTILNGVQALA

AKEAGA(T/D)FVVSPGFNPNTVRACQIIGIDIVPGVNNPSTVE (A/Q)ALEMGLTTLKFFPAEASGGISMVKSLVGPYGDIRLMPTGG

ITP(S/D)NIDNYLAIPQVLACGGTWMVDKKLV(T/R)NGEWDEI

ARLTREIVEQVNP

I53-47A genus
(SEQ ID NO: 37)
MPIFTLNTNIKA(T/D)DVPSDFLSLTSRLVGLILS(K/E)PGSY

VAVHINTDQQLSFGGSTNPAAFGTLMSIGGIEP(S/D)KN(R/E)

DHSAVLFDHLNAMLGIPKNRMYIHFV(N/D)L(N/D)GDDVGWNG

TTF

I53-47B genus
(SEQ ID NO: 38)
MNQHSHKD(Y/H)ETVRIAVVRARWHADIVDACVEAFEIAMAAIG

GDRFAVDVFDVPGAYEIPLHARTLAETGRYGAVLGTAFVV(N/D)

GGIY(R/D)HEFVASAVIDGMMNVQL(S/D)TGVPVLSAVLTPH (R/E)Y(R/E)DS(A/D)E(H/D)H(R/E)FFAAHFAVKGVEAAR

ACIEIL(A/N)AREKIAA

I53-50A genus
(SEQ ID NO: 39)
MKMEELFKKHKIVAVLRANSVEEAIEKAVAVFAGGVHLIEITFTV

PDADTVIKALSVLKEKGAIIGAGTVTSVEQCRKAVESGAEFIVSP

HLDEEISQFCKEKGVFYMPGVMTPTELVKAMKLGH(T/D)ILKLF

PGEVVGP(Q/E)FV(K/E)AMKGPFPNVKFVPTGGV(N/D)LD (N/D)VC(E/K)WF(K/D)AGVLAVGVG(S/K/D)ALV(K/E)G (T/D/K)PDEVRE(K/D)AK(A/E/K)FV(E/K)(K/E)IRGCTE

I53-50B genus
(SEQ ID NO: 40)
MNQHSHKD(Y/H)ETVRIAVVRARWHAEIVDACVSAFEAAM (A/R)DIGGDRFAVDVFDVPGAYEIPLHARTLAETGRYGAVLGTA

FVV(N/D)GGIY(R/D)HEFVASAVI(D/N)GMMNVQL(S/D/N)

TGVPVLSAVLTPH(R/E/N)Y(R/D/E)(D/K)S(D/K)A(H/D)

TLLFLALFAVKGMEAARACVEILAAREKIAA

As is the case with proteins in general, the polypeptides are expected to tolerate some variation in the designed sequences without disrupting subsequent assembly into nanostructures: particularly when such variation comprises conservative amino acid substitutions. As used here, "conservative amino acid substitution" means that: hydrophobic amino acids (Ala, Cys, Gly, Pro, Met, See, Sme, Val, Ile, Leu) can only be substituted with other hydrophobic amino acids;

hydrophobic amino acids with bulky side chains (Phe, Tyr, Tip) can only be substituted with other hydrophobic amino acids with bulky side chains; amino acids with positively charged side chains (Arg, His, Lys) can only be substituted with other amino acids with positively charged side chains; amino acids with negatively charged side chains (Asp, Glu) can only be substituted with other amino acids with negatively charged side chains; and amino acids with polar uncharged side chains (Ser, Thr, Asn, Gln) can only be substituted with other amino acids with polar uncharged side chains.

As will be apparent to those of skill in the art, the ability to widely modify surface amino acid residues without disruption of the polypeptide structure permits many types of modifications to endow the resulting self-assembled nanostructures with a variety of functions. In one non-limiting embodiment, the polypeptides of the invention can be modified to facilitate covalent linkage to a "cargo" of interest. In one non-limiting example, the polypeptides can be modified, such as by introduction of various cysteine residues at defined positions to facilitate linkage to one or more antigens of interest, such that a nanostructure of the polypeptides would provide a scaffold to provide a large number of antigens for delivery as a vaccine to generate an improved immune response. In some embodiments, some or all native cysteine residues that are present in the polypeptides but not intended to be used for conjugation may be mutated to other amino acids to facilitate conjugation at defined positions. In another non-limiting embodiment, the polypeptides of the invention may be modified by linkage (covalent or non-covalent) with a moiety to help facilitate "endosomal escape." For applications that involve delivering molecules of interest to a target cell, such as targeted delivery, a critical step can be escape from the endosome—a membrane-bound organelle that is the entry point of the delivery vehicle into the cell. Endosomes mature into lysosomes, which degrade their contents. Thus, if the delivery vehicle does not somehow "escape" from the endosome before it becomes a lysosome, it will be degraded and will not perform its function. There are a variety of lipids or organic polymers that disrupt the endosome and allow escape into the cytosol. Thus, in this embodiment, the polypeptides can be modified, for example, by introducing cysteine residues that will allow chemical conjugation of such a lipid or organic polymer to the monomer or resulting assembly surface. In another non-limiting example, the polypeptides can be modified, for example, by introducing cysteine residues that will allow chemical conjugation of fluorophores or other imaging agents that allow visualization of the nanostructures of the invention in vitro or in vivo.

Surface amino acid residues on the polypeptides can be mutated in order to improve the stability or solubility of the protein subunits or the assembled nanostructures. As will be known to one of skill in the art, if the polypeptide has significant sequence homology to an existing protein family, a multiple sequence alignment of other proteins from that family can be used to guide the selection of amino acid mutations at non-conserved positions that can increase protein stability and/or solubility, a process referred to as consensus protein design (9).

Surface amino acid residues on the polypeptides can be mutated to positively charged (Arg, Lys) or negatively charged (Asp, Glu) amino acids in order to endow the protein surface with an overall positive or overall negative charge. In one non-limiting embodiment, surface amino acid residues on the polypeptides can be mutated to endow the interior surface of the self-assembling nanostructure with a high net charge. Such a nanostructure can then be used to package or encapsulate a cargo molecule with the opposite net charge due to the electrostatic interaction between the nanostructure interior surface and the cargo molecule. In one non-limiting embodiment, surface amino acid residues on the polypeptides can be mutated primarily to Arginine or Lysine residues in order to endow the interior surface of the self-assembling nanostructure with a net positive charge. Solutions containing the polypeptides can then be mixed in the presence of a nucleic acid cargo molecule such as a dsDNA, ssDNA, dsRNA, ssRNA, cDNA, miRNA, siRNA, shRNA, piRNA, or other nucleic acid in order to encapsulate the nucleic acid inside the self-assembling nanostructure. Such a nanostructure could be used, for example, to protect, deliver, or concentrate nucleic acids.

Table 2 lists surface amino acid residue numbers for each exemplary polypeptide of the invention denoted by SEQ ID NOS: 1-34. Thus, in various embodiments, 1 or more (at least 1, 2, 3, 4, 5, 6, 7, 8, 9, 10, 11, 12, 13, 14, 15, 16, 17, 18, 19, 20, 21, 22, 23, 24, 25, 26, 27 28, 29, 30, 31, 32, 33, 34, 35, 36, 37, 38, 39, 40, 41, 42, 43, 44, 45, 46, 47, 48, 49, 50, or more) of these surface residues may be modified in the polypeptides of the invention.

TABLE 2

| Name | Amino Acid Sequence | Surface residues not near interface |
|---|---|---|
| I53-34A SEQ ID NO: 1 | MEGMDPLAVLAESRLLPLLTVRGGEDLAG LATVLELMGVGALEITLRTEKGLEALKAL RKSGLLLGAGTVRSPKEAEAALEAGAAFL VSPGLLEEVAALAQARGVPYLPGVLTPTE VERALALGLSALKFFPAEPFQGVRVLRAY AEVFPEVRFLPTGGIKEEHLPHYAALPNL LAVGGSWLLQGDLAAVMKKVKAAKALLSP QAPG | I53-34A: 6,8,9,12,14,22,25,48,49,50,52,53, 56,73,74,81,94,95,101,102,103, 104,119,122,137,140,143,147, 150,151,153,161,162,163,164, 166,167,170,172,184,193,198, 199,200,202 |
| I53-34B SEQ ID NO: 2 | MTKKVGIVDTTFARVDMAEAAIRTLKALS PNIKIIRKTVPGIKDLPVACKKLLEEEGC DIVMALGMPGKAEKDKVCAHEASLGLMLA QLMTNKHIIEVFVHEDEAKDDDELDILAL VRAIEHAANVYYLLFKPEYLTRMAGKGLR QGREDAGPARE | I53-34B: 3,12,31,33,35,36,51,54,55,56,59, 69,70,71,74,93,103,106,107,108, 131,132,133,134,138,142,153 |
| I53-40A SEQ ID NO: 3 | MTKKVGIVDTTFARVDMASAAILTLKMES PNIKIIRKTVPGIKDLPVACKKLLEEEGC DIVMALGMPGKAEKDKVCAHEASLGLMLA QLMTNKHIIEVFVHEDEAKDDAELKILAA RRAIEHALNVYYLLFKPEYLTRMAGKGLR QGFEDAGPARE | I53-40A: 3,4,31,33,35,36,37,51,54,55,56, 57,59,69,70,71,74,93,103,106, 118,127,128,131,132,133,134, 135,138,139,142,150,153 |
| I53-40B SEQ ID NO: 4 | MSTINNQLKALKVIPVIAIDNAEDIIPLG KVLAENGLPAAEITFRSSAAVKAIMLLRS AQPEMLIGAGTILNGVQALAAKEAGATFV VSPGFNPNTVRACQIIGIDIVPGVNNPST VEAALEMGLTTLKFFPAEASGGISMVKSL VGPYGDIRLMPTGGITPSNIDNYLAIPQV LACGGTWMVDKKLVTNGEWDEIARLTREI VEQVNP | I53-40B: 2,3,7,9,10,12,20,21,23,26,27,30, 34,38,45,60,62,75,85,94,95,122, 124,126,134,139,143,151,153, 161,163,166,167,170,172,180, 184,185,186,189,190,192,193, 194,195,198,201,202,205,208, 209 |
| I53-47A SEQ ID NO: 5 | MPIFTLNTNIKATDVPSDFLSLTSRLVGL ILSKPGSYVAVHINTDQQLSFGGSTNPAA FGTLMSIGGIEPSKNRDHSAVLFDHLNAM LGIPKNRMYIHFVNLNGDDVGWNGTTF | I53-47A: 11,13,14,17,34,36,37,45,47,54,55, 56,65,69,70,71,74,91,92,93,101, 103,105,109,110,112,114 |
| I53-47B SEQ ID NO: 6 | MNQHSHKDYETVRIAVVRARWHADIVDAC VEAFEIAMAAIGGDRFAVDVFDVPGAYEI PLHARTLAETGRYGAVLGTAFVVNGGIYR HEFVASAVIDGMMNVQLSTGVPVLSAVLT | I53-47B: 6,7,8,9,10,11,13,18,20,21,24,43, 44,51,63,67,70,85,87,101,105,122, 123,124,125,126,147,152,153,154 |

TABLE 2-continued

| Name | Amino Acid Sequence | Surface residues not near interface |
|---|---|---|
| | PHRYRDSAEHHRFFAAHFAVKGVEAARAC IEILAAREKIAA | |
| I53-50A SEQ ID NO: 7 | MKMEELFKKHKIVAVLRANSVEEAIEKAV AVFAGGVHLIEITFTVPDADTVIKALSVL KEKGAIIGAGTVTSVEQCRKAVESGAEFI VSPHLDEEISQFCKEKGVFYMPGVMTPTE LVKAMKLGHTILKLFPGEVVGPQFVKAMK GPFPNVKFVPTGGVNLDNVCEWFKAGVLA VGVGSALVKGTPDEVREKAKAFVEKIRGC TE | I53-50A: 4,5,6,8,9,11,17,19,23,37,46,47, 59,74,77,78,81,94,95,98,101,102, 103,106,119,122,126,139,142,145, 149,150,152,160,161,162,163,166, 169,179,183,185,188,191,192,194, 198,199 |
| I53-50B SEQ ID NO: 8 | MNQHSHKDYETVRIAVVRARWHAEIVDAC VSAFEAAMADIGGDRFAVDVFDVPGAYEI PLHARTLAETGRYGAVLGTAFVVNGGIYR HEFVASAVIDGMMNVQLSTGVPVLSAVLT PHRYRDSDAHTLLFLALFAVKGMEAARAC VEILAAREKIAA | I53-50B: 6,7,8,9,10,11,13,18,20,21,34,38, 39,40,43,44,48,51,63,67,70,87, 101,105,118,143,147,152,153,154 |
| I53-51A SEQ ID NO: 9 | MFTKSGDDGNTNVINKRVGKDSPLVNFLG DLDELNSFIGFAISKIPWEDMKKDLERVQ VELFEIGEDLSTQSSKKKIDESYVLWLLA ATAIYRIESGPVKLFVIPGGSEEASVLHV TRSVARRVERNAVKYTKELPEINRMIIVY LNRLSSLLFAMALVANKRRNQSEKIYEIG KSW | I53-51A: 19,20,24,28,46,47,51,70,71,73, 74,75,76,102,122,130,133,134, 135,136,137,140,162,163,164, 165,169,175,177 |
| I53-51B SEQ ID NO: 10 | MNQHSHKDYETVRIAVVRARWHADIVDQC VRAFEEAMADAGGDRFAVDVFDVPGAYEI PLHARTLAETGRYGAVLGTAFVVNGGIYR HEFVASAVIDGMMNVQLSTGVPVLSAVLT PHRYRSSREHHEFFREHFMVKGVEAAAAC ITILAAREKIAA | I53-51B: 6,7,8,9,10,11,13,18,21,27,34,38, 43,48,63,67,70,85,87,101,118, 125,126,129,152,153,154 |
| I52-03A SEQ ID NO: 11 | MGHTKGPTPQQHDGSALRIGIVHARWNKT IIMPLLIGTIAKLLECGVKASNIVVQSVP GSWELPIAVQRLYSASQLQTPSSGPSLSA GDLLGSSTTDLTALPTTTASSTGPFDALI AIGVLIKGETMHFEYIADSVSHGLMRVQL DTGVPVIFGVLTVLTDDQAKARAGVIEGS HNHGEDWGLAAVEMGVRRRDWAAGKTE | I52-03A: 6,9,10,11,13,15,16,26,48,69,75, 76,78,79,111,125,127,142,146, 159,160,161,162,171,175,193, 194,196,197,199,200 |
| I52-03B SEQ ID NO: 12 | MYEVDHADVYDLFYLGRGKDYAAEASDIA DLVRSRTPEASSLLDVACGTGTHLEHFTK EFGDTAGLELSEDMLTHARKRLPDATLHQ GDMRDFQLGRKFSAVVSMFSSVGYLKTVA ELGAAVASFAEHLEPGGVVVVEPWWFPET FADGWVSADVVRRDGRTVARVSHSVREGN ATRMEVHFTVADPGKGVRHFSDVHLITLF HQREYEAAFMAAGLRVEYLEGGPSGRGLF VGVPA | I52-03B: 2,3,5,6,8,15,17,20,22,23,26,27, 30,33,34,35,37,38,40,54,55,57,58, 59,61,62,68,70,71,74,77,78,79, 81,82,84,86,87,91,96,97,98,111, 127,130,131,132,141,144,145, 148,150,154,157,158,159,160, 161,171,172,173,174,177,187, 189,192,198,199,222,223,224, 236 |
| I52-32A SEQ ID NO: 13 | MGMKEKFVLIITHGDFGKGLLSGAEVIIG KQENVHTVGLNLGDNIEKVAKEVMRIIIA KLAEDKEIIVVDLFGGSPFNIALEMMKT FDVKVITGINMPMLVELLTSINVYDTTEL LENISKIGKDGIKVIEKSSLKM | I52-32A: 3,5,15,18,30,32,35,40,41,42,44, 45,65,73,79,91,103,106,109,110, 111,112,114,115,118,122,123, 125,126,129,131 |
| I52-32B SEQ ID NO: 14 | MKYDGSKLRIGILHARWNLEIIAALVAGA IKRLQEFGVKAENIIIETVPGSFELPYGS KLFVEKQKRLGKPLDAIIPIGVLIKGSTM HFEYICDSTTHQLMKLNFELGIPVIFGVL TCLTDEQAEARAGLIEGKMHNHGEDWGAA AVEMATKFN | I52-32B: 4,6,7,9,17,32,35,42,59,63,64,66, 67,68,69,70,71,73,83,85,90,106, 119,120,121,122,125,131,133, 134,135,136,154 |
| I52-33A SEQ ID NO: 15 | MAVKGLGEVDQKYDGSKLRIGILHARWNR KIILALVAGAVLRLLEFGVKAENIIIETV PGSFELPYGSKLFVEKQKRLGKPLDAIIP IGVLIKGSTMHFEYICDSTTHQLMKLNFE LGIPVIFGVLTCLTDEQAEARAGLIEGKM HNHGEDWGAAAVEMATKFN | I52-33A: 12,14,16,17,19,26,27,46,69,73, 74,76,77,78,80,81,83,93,95,100, 116,129,130,131,132,145,164 |
| I52-33B SEQ ID NO: 16 | MGANWYLDNESSRLSFTSTKNADIAEVHR FLVLHGKVDPKGLAEVEVETESISTGIPL RDMLLRVLVFQVSKFPVAQINAQLDMRPI NNLAPGAQLELRLPLTVSLRGKSHSYNAE | I52-33B: 4,6,10,20,21,23,24,31,32,34,36, 39,40,42,44,46,48,56,73,77,79, 81,83,85,88,89,91,92,96,97,99, |

TABLE 2-continued

| Name | Amino Acid Sequence | Surface residues not near interface |
|---|---|---|
| | LLATRLDERRFQVVTLEPLVIHAQDFDMV RAFNALRLVAGLSAVSLSVPVGAVLIFTA R | 101,103,109,110,111,112,114, 124,125,138,140,143,158,175 |
| I32-06A SEQ ID NO: 17 | MTDYIRDGSAIKALSFAIILAEADLRHIP QDLQRLAVRVIHACGMVDVANDLAFSEGA GKAGRNALLAGAPILCDARMVAEGITRSR LPADNRVIYTLSDPSVPELAKKIGNTRSA AALDLWLPHIEGSIVAIGNAPTALFRLFE LLDAGAPKPALIIGMPVGFVGAAESKDEL AANSRGVPYVIVRGRRGGSAMTAAAVNAL ASERE | I32-06A: 24,26,27,41,47,50,51,56,60,63, 64,67,68,77,84,85,86,91,93,98, 99,100,101,102,105,108,109,114, 123,124,125,127,135,142,145, 148,149,152,153,169,172,173, 176,177,180,187,189 |
| I32-06B SEQ ID NO: 18 | MITVFGLKSKLAPRREKLAEVIYSSLHLG LDIPKGKHAIRFLCLEKEDFYYPFDRSDD YTVIEINLMAGRSEETKMLLIFLLFIALE RKLGIRAHDVEITIKEQPAHCWGFRGRTG DSARDLDYDIYV | I32-06B: 8,9,10,13,14,15,16,17,20,34,36, 45,46,47,50,51,53,54,57,67,70, 91,93,95,105,112 |
| I32-19A SEQ ID NO: 19 | MGSDLQKLQRFSTCDISDGLLNVYNIPTG GYFPNLTAISPPQNSSIVGTAYTVLFAPI DDPRPAVNYIDSVPPNSILVLALEPHLQS QFHPFIKITQAMYGGLMSTRAQYLKSNGT VVFGRIRDVDEHRTLNHPVFAYGVGSCAP KAVVKAVGTNVQLKILTSDGVTQTICPGD YIAGDNNGIVRIPVQETDISKLVTYIEKS IEVDRLVSEAIKNGLPAKAAQTARRMVLK DYI | I32-19A: 3,4,6,7,9,10,25,27,36,40,42,43, 44,49,58,59,61,62,63,70,72,73, 74,82,84,88,89,109,110,112,126, 127,129,130,132,146,155,156,157, 159,166,169,172,189,190,192, 194,195,198,201,204,215,232 |
| I32-19B SEQ ID NO: 20 | MSGMRVYLGADHAGYELKQAIIAFLKMTG HEPIDCGALRYDADDDYPAFCIAAATRTV ADPGSLGIVLGGSGNGEQIAANKVPGARC ALAWSVQTAALAREHNNAQLIGIGGRMHT LEEALRWKAFVTTPWSKAQRHQRRIDILA EYERTHEAPPVPGAPA | I32-19B: 4,5,31,33,38,41,42,43,55,56,59, 61,62,83,93,94,101,104,113,119, 129,131,134,136,137,139,140, 143,144,146,147,150,152,153, 156,158,159 |
| I32-28A SEQ ID NO: 21 | MGDDARIAAIGDVDELNSQIGVLLAEPLP DDVRAALSAIQHDLFDLGGELCIPGHAAI TEDHLLRLALWLVHYNGQLPPLEEFILPG GARGAALAHVCRTVCRRAERSIKALGASE PLNIAPAAYVNLLSDLLFVLARVLNRAAG GADVLWDRTRAH | I32-28A: 4,6,7,10,14,27,30,31,33,34,41,44, 45,51,52,53,54,55,56,59,76,78,79, 80,81,82,83,90,103,111,115,116, 131,134,142,145,147,150 |
| I32-28B SEQ ID NO: 22 | MILSAEQSFTLRHPHGQAAALAFVREPAA ALAGVQRLRGLDSDGEQVWGELLVRVPLL GEVDLPFRSEIVRTPQGAELRPLTLTGER AWVAVSGQATAAEGGEMAFAFQFQAHLAT PEAEGEGGAAFEVMVQAAAGVTLLLVAMA LPQGLAAGLPPA | I32-28B: 3,4,6,8,12,15,17,18,22,26,28,32, 38,39,41,43,45,46,48,50,60,66,68, 71,73,74,79,81,82,83,84,86,87, 95,100,103,105,109,111,113,151, 152,155,156,157 |
| I53-40A.1 SEQ ID NO: 23 | MTKKVGIVDTTFARVDMASAAILTLKMES PNIKIIRKTVPGIKDLPVACKKLLEEEGC DIVMALGMPGKKEKDKVCAHEASLGLMLA QLMTNKHIIEVFVHEDEAKDDAELKILAA RRAIEHALNVYYLLFKPEYLTRMAGKGLR QGFEDAGPARE | I53-40A: 3,4,31,33,35,36,37,51,54,55,56, 57,59,69,70,71,74,93,103,106, 118,127,128,131,132,133,134, 135,138,139,142,150,153 |
| I53-40B.1 SEQ ID NO: 24 | MDDINNQLKRLKVIPVIAIDNAEDIIPLG KVLAENGLPAAEITFRSSAAVKAIMLLRS AQPEMLIGAGTILNGVQALAAKEAGADFV VSPGFNPNTVRACQIIGIDIVPGVNNPST VEQALEMGLTTLKFFPAEASGGISMVKSL VGPYGDIRLMPTGGITPDNIDNYLAIPQV LACGGTWMVDKKLVRNGEWDEIARLTREI VEQVNP | I53-40B: 2,3,7,9,10,12,20,21,23,26,27,30, 34,38,45,60,62,75,85,94,95,122, 124,126,134,139,143,151,153, 161,163,166,167,170,172,180, 184,185,186,189,190,192,193, 194,195,198,201,202,205,208, 209 |
| I53-47A.1 SEQ ID NO: 25 | MPIFTLNTNIKADDVPSDFLSLTSRLVGL ILSKPGSYVAVHINTDQQLSFGGSTNPAA FGTLMSIGGIEPDKNRDHSAVLFDHLNAM LGIPKNRMYIHFVNLNGDDVGWNGTTF | I53-47A: 11,13,14,17,34,36,37,45,47,54,55, 56,65,69,70,71,74,91,92,93,101, 103,105,109,110,112,114 |
| I53-47A.1 NegT2 SEQ ID NO: 26 | MPIFTLNTNIKADDVPSDFLSLTSRLVGL ILSEPGSYVAVHINTDQQLSFGGSTNPAA FGTLMSIGGIEPDKNEDHSAVLFDHLNAM LGIPKNRMYIHFVDLDGDDVGWNGTTF | I53-47A: 11,13,14,17,34,36,37,45,47,54,55, 56,65,69,70,71,74,91,92,93,101, 103,105,109,110,112,114 |

TABLE 2-continued

| Name | Amino Acid Sequence | Surface residues not near interface |
|---|---|---|
| I53-47B.1<br>SEQ ID<br>NO: 27 | MNQHSHKDHETVRIAVVRARWHADIVDAC<br>VEAFEIAMAAIGGDRFAVDVFDVPGAYEI<br>PLHARTLAETGRYGAVLGTAFVVNGGIYR<br>HEFVASAVIDGMMNVQLDTGVPVLSAVLT<br>PHRYRDSDEHHRFFAAHFAVKGVEAARAC<br>IEILNAREKIAA | I53-47B:<br>6,7,8,9,10,11,13,18,20,21,24,43,<br>44,51,63,67,70,85,87,101,105,122,<br>123,124,125,126,147,152,153,<br>154 |
| I53-47B.1<br>NegT2<br>SEQ ID<br>NO: 28 | MNQHSHKDHETVRIAVVRARWHADIVDAC<br>VEAFEIAMAAIGGDRFAVDVFDVPGAYEI<br>PLHARTLAETGRYGAVLGTAFVVDGGIYD<br>HEFVASAVIDGMMNVQLDTGVPVLSAVLT<br>PHEYEDSDEDHEFFAAHFAVKGVEAARAC<br>IEILNAREKIAA | I53-47B:<br>6,7,8,9,10,11,13,18,20,21,24,43,<br>44,51,63,67,70,85,87,101,105,122,<br>123,124,125,126,147,152,153,<br>154 |
| I53-50A.1<br>SEQ ID<br>NO: 29 | MKMEELFKKHKIVAVLRANSVEEAIEKAV<br>AVFAGGVHLIEITFTVPDADTVIKALSVL<br>KEKGAIIGAGTVTSVEQCRKAVESGAEFI<br>VSPHLDEEISQFCKEKGVFYMPGVMTPTE<br>LVKAMKLGHDILKLFPGEVVGPQFVKAMK<br>GPFPNVKFVPTGGVNLDNVCEWFKAGVLA<br>VGVGDALVKGDPDEVREKAKKFVEKIRGC<br>TE | I53-50A:<br>4,5,6,8,9,11,17,19,23,37,46,47,<br>59,74,77,78,81,94,95,98,101,102,<br>103,106,119,122,126,139,142,145,<br>149,150,152,160,161,162,163,166,<br>169,179,183,185,188,191,192,194,<br>198,199 |
| I53-50A.1<br>NegT2<br>SEQ ID<br>NO: 30 | MKMEELFKKHKIVAVLRANSVEEAIEKAV<br>AVFAGGVHLIEITFTVPDADTVIKALSVL<br>KEKGAIIGAGTVTSVEQCRKAVESGAEFI<br>VSPHLDEEISQFCKEKGVFYMPGVMTPTE<br>LVKAMKLGHDILKLFPGEVVGPEFVEAMK<br>GPFPNVKFVPTGGVDLDDVCEWFDAGVLA<br>VGVGDALVEGDPDEVREDAKEFVEEIRGC<br>TE | I53-50A:<br>4,5,6,8,9,11,17,19,23,37,46,47,<br>59,74,77,78,81,94,95,98,101,102,<br>103,106,119,122,126,139,142,145,<br>149,150,152,160,161,162,163,166,<br>169,179,183,185,188,191,192,194,<br>198,199 |
| I53-50A.1<br>PosT1<br>SEQ ID<br>NO: 31 | MKMEELFKKHKIVAVLRANSVEEAIEKAV<br>AVFAGGVHLIEITFTVPDADTVIKALSVL<br>KEKGAIIGAGTVTSVEQCRKAVESGAEFI<br>VSPHLDEEISQFCKEKGVFYMPGVMTPTE<br>LVKAMKLGHDILKLFPGEVVGPQFVKAMK<br>GPFPNVKFVPTGGVNLDNVCKWFKAGVLA<br>VGVGKALVKGKPDEVREKAKKFVKKIRGC<br>TE | I53-50A:<br>4,5,6,8,9,11,17,19,23,37,46,47,<br>59,74,77,78,81,94,95,98,101,102,<br>103,106,119,122,126,139,142,145,<br>149,150,152,160,161,162,163,166,<br>169,179,183,185,188,191,192,194,<br>198,199 |
| I53-50B.1<br>SEQ ID<br>NO: 32 | MNQHSHKDHETVRIAVVRARWHAEIVDAC<br>VSAFEAAMRDIGGDRFAVDVFDVPGAYEI<br>PLHARTLAETGRYGAVLGTAFVVNGGIYR<br>HEFVASAVIDGMMNVQLDTGVPVLSAVLT<br>PHRYRDSDAHTLLFLALFAVKGMEAARAC<br>VEILAAREKIAA | I53-50B:<br>6,7,8,9,10,11,13,18,20,21,34,38,<br>39,40,43,44,48,51,63,67,70,87,<br>101,105,118,143,147,152,153,154 |
| I53-50B.1<br>NegT2<br>SEQ ID<br>NO: 33 | MNQHSHKDHETVRIAVVRARWHAEIVDAC<br>VSAFEAAMRDIGGDRFAVDVFDVPGAYEI<br>PLHARTLAETGRYGAVLGTAFVVDGGIYD<br>HEFVASAVIDGMMNVQLDTGVPVLSAVLT<br>PHEYEDSDADTLLFLALFAVKGMEAARAC<br>VEILAAREKIAA | I53-50B:<br>6,7,8,9,10,11,13,18,20,21,34,38,<br>39,40,43,44,48,51,63,67,70,87,<br>101,105,118,143,147,152,153,154 |
| I53-50B.4<br>PosT1<br>SEQ ID<br>NO: 34 | MNQHSHKDHETVRIAVVRARWHAEIVDAC<br>VSAFEAAMRDIGGDRFAVDVFDVPGAYEI<br>PLHARTLAETGRYGAVLGTAFVVNGGIYR<br>HEFVASAVINGMMNVQLNTGVPVLSAVLT<br>PHNYDKSKAHTLLFLALFAVKGMEAARAC<br>VEILAAREKIAA | I53-50B:<br>6,7,8,9,10,11,13,18,20,21,34,38,<br>39,40,43,44,48,51,63,67,70,87,<br>101,105,118,143,147,152,153,154 |

In certain instances, the polypeptides of the present invention can also tolerate non-conservative substitutions. The isolated polypeptides may be produced recombinantly or synthetically, using standard techniques in the art. The isolated polypeptides of the invention can be modified in a number of ways, including but not limited to the ways described above, either before or after assembly of the nanostructures of the invention. As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids.

In another aspect, the invention provides nanostructures, comprising:

(a) a plurality of first assemblies, each first assembly comprising a plurality of identical first polypeptides, wherein the first polypeptides comprise the polypeptide of any embodiment or combination of embodiments of the first aspect of the invention; and (b) a plurality of second assemblies, each second assembly comprising a plurality of identical second polypeptides, wherein the second polypeptides comprise the polypeptide of any embodiment or combination of embodiments of the first aspect of the invention, wherein the second polypeptide differs from the first polypeptide;

wherein the plurality of first assemblies non-covalently interact with the plurality of second assemblies to form a nanostructure.

As described in the examples that follow, a plurality (2, 3, 4, 5, 6, or more) of first polypeptides self-assemble to form a first assembly, and a plurality (2, 3, 4, 5, 6, or more) of second polypeptides self-assemble to form a second assembly. A plurality of these first and second assemblies then self-assemble non-covalently via the designed interfaces to produce the nanostructures of the invention. The designed interfaces on the polypeptides of the invention, resembling natural protein-protein interfaces with well-packed cores composed primarily of hydrophobic amino acid side chains surrounded by a periphery composed primarily of hydrophilic and charged side chains, rigidly orient the assemblies within the nanostructures formed by self-assembly. As will be understood by those of skill in the art, the interaction between the first assembly and the second assembly is a non-covalent protein-protein interaction. Any suitable non-covalent interaction(s) can drive self-interaction of the assemblies to form the nanostructure, including but not limited to one or more of electrostatic interactions, π-effects, van der Waals forces, hydrogen bonding, and hydrophobic effects. In various embodiments, pentamers, trimers, and dimers of the first or second assemblies assemble relative to each other such that their 5-fold, 3-fold, and 2-fold symmetry axes are aligned along icosahedral 5-fold, 3-fold, and 2-fold symmetry axes, respectively.

Figure 2:
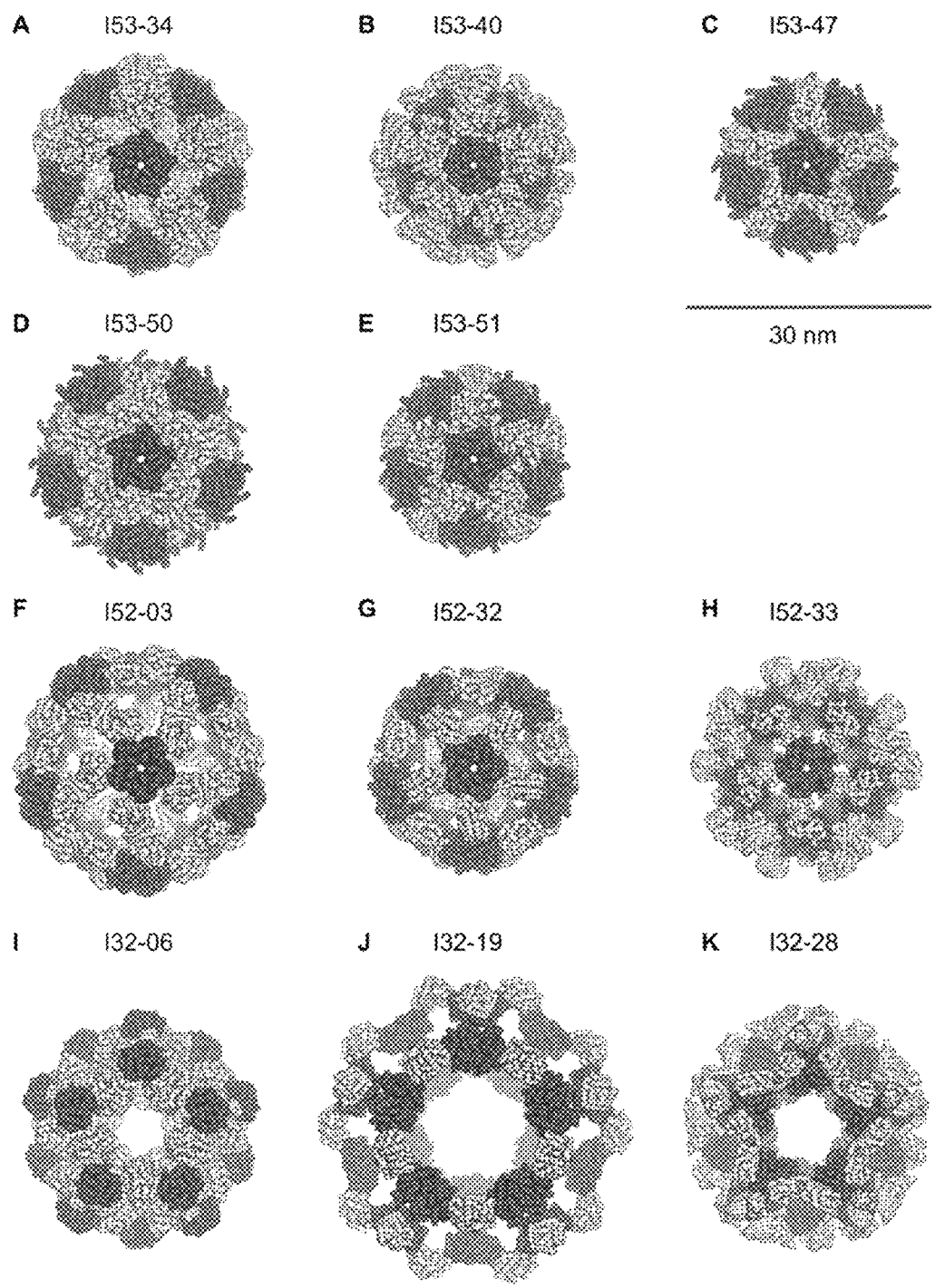
FIG. 2. Design models of exemplary nanostructures. Computational models of the 11 exemplary nanomaterials, (A) I53-34, (B) I53-40, (C) I53-47, (D) I53-50, (E) I53-51, (F) I52-03, (G) I52-32, (H) I52-33, (I) I32-06, (J) I32-19, and (K) I32-28, are shown to scale (relative to the 30 nm scale bar), viewed down one of the 5-fold icosahedral symmetry axes with ribbon-style rendering of the protein backbone. Each I53 material comprises 12 identical pentamers (dark grey) and 20 identical trimers (light grey), each I52 material comprises 12 identical pentamers (dark grey) and 30 identical dimers (light grey), and each I32 material comprises 20 identical trimers (dark grey) and 30 identical dimers (light grey), with the designed interface formed between these oligomeric building blocks. All renderings were generated using PyMOL® Schrödinger, LLC.
Figure 3:
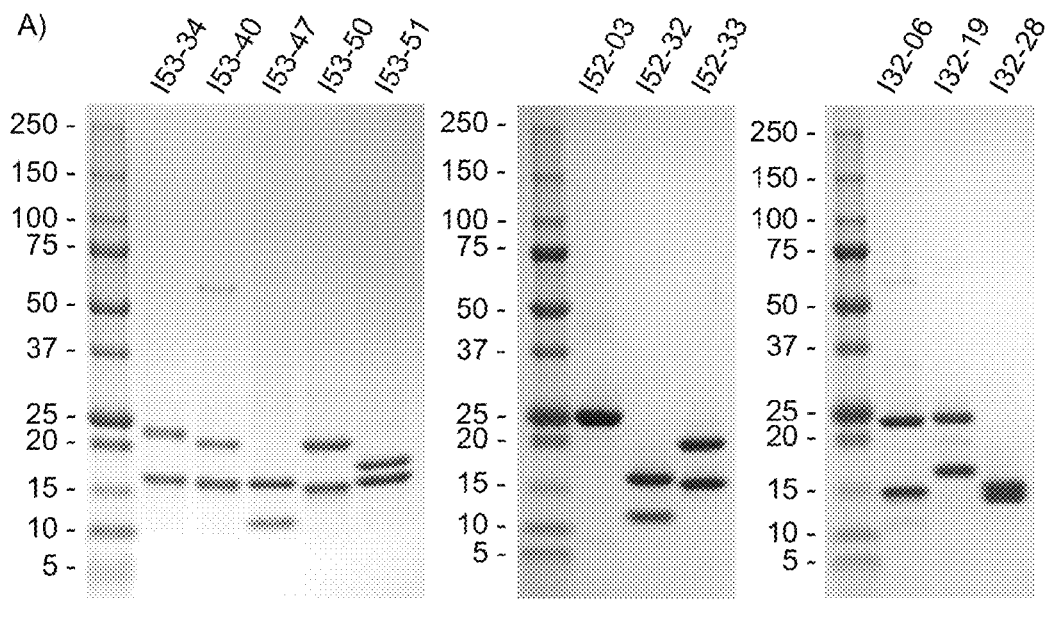
FIG. 3. Sodium dodecyl sulfate polyacrylamide electrophoresis (SDS-PAGE) and mass spectrometry analysis. Pairs of proteins encoding each material were co-expressed (as described in the Methods of Production) in *E. coli*, lysed, and purified via nickel-affinity chromatography followed by gel filtration with a Superose® 6 10/300 GL column (GE Life Sciences). (A) The resulting samples were subjected to SDS-PAGE followed by staining with GelCode® Blue Stain Reagent (Pierce Biotechnology, Inc.). The left lane in each panel contains protein molecular weight standards; the approximate molecular weights in kilodaltons are indicated directly to the left of each band. The right lanes in each panel contain the purified samples. For all of the materials except I52-03, clear bands, of similar staining intensity and near the expected molecular weights of each protein subunit, are present for each of the two proteins comprising the purified materials. (B) While only one band (near the expected molecular weight of 27 kDa for the dimer subunit) is clearly distinguishable for I52-03 via SDS-PAGE, mass spectrometry analysis shows that the other protein subunit is also present in the sample; the mass spectrometry peak at 21,029 Da matches closely with the expected molecular weight of 21,026 Da for the pentamer subunit with loss of the initiator methionine, a common post-translational modification.
Figure 3:
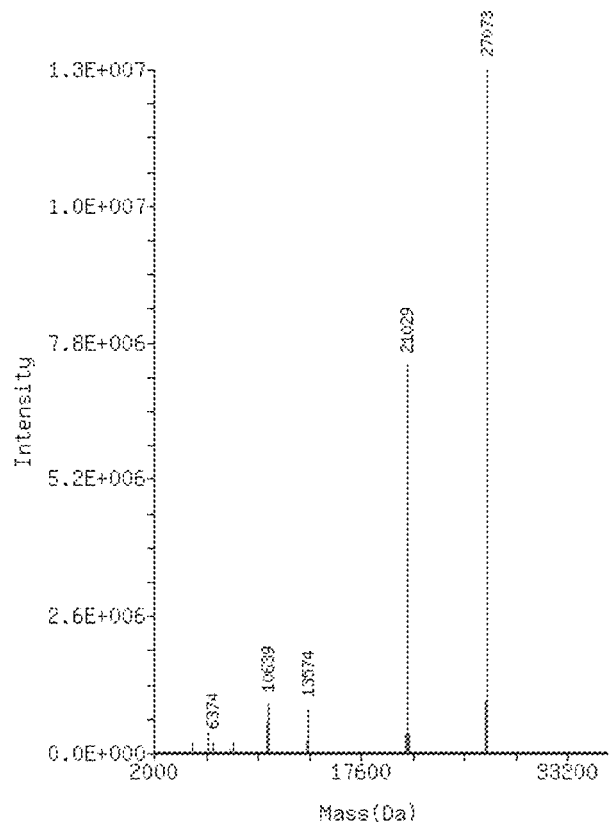
Figure 4:
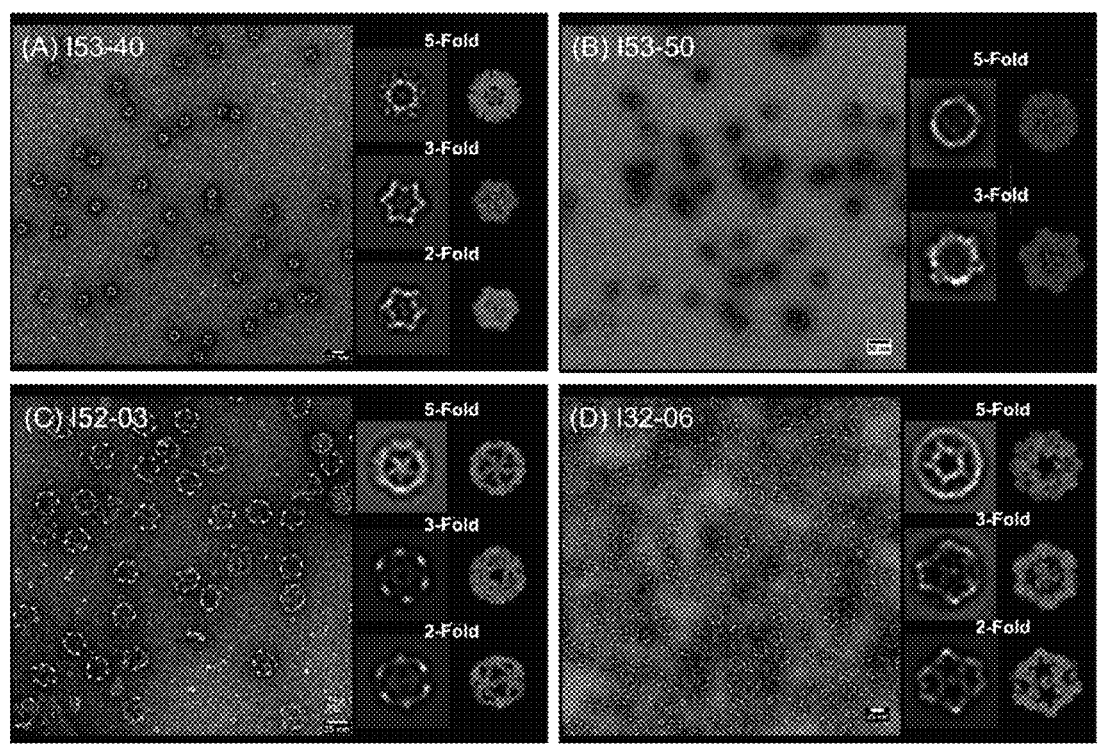
FIG. 4. Negative stain averages. Averages have been obtained of the (A) I53-40, (B) I53-50, (C) I52-03, and (D) I32-06 nanostructures and found to match well with the design models. Raw negative stain micrographs from which the averages were generated are shown on the left side of each panel. Averages (left), along with renderings from the design models (right), are shown on the right side of each panel. Views are shown corresponding approximately to the 5-fold, 3-fold, and 2-fold symmetry axes.
Figure 5:
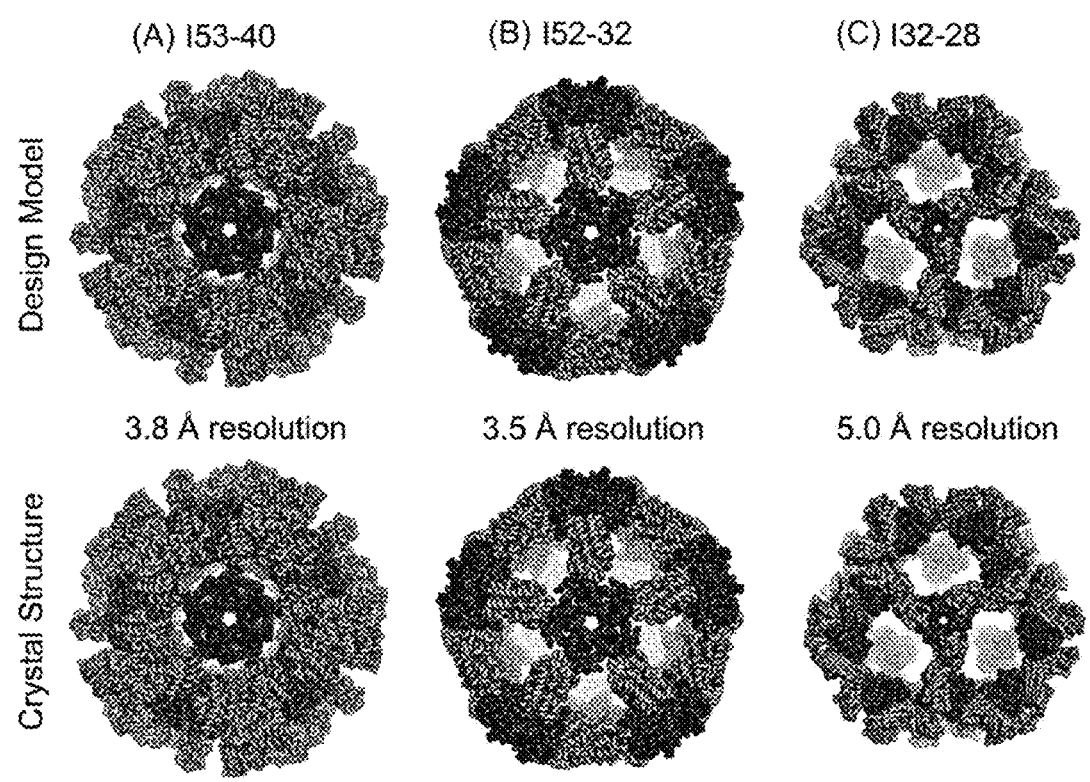
FIG. 5. X-ray crystallography. X-ray crystal structures (bottom) ranging from 3.5 to 5.0 A resolution have been obtained for three of the designed materials, (A) I53-40, (B) I52-32, and (C) I32-28, and found to match closely with the design models (top). Each structure is shown using a ribbon-style rendering. Views of the I53 and I52 designs and crystal structures (panels A and B) are shown looking down one of the 5-fold symmetry axes, while the I32 design model and crystal structure (panel C) are shown looking down one of the 3-fold symmetry axes. Each crystal structure contains only a portion of the full icosahedron in the asymmetric unit. Crystal lattice symmetry was applied to generate the full icosahedra shown in the bottom panel. The I53-40 design model and crystal structure (panel A) comprise 12 pentamers (dark grey) and 20 trimers (light grey), while the I52-32 design model and crystal structure (panel B) comprise 12 pentamers (dark grey) and 30 dimers (light grey), and the I32-28 design model and crystal structure (panel C) comprise 20 trimers (dark grey) and 30 dimers (light grey). All renderings were generated using PyMOL® Schrödinger, LLC.
Figure 6:
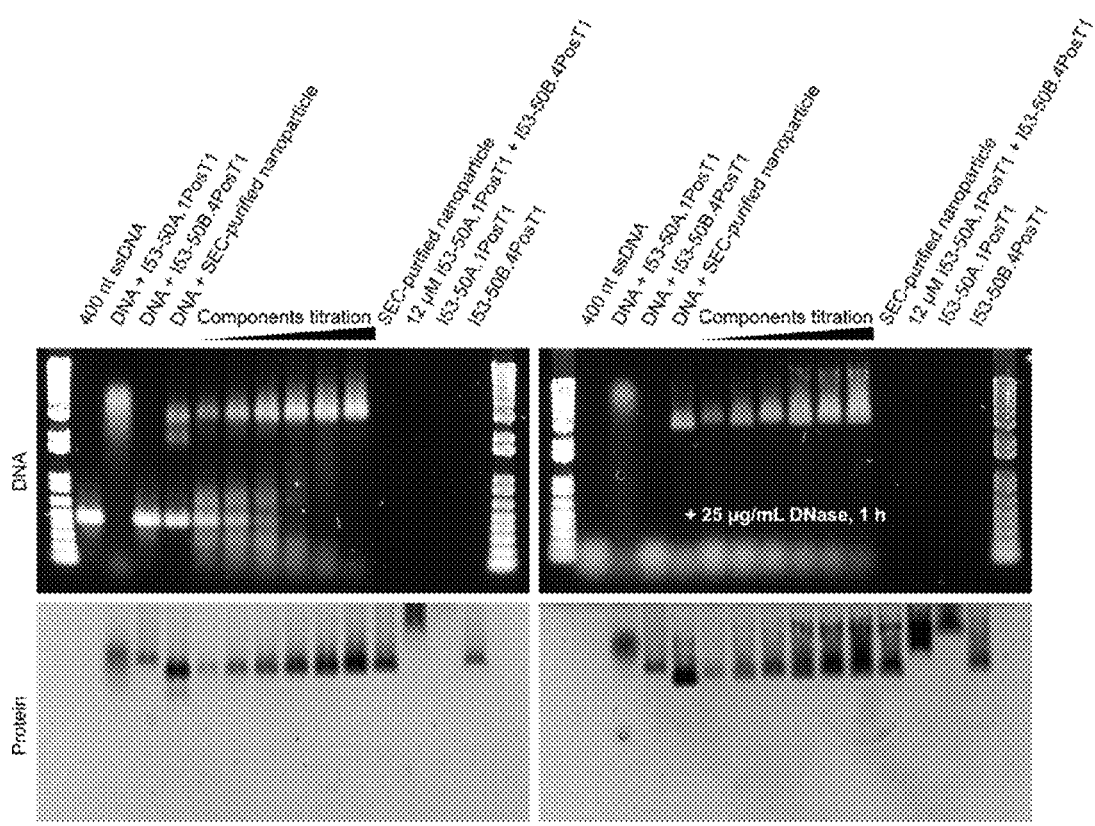
FIG. 6. In vitro assembly of I53-50A.1PosT1+I53-50B.4PosT1 in the presence of 400 nucleotide (nt) ssDNA leads to encapsulation and protection of the ssDNA. Mixtures of 26 ng/µL ssDNA and various proteins were analyzed by agarose gel electrophoretic mobility shift assay (EMSA) after incubation for 16 hours to determine the ability of mixtures of I53-50A.1PosT1+I53-50B.4PosT1 to encapsulate the ssDNA (left; the upper image of the gel is after staining for DNA, while the lower image of the gel is after staining for protein). Mixtures of both components (lanes labeled "Components titration" are mixtures of I53-50A.1PosT1+I53-50B.4PosT1 at 2, 4, 6, 8, 10 and 12 µM) with the DNA shift the DNA such that it migrates similarly to SEC-purified I53-50A.1PosT1+I53-50B.4PosT1 nanoparticles (upper band), while mixtures of DNA with only one protein component or the other do not. The mixtures were then incubated with 25 µg/mL DNase I for 1 hour at room temperature in order to evaluate the ability of the in vitro-assembled nanoparticles to protect the ssDNA cargo from degradation (right; the upper image of the gel is after staining for DNA, while the lower image of the gel is after staining for protein). The DNA that co-migrates with the protein in mixtures of both components (I53-50A.1PosT1+I53-50B.4PosT1; lanes labeled "Components titration" are mixtures at 2, 4, 6, 8, 10 and 12 µM) is largely protected from DNase challenge, while free ssDNA and the mixture of ssDNA+I53-50B.4PosT1 are not. The mixture of ssDNA+I53-50A.1PosT1 is weakly protected, but migrates as a diffuse smear on the gel. Overall, the data show that the ssDNA is encapsulated in nanoparticles formed by I53-50A.1PosT1+I53-50B.4PosT1, which forms a barrier that prevents degradation of the ssDNA by DNase.
Figure 7:
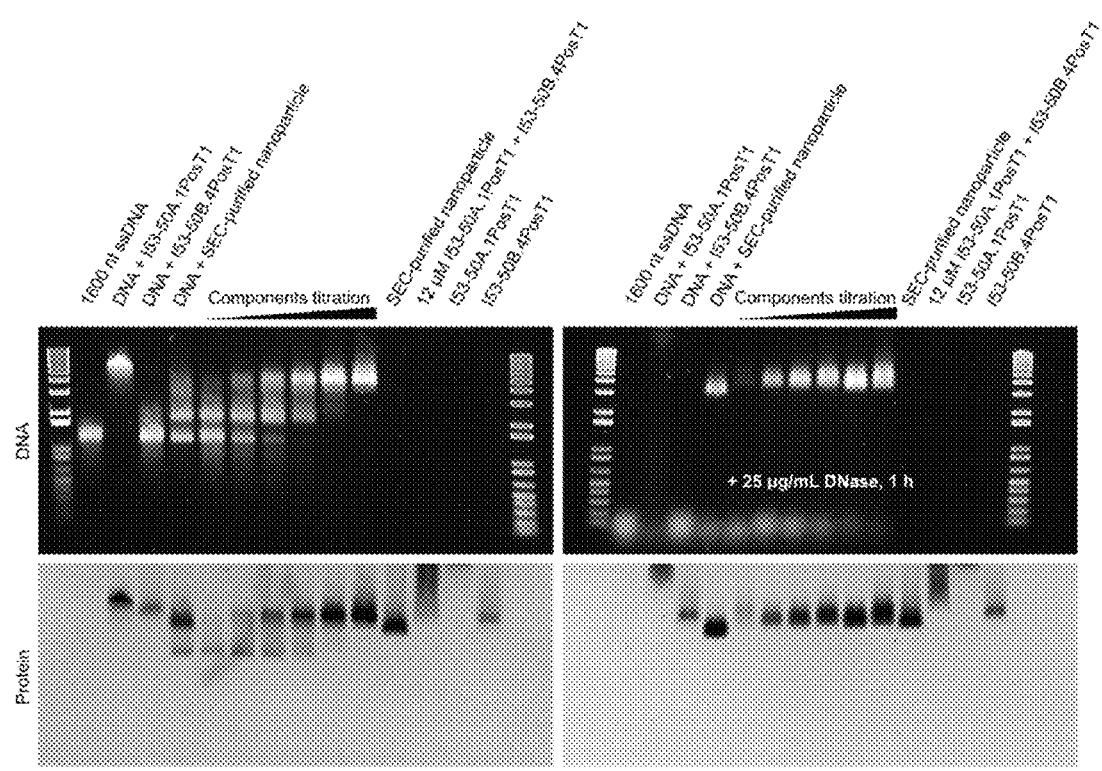
FIG. 7. In vitro assembly of I53-50A.1PosT1+I53-50B.4PosT1 in the presence of 1600 nucleotide (nt) ssDNA leads to encapsulation and protection of the ssDNA. Mixtures of 35.2 ng/µL ssDNA and various proteins were analyzed by agarose electrophoretic mobility shift assay (EMSA) after incubation for 16 hours to determine the ability of mixtures of I53-50A.1PosT1+I53-50B.4PosT1 to encapsulate the ssDNA (left; the upper image of the gel is after staining for DNA, while the lower image of the gel is after staining for protein). Mixtures of both components (lanes labeled "Components titration" are mixtures of I53-50A.1PosT1+I53-50B.4PosT1 at 2, 4, 6, 8, 10 and 12 µM) with the DNA shift the DNA such that it migrates similarly to SEC-purified I53-50A.1PosT1+I53-50B.4PosT1 nanoparticles (upper band), while mixtures of DNA with only one protein component or the other do not. The mixtures were then incubated with 25 µg/mL DNase I for 1 hour at room temperature in order to evaluate the ability of the in vitro-assembled nanoparticles to protect the ssDNA cargo from degradation (right; the upper image of the gel is after staining for DNA, while the lower image of the gel is after staining for protein). The DNA that co-migrates with the protein in mixtures of both components (I53-50A.1PosT1+I53-50B.4PosT1; lanes labeled "Components titration" are mixtures at 2, 4, 6, 8, 10 and 12 µM) is largely protected from DNase challenge, while free ssDNA and the mixture of ssDNA+I53-50B.4PosT1 are not. The mixture of ssDNA+I53-50A.1PosT1 is weakly protected, but migrates as a diffuse smear on the gel. Overall, the data show that the ssDNA is encapsulated in nanoparticles formed by I53-50A.1PosT1+I53-50B.4PosT1, which forms a barrier that prevents degradation of the ssDNA by DNase.

In various other embodiments, the nanostructures are between about 20 nanometers (nm) to about 40 nm in diameter, with interior lumens between about 15 nm to about 32 nm across and pore sizes in the protein shells between about 1 nm to about 14 nm in their longest dimensions (FIG. 2). The nanostructures of the invention can be used for any suitable purpose, including but not limited to delivery vehicles, as the nanostructures can encapsulate molecules of interest and/or the first and/or second proteins can be modified to bind to molecules of interest (diagnostics, therapeutics, detectable molecules for imaging and other applications, etc.). The nanostructures of the invention are well suited for several applications, including vaccine design, targeted delivery of therapeutics, and bioenergy.

In various embodiments of the nanostructure of the invention, the first polypeptides and the second polypeptides comprise polypeptides with the amino acid sequence selected from the following pairs, or modified versions thereof (i.e.: permissible modifications as disclosed for the polypeptides of the invention: isolated polypeptides comprising an amino acid sequence that is at least 75% identical over its length, and identical at least at one identified interface position, to the amino acid sequence indicated by the SEQ ID NO.):

(i) SEQ ID NO:1 and SEQ ID NO:2 (I53-34A and I53-34B);
(ii) SEQ ID NO:3 and SEQ ID NO:4 (I53-40A and I53-40B);
(iii) SEQ ID NO:3 and SEQ ID NO:24 (I53-40A and I53-40B.1);
(iv) SEQ ID NO:23 and SEQ ID NO:4 (I53-40A.1 and I53-40B);
(v) SEQ ID NO:35 and SEQ ID NO:36 (I53-40A genus and I53-40B genus);
(vi) SEQ ID NO:5 and SEQ ID NO:6 (I53-47A and I53-B);
(vii) SEQ ID NO:5 and SEQ ID NO:27 (I53-47A and I53-47B.1);
(viii) SEQ ID NO:5 and SEQ ID NO:28 (I53-47A and I53-47B.1NegT2);
(ix) SEQ ID NO:25 and SEQ ID NO:6 (I53-47A.1 and I53-47B);
(x) SEQ ID NO:25 and SEQ ID NO:27 (I53-47A.1 and I53-47B.1);
(xi) SEQ ID NO:25 and SEQ ID NO:28 (I53-47A.1 and I53-47B.1NegT2);
(xii) SEQ ID NO:26 and SEQ ID NO:6 (I53-47A.1NegT2 and I53-47B);
(xiii) SEQ ID NO:26 and SEQ ID NO:27 (I53-47A.1NegT2 and I53-47B.1);
(xiv) SEQ ID NO:26 and SEQ ID NO:28 (I53-47A.1NegT2 and I53-47B.1NegT2);
(xv) SEQ ID NO:37 and SEQ ID NO:38 (I53-47A genus and I53-47B genus);
(xvi) SEQ ID NO:7 and SEQ ID NO:8 (I53-50A and I53-50B);
(xvii) SEQ ID NO:7 and SEQ ID NO:32 (I53-50A and I53-50B.1);
(xix) SEQ ID NO:7 and SEQ ID NO:33 (I53-50A and I53-50B.1NegT2);
(xx) SEQ ID NO:7 and SEQ ID NO:34 (I53-50A and I53-50B.4PosT1);
(xxi) SEQ ID NO:29 and SEQ ID NO:8 (I53-50A.1 and I53-50B);
(xxii) SEQ ID NO:29 and SEQ ID NO:32 (I53-50A.1 and I53-50B.1);
(xxiii) SEQ ID NO:29 and SEQ ID NO:33 (I53-50A.1 and I53-50B.1NegT2);
(xxiv) SEQ ID NO:29 and SEQ ID NO:34 (I53-50A.1 and I53-50B.4PosT1);
(xxv) SEQ ID NO:30 and SEQ ID NO:8 (I53-50A.1NegT2 and I53-50B);
(xxvi) SEQ ID NO:30 and SEQ ID NO:32 (I53-50A.1NegT2 and I53-50B.1);
(xxvii) SEQ ID NO:30 and SEQ ID NO:33 (I53-50A.1NegT2 and I53-50B.1NegT2);
(xxviii) SEQ ID NO:30 and SEQ ID NO:34 (I53-50A.1NegT2 and I53-50B.4PosT1);
(xxix) SEQ ID NO:31 and SEQ ID NO:8 (I53-50A.1PosT1 and I53-50B);
(xxx) SEQ ID NO:31 and SEQ ID NO:32 (I53-50A.1PosT1 and I53-50B.1);
(xxxi) SEQ ID NO:31 and SEQ ID NO:33 (I53-50A.1PosT1 and I53-50B.1NegT2);
(xxxii) SEQ ID NO:31 and SEQ ID NO:34 (I53-50A.1PosT1 and I53-50B.4PosT1);
(xxxiii) SEQ ID NO:39 and SEQ ID NO:40 (I53-50A genus and I53-50B genus);
(xxxiv) SEQ ID NO:9 and SEQ ID NO:10 (I53-51A and I53-51B);
(xxxv) SEQ ID NO:11 and SEQ ID NO:12 (I52-03A and I52-03B);
(xxxvi) SEQ ID NO:13 and SEQ ID NO:14 (I52-32A and I52-32B);
(xxxv) SEQ ID NO:15 and SEQ ID NO:16 (I52-33A and I52-33B)
(xxxvi) SEQ ID NO:17 and SEQ ID NO:18 (I32-06A and I32-06B);

(xxxvii) SEQ ID NO:19 and SEQ ID NO:20 (I32-19A and I32-19B);
(xxxviii) SEQ ID NO:21 and SEQ ID NO:22 (I32-28A and I32-28B); and
(xxxix) SEQ ID NO:23 and SEQ ID NO:24 (I53-40A.1 and I53-40B.1).

In one embodiment, the nanostructure has icosahedral symmetry. In this embodiment, the nanostructure may comprise 60 copies of the first polypeptide and 60 copies of the second polypeptide. In one such embodiment, the number of identical first polypeptides in each first assembly is different than the number of identical second polypeptides in each second assembly. For example, in one embodiment, the nanostructure comprises twelve first assemblies and twenty second assemblies; in this embodiment, each first assembly may, for example, comprise five copies of the identical first polypeptide, and each second assembly may, for example, comprise three copies of the identical second polypeptide. In another embodiment, the nanostructure comprises twelve first assemblies and thirty second assemblies; in this embodiment, each first assembly may, for example, comprise five copies of the identical first polypeptide, and each second assembly may, for example, comprise two copies of the identical second polypeptide. In a further embodiment, the nanostructure comprises twenty first assemblies and thirty second assemblies; in this embodiment, each first assembly may, for example, comprise three copies of the identical first polypeptide, and each second assembly may, for example, comprise two copies of the identical second polypeptide. All of these embodiments are capable of forming synthetic nanomaterials with regular icosahedral symmetry. In various further embodiments, oligomeric states of the first and second polypeptides are as follows:

I53-34A: trimer+I53-34B: pentamer;
I53-40A: pentamer+I53-40B: trimer;
I53-47A: trimer+I53-47B: pentamer;
I53-50A: trimer+I53-50B: pentamer;
I53-51A: trimer+I53-51B: pentamer;
I32-06A: dimer+I32-06B: trimer;
I32-19A: trimer+I32-19B: dimer;
I32-28A: trimer+I32-28B: dimer;
I52-03A: pentamer+I52-03B: dimer;
I52-32A: dimer+I52-32B: pentamer; and
I52-33A: pentamer+I52-33B: dimer.

As disclosed in the examples that follow, the nanostructures form spontaneously when appropriate polypeptide pairs are co-expressed in *E. coli* cells, yielding milligram quantities of purified material per liter of cell culture using standard methods of immobilized metal-affinity chromatography and gel filtration. When a poly-histidine purification tag is appended to just one of the two distinct polypeptide subunits (i.e.: the first and second polypeptides) comprising each nanostructure, the other subunit is found to co-purify with the tagged subunit.

In one embodiment, the nanostructure further comprises a cargo within the nanostructure. As used herein, a "cargo" is any compound or material that can be incorproated on and/or within the nanostructure. For example, polypeptide pairs suitable for nanostructure self-assembly can be expressed/purified independently; they can then be mixed in vitro in the presence of a cargo of interest to produce the nanostructure comprising a cargo. This feature, combined with the protein nano structures' large lumens and relatively small pore sizes, makes them well suited for the encapsulation of a broad range of cargo including, but not limited to, small molecules, nucleic acids, polymers, and other proteins. In turn, the protein nanostructures of the present invention could be used for many applications in medicine and biotechnology, including targeted drug delivery and vaccine design. For targeted drug delivery, targeting moieties could be fused or conjugated to the protein nanostructure exterior to mediate binding and entry into specific cell populations and drug molecules could be encapsulated in the cage interior for release upon entry to the target cell or subcellular compartment. For vaccine design, antigenic epitopes from pathogens could be fused or conjugated to the cage exterior to stimulate development of adaptive immune responses to the displayed epitopes, with adjuvants and other immunomodulatory compounds attached to the exterior and/or encapsulated in the cage interior to help tailor the type of immune response generated for each pathogen. The polypeptide components may be modified as noted above. In one non-limiting example, the polypeptides can be modified, such as by introduction of various cysteine residues at defined positions to facilitate linkage to one or more antigens of interest as cargo, and the nanostructure could act as a scaffold to provide a large number of antigens for delivery as a vaccine to generate an improved immune response. Other modifications of the polypeptides as discussed above may also be useful for incorporating cargo into the nanostructure.

In certain embodiments, the nanostructures may comprise one or more peptides configured to bind or fuse with desired immunogens. In certain further embodiments, the nanostructure comprises one or more copies of variants designed to form a nanostructure of the trimeric proteins 1WOZ or 1WA3 (PDB ID codes), which have been demonstrated to be suitable for fusion with the trimeric HIV immunogen, BG505 SOSIP (4-6). Such nanostructures could be used as scaffolds for the design of an HIV vaccine capable of inducing protective immune responses against the virus. In another embodiment, the nanostructures of the present invention could be useful as scaffolds for the attachment of enzymes on the interior and/or exterior of the cages. Such enzymes confer on the nanostructure the ability to catalyze biochemical pathways or other reactions. Such patterning has been shown to be important in natural systems in order to increase local substrate concentrations, sequester toxic intermediates, and/or reduce the rates of undesirable side reactions (7, 8). In another embodiment, the cargo may comprise a detectable cargo. For example, the nanostructures of the present invention could also be useful as single-cell or single-molecule imaging agents. The materials are large enough to be identified in cells by electron microscopy, and when tagged with fluorophores they are readily detectable by light microscopy. This feature makes them well-suited to the task of correlating images of the same cells taken by light microscopy and electron microscopy.

In another aspect, the present invention provides isolated nucleic acids encoding a protein of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the invention.

In a further aspect, the present invention provides recombinant expression vectors comprising the isolated nucleic acid of any embodiment or combination of embodiments of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2nd Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide.

In a further aspect, the present invention provides kits comprising:

(a) one or more of the isolated polypeptides, polypeptide assemblies, or nanostructures of the invention;

(b) one or more recombinant nucleic acids of the invention;

(c) one or more recombinant expression vectors comprising recombinant nucleic acids of the invention; and/or (d) one or more recombinant host cell, comprising recombinant expression vectors of the invention.

In yet a further aspect, the present invention provides methods of using the nanostructures of the present invention. In cases where both polypeptides comprising an assembly are capable of independent expression and purification, this enables control over assembly through mixing of purified components in vitro. This feature, combined with the nanostructures' large lumens and relatively small pore sizes, makes them well suited for the encapsulation of a broad range of other materials including small molecules, nucleic acids, polymers, and other proteins, as discussed above. In turn, the nanostructures of the present invention could be used for many applications in medicine and biotechnology, including targeted drug delivery and vaccine design. For targeted drug delivery, targeting moieties could be fused or conjugated to the nanostructure exterior to mediate binding and entry into specific cell populations and drug molecules could be encapsulated in the cage interior for release upon entry to the target cell or sub-cellular compartment. For vaccine design, antigenic epitopes from pathogens could be fused or conjugated to the nanostructure exterior to stimulate development of adaptive immune responses to the displayed epitopes, with adjuvants and other immunomodulatory compounds attached to the exterior and/or encapsulated in the cage interior to help tailor the type of immune response generated for each pathogen. Other uses will be clear to those of skill in the art based on the disclosure relating to polypeptide modifications, nanostructure design, and cargo incorporation.

EXAMPLES

Methods of production: The icosahedral materials disclosed herein (amino acid sequences provided in Table 1), which comprise possible embodiments of the present invention, were produced as follows. The initial sequences and structures for the design process were derived from pentameric, trimeric, and dimeric crystal structures from the Protein Data Bank (PDB), along with a small number of crystal structures of de novo designed proteins not yet deposited in the PDB.

The PDB Accession numbers for the wild type scaffold proteins related to the exemplary polypeptides of the invention are as follows:

SEQ ID NO:1 (I53-34A): 2yw3;
SEQ ID NO:2 (I53-34B): 2b98;
SEQ ID NO:3 (I53-40A): 2b98;
SEQ ID NO:4 (I53-40B): 4e38;
SEQ ID NO:5 (I53-47A): 1hfo;
SEQ ID NO:6 (I53-47B): 2obx;
SEQ ID NO:7 (I53-50A): 1wa3;
SEQ ID NO:8 (I53-50B): 2obx;
SEQ ID NO:9 (I53-51A): 1woz;
SEQ ID NO:10 (I53-51B): 2obx;
SEQ ID NO:11 (I52-03A): 1c41;
SEQ ID NO:12 (I52-03B): 3bxo;
SEQ ID NO:13 (I52-32A): 3lfh;
SEQ ID NO:14 (I52-32B): 2jfb;
SEQ ID NO:15 (I52-33A): 2jfb;
SEQ ID NO:16 (I52-33B): 3q34;
SEQ ID NO:17 (I32-06A): 3e7d;
SEQ ID NO:18 (I32-06B): 1mww;

SEQ ID NO:19 (I32-19A): 2c5q;
SEQ ID NO:20 (I32-19B): 2vvp;
SEQ ID NO:21 (I32-28A): 2zhz; and
SEQ ID NO:22 (I32-28B): 3nqn.

15,552 pairs of pentamers and trimers, 50,400 pairs of pentamers and dimers, and 344,825 pairs of trimers and dimers were arranged in icosahedral symmetry with the 5-fold symmetry axes of the pentamers, 3-fold symmetry axes of the trimers, and 2-fold symmetry axes of the dimers aligned along the 5-fold, 3-fold, and 2-fold icosahedral symmetry axes, respectively. While maintaining perfect icosahedral symmetry, rotations and translations along these axes were sampled to identify configurations predicted to be suitable for protein-protein interface design. In total, 68,983 I53, 35,468 I52, and 177,252 I32 configurations were designed, yielding 71 pairs of I53 protein sequences, 44 pairs of I52 protein sequences, and 68 pairs of I32 protein sequences predicted to fold and assemble into the modeled icosahedral complexes.

Genes encoding the 71 pairs of I53 sequences were synthesized and cloned into a variant of the pET29b expression vector (Novagen, Inc.) between the NdeI and XhoI endonuclease restriction sites. Genes encoding the 44 pairs of I52 sequences and 68 pairs of I32 sequences were synthesized and cloned into a variant of the pET28b expression vector (Novagen, Inc.) between the NcoI and XhoI endonuclease restriction sites.

The two protein coding regions in each DNA construct are connected by an intergenic region. The intergenic region in the I53 designs was derived from the pETDuet-1 vector (Novagen, Inc.) and includes a stop codon, T7 promoter/lac operator, and ribosome binding site.

The intergenic region in the I52 and I32 designs only includes a stop codon and ribosome binding site. The sequences of the I53, I52 and I32 intergenic regions are as follows:

I53 intergenic region DNA sequence:

```
                                         (SEQ ID NO: 41)
5'-TAATGCTTAAGTCGAACAGAAAGTAATCGTATTGTACACGGC

CGCATAATCGAAATTAATACGACTCACTATAGGGGAATTGTGAGC

GGATAACAATTCCCCATCTTAGTATATTAGTTAAGTATAAGAAGG

AGATATACTT-3'
```

I52 intergenic region DNA sequence:

```
                                         (SEQ ID NO: 42)
                     5'-TAAAGAAGGAGATATCAT-3'
```

I32 intergenic region DNA sequence:

```
                                         (SEQ ID NO: 43)
                     5'-TGAGAAGGAGATATCAT-3'
```

The constructs for the I53 protein pairs thus possess the following set of elements from 5' to 3': NdeI restriction site, upstream gene, intergenic region, downstream gene, XhoI restriction site. The constructs for the I52 and I32 protein pairs possess the following set of elements from 5' to 3': NcoI restriction site, upstream gene, intergenic region, downstream gene, XhoI restriction site. In each case, the upstream genes encode components denoted with the suffix "A"; the downstream genes encode the "B" components (Table 1). This allows for co-expression of the designed protein pairs in which both the upstream and downstream genes have their own ribosome binding site, and in the case of the I53 designs, both genes also have their own T7 promoter/lac operator.

For purification purposes, each co-expression construct includes a 6×-histidine tag (HHHHHH) appended to the N- or C-terminus of one of the two protein coding regions.

Expression plasmids were transformed into BL21(DE3) *E. coli* cells. Cells were grown in LB medium supplemented with 50 mg L$^{-1}$ of kanamycin (Sigma) at 37° C. until an OD600 of 0.8 was reached. Protein expression was induced by addition of 0.5 mM isopropyl-thio-β-D-galactopyranoside (Sigma) and allowed to proceed for either 5 h at 22° C. or 3 h at 37° C. before cells were harvested by centrifugation.

The designed proteins were first screened for soluble expression and co-purification at small scale from 2 to 4 mL cultures by nickel affinity chromatography using His MultiTrap® FF nickel-coated filter plates (GE Healthcare). Purification products were analyzed by SDS-PAGE to identify those containing species near the expected molecular weight of both protein subunits (indicating co-purification). Those found to contain both subunits were subsequently subjected to native (non-denaturing) PAGE to identify slow migrating species further indicating assembly to higher order materials. Those designs appearing to co-purify and yielding slowly migrating species by native PAGE were subsequently expressed at larger scale (1 to 12 liters of culture) and purified by nickel affinity chromatography via gravity columns with nickel-NTA resin (Qiagen) or His-Trap® HP columns (GE Healthcare). Fractions containing the designed proteins were pooled, concentrated using centrifugal filter devices (Sartorius Stedim Biotech), and further purified on a Superose® 6 10/300 gel filtration column (GE Healthcare).

The purified proteins were analyzed by size exclusion chromatography using a Superose® 6 10/300 column to assess their assembly states. For each of the exemplary proteins described here, major peaks were observed in the chromatograms near elution volumes of 8.5 to 12 mL, which correspond well with the expected elution volumes for the designed 120-subunit icosahedral nanostructures. Within this set of exemplary proteins, the relative elution volumes correspond with the physical dimensions of the computational design models of the nanostructures, that is, proteins designed to assemble into relatively larger nanostructures yielded peaks at earlier elution volumes while those designed to assemble into relatively smaller nanostructures yielded peaks at later elution volumes. In some cases, smaller secondary peaks were observed at slightly earlier elution volumes than the predominant peak, suggesting transient or low-affinity dimerization of the nanostructures.

Gel filtration fractions containing pure protein in the desired assembly state were analyzed by negative stain electron microscopy as described previously (2). Electron micrographs showing fields of particles of the expected size and shape have been obtained for 10 of the nanostructures. In one case (I32-19), the nanostructure appears to be unstable in the conditions encountered during grid preparation, precluding visualization by electron microscopy.

To further validate the structures of our materials, small angle X-ray scattering (SAXS) data was obtained for several of the designed nanostructures. Scattering measurements were performed at the SIBYLS® 12.3.1 beamline at the Advanced Light Source, LBNL, on 20 microliter samples loaded into a helium-purged sample chamber (10). Data were collected on gel filtration fractions and samples concentrated ~2×-10× from individual fractions, with the gel filtration buffer and concentrator eluates used for buffer subtraction. Sequential exposures ranging from 0.5 to 5 seconds were taken at 12 keV to maximize signal to noise, with visual checks for radiation-induced damage to the protein. The FOXS® algorithm (11, 12) was then used to calculate scattering profiles from our design models and fit them to the experimental data. The major features of the I53-34, I53-40, I53-47, I53-50, I52-03, I52-32, I52-33, I32-06, I32-19, and I32-28 design models were all found to match well with the experimental data, supporting the conclusion that the nanostructures assemble to the intended assembly state and three-dimensional configuration in solution. Graphs of the log of the scattering intensity, I(q), as a function of scattering angle, q, show multiple large dips in the scattering intensity in the low q region between 0.015 $A^{-1}$ and 0.15 $A^{-1}$, each of which is closely recapitulated in the theoretical profiles calculated from the design models. Although the I53-51 design model was not found to match well with the SAXS data, this appears likely to be due to low stability of the designed material, which caused it to be primarily unassembled at the concentrations used for the SAXS measurements; this result is consistent with our findings from gel filtration of I53-51, in which significant peaks were observed corresponding to the unassembled pentamers and trimers in addition to the presumed 120-subunit assembly peak.

Using the Rosetta macromolecular modeling suite, the computational models of designed I53 materials were redesigned by allowing optimization of the identities of relatively exposed residues (defined as having a solvent accessible surface area of greater than 20 square Ångstroms), excepting polar residues (Aspartate, Glutamate, Histidine, Lysine, Asparagine, Glutamine, and Arginine) and residues near the designed protein-protein interfaces between the pentameric and trimeric components. Mutations that resulted in losses of significant atomic packing interactions or side chain-backbone hydrogen bonds were discarded. A position-specific scoring matrix (PSSM) based on homologous protein sequences was used to augment the Rosetta scorefunction to favor residues that appear frequently at a given position in homologous proteins, a design approach referred to as consensus protein design (9). Multiple design trajectories were performed with varying weights on the contribution of the PSSM, and mutations to polar residues that appeared favorable across all design trajectories were selected for inclusion in the variant protein. These variants were designated by the addition of "0.1" to the end of their names (e.g., I53-50A.1).

The Rosetta macromolecular modeling suite was used to mutate manually selected amino acid positions to charged amino acids in order to generate variant nanoparticles featuring highly positively or negatively charged interior surfaces. To generate negatively charged nanoparticles (denoted by the letters "Neg" in their names), mutations were limited to either Aspartate or Glutamate. To generate positively charged nanoparticles (denoted by the letters "Pos" in their names), mutations were limited to either Arginine or Lysine. Relevant score metrics for each mutation were independently assessed, and favorable mutations were sorted into two tiers based on their scores. Two new nanoparticle variants sequences were then designed for each individual protein for each type of charge, one including only the Tier 1 mutations (named "T1") and the other including both the Tier 1 and Tier 2 mutations (named "T2"). In most cases, the charged mutations were incorporated into the consensus redesign variants described above.

Genes encoding the I53 "0.1" and charged variant proteins were synthesized and cloned into the pET29b expression vector (Novagen, Inc.) between the NdeI and XhoI endonuclease restriction sites. Constructs were produced in two formats. In the first, the two proteins were encoded in a bicistronic arrangement on a single expression plasmid as described above for co-expression in E. coli. In the second, each protein component (i.e., the pentameric component and the trimeric component) were cloned individually into pET29b for expression in the absence of the other component.

For purification purposes, each co-expression construct included a 6×-histidine tag (HHHHHH) appended to the N- or C-terminus of one of the two protein coding regions. Similarly, each individual expression construct included a 6×-histidine tag appended to the N- or C-terminus of the protein coding region.

The "0.1" and charged variant proteins were expressed and purified as described above with two differences. First, expression at 18° C. was evaluated in addition to expression at 37° C. at small scale for all variants, and, in some cases, expression at 18° C. was used to produce the proteins at multi-liter scale. Second, for some variants, the detergent 3-[(3-cholamidopropyl)dimethylammonio]-1-propanesulfonate (CHAPS) was included in all purification buffers at a concentration of 0.75% weight/volume to prevent protein aggregation.

After purification of individually expressed protein components, pairs of components designed to co-assemble into a nanoparticle (e.g., I53-40.1A and I53-40.1B) were mixed in equimolar amounts in buffer and allowed to incubate at room temperature for 1-24 hours, a procedure we refer to as "in vitro assembly." For assemblies including charged components, the buffer included 500 mM NaCl; in all other cases the buffer included 150 mM NaCl. The mixtures were fractionated and analyzed on a Superose® 6 10/300 gel filtration column (GE Healthcare), and fractions were analyzed by SDS-PAGE to determine the protein contents of each elution peak.

In one exemplary embodiment, the I53-40.1A and I53-40.1B protein variants, based off of I53-40A and I53-40B, respectively, were constructed by consensus protein design, in which multiple sequence alignments from protein families related to each protein subunit were used to guide the selection of amino acid residues at surface-exposed positions. The variant proteins were found to be more stable and soluble when purified independently than the original proteins, a property that enabled the formation of the designed nanostructure by simply mixing solutions containing the purified components in physiological buffers in a 1:1 molar ratio. The addition of 0.75% CHAPS, a zwitterionic detergent, to the buffer was found to further increase the stability and solubility of I53-40.1A and was therefore included during the purification of the protein prior to in vitro assembly. Size exclusion chromatograms from a run analyzing the mixed solution containing both components on a Superose 6 column revealed a single major peak at the elution volume expected for the 120-subunit designed icosahedral nanostructure. Analysis of the peak fractions by SDS-PAGE revealed bands at the expected molecular weight for the first and second polypeptides of the nanostructure in an apparent 1:1 stoichiometric ratio. The data demonstrate that when mixed, the two components co-assemble to the 120-subunit designed icosahedral nanostructure.

In another exemplary embodiment, the I53-47A.1, I53-47B.1, I53-50A.1, and I53-50B.1 protein variants, based off of I53-47A, I53-47B, I53-50A, and I53-50B, respectively, were constructed by consensus protein design, in which multiple sequence alignments from protein families related to each protein subunit were used to guide the selection of amino acid residues at surface-exposed positions. The variant proteins were found to be more stable and soluble when purified independently than the original proteins, a property that enabled the formation of the designed nanostructure by simply mixing solutions containing the purified components in physiological buffers in a 1:1 molar ratio, a process referred to as in vitro assembly. The addition of 0.75% CHAPS, a zwitterionic detergent, to the buffer was found to further increase the stability and solubility of I53-47B.1 and I53-50B.1 and was therefore included during the purification of the proteins prior to in vitro assembly. Size exclusion chromatograms from a run analyzing the mixed solution containing both I53-47A.1 and I53-47B.1 on a Superose 6 column revealed a major peak at the elution volume expected for the 120-subunit designed icosahedral nanostructure as well as a smaller secondary peak at a later elution volume. Analysis of the peak fractions corresponding to the 120-subunit nanostructure by SDS-PAGE revealed bands at the expected molecular weight for the first and second polypeptides of the nanostructure in an apparent 1:1 stoichiometric ratio. Analysis of the secondary peak at the later elution volume revealed that this peak comprises only the trimeric subunit, suggesting that the in vitro assembly mixture actually contained an excess of this polypeptide. Similarly, size exclusion chromatograms from a run analyzing the mixed solution containing both I53-50A.1 and I53-50B.1 on a Superose 6 column revealed a peak at the elution volume expected for the 120-subunit designed icosahedral nanostructure as well as two secondary peaks at later elution volumes. Analysis of the peak fractions corresponding to the 120-subunit nanostructure by SDS-PAGE revealed bands at the expected molecular weight for the first and second polypeptides of the nanostructure in an apparent 1:1 stoichiometric ratio. Analysis of the secondary peaks at the later elution volumes revealed that the first of the two comprises only the pentameric subunit, while the second of the two comprises only the trimeric subunit, suggesting that for this pair of proteins, in vitro assembly is somewhat inefficient. Together, the data demonstrate that when mixed, the two components of each nanostructure (i.e., I53-47A.1 and I53-47B.1 or I53-50A.1 and I53-50B.1) co-assemble to the 120-subunit designed icosahedral nanostructures.

In another exemplary embodiment, the protein variants I53-47A.1NegT2, I53-47B.1NegT2, I53-50A.1NegT2, and I53-50B.1NegT2, based off of I53-47A.1, I53-47B.1, I53-50A.1, and I53-50B.1, respectively, bear mutations that introduce additional negatively charged amino acid residues (i.e., Aspartate and Glutamate) on their surfaces such that the nanostructures formed through the assembly of these proteins have highly charged interior surfaces. After the two independently purified proteins I53-47A.1NegT2 and I53-47B.1NegT2 were mixed together in an in vitro assembly reaction in a buffer with a concentration of 150 mM NaCl, no assembly was observed when the mixture was analyzed on a Superose 6 size exclusion chromatography column; only unassembled I53-47A.1NegT2 and I53-47B.1NegT2 proteins eluted from the column. In contrast, if the in vitro assembly reaction was performed in the presence of 0.5 M NaCl, robust assembly to the designed nanostructure was observed, with some remaining unassembled proteins eluting later as smaller secondary elution peaks. Similarly, after the two independently purified proteins I53-50A.1NegT2 and I53-50B.1NegT2 were mixed together in an in vitro assembly reaction in a buffer with a concentration of 150 mM NaCl, no assembly was observed when the mixture was analyzed on a Superose® 6 size exclusion chromatography column; only unassembled I53-50A.1NegT2 and I53-50B.1NegT2 proteins eluted from the column. In contrast, if the in vitro assembly reaction was performed in the presence of 0.5 M NaCl, assembly to the designed nanostructure was observed, with some remaining unassembled proteins eluting later. Together, the data demonstrate that when mixed, the two components of each highly charged 120-subunit designed icosahedral nanostructure assemble to the target structure only in the presence of high ionic strength.

In order to package nucleic acids, pairs of individually purified protein components designed to co-assemble into a nanoparticle were combined with single-stranded DNA (ssDNA) in buffer and allowed to incubate overnight. ssDNA was present at a final concentration of 26 ng/µL (200 pM) for 400 nucleotide (nt) strands, and 35.2 ng/µL (66.7 pM) for 1600 nt strands. Individual protein components were added at final equimolar concentrations ranging from 2-12 µM, and the final NaCl concentration was 150 mM. After overnight incubation, samples were either analyzed by electrophoresis on a 1% agarose gel or DNase I was added to a final concentration of 25 µg/mL and incubated for one hour at room temperature before electrophoresis. Gels were stained with SybrGold® (ThermoFisher Scientific) and imaged to visualize nucleic acid, and were subsequently stained with GelCode® Blue (Pierce) and imaged again to visualize protein.

The above definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

The above description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Numerous modifications and variations of the present disclosure are possible in light of the above teachings. Unless otherwise indicated, all numbers expressing quantities of ingredients, properties such as molecular weight, reaction conditions, and so forth used in the specification and claims are to be understood as being modified in all instances by the term "about." Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Furthermore, numerous references have been made to patents and printed publications throughout this specification. Each of the above-cited references and printed publications are individually incorporated herein by reference in their entirety.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described. The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

REFERENCES

1. N. P. King et al., Computational design of self-assembling protein nanomaterials with atomic level accuracy. Science 336, 1171 (Jun. 1, 2012).
2. N. P. King et al., Accurate design of co-assembling multi-component protein nanomaterials. Nature 510, 103 (Jun. 5, 2014).
3. S. Raman et al., Design of Peptide Nanoparticles Using Simple Protein Oligomerization Domains. The Open Nanomedicine Journal 2, 15 (2009).
4. J. P. Julien et al., Crystal structure of a soluble cleaved HIV-1 envelope trimer. Science 342, 1477 (Dec. 20, 2013).
5. D. Lyumkis et al., Cryo-EM structure of a fully glycosylated soluble cleaved HIV-1 envelope trimer. Science 342, 1484 (Dec. 20, 2013).
6. M. Pancera et al., Structure and immune recognition of trimeric pre-fusion HIV-1 Env. Nature, (Oct. 8, 2014).
7. T. O. Yeates, C. S. Crowley, S. Tanaka, Bacterial microcompartment organelles: protein shell structure and evolution. Annu Rev Biophys 39, 185 (2010).
8. P. Kumar, M. Singh, S. Karthikeyan, Crystal structure analysis of icosahedral lumazine synthase from *Salmonella typhimurium*, an antibacterial drug target. Acta Crystallogr D Biol Crystallogr 67, 131 (February, 2011).
9. C. Jäckel, J. D. Bloom, P. Kast, F. H. Arnold, D. Hilvert. Consensus Protein Design without Phylogenetic Bias J. Mol. Biol., 399 (2010), pp. 541-546.
10. Hura, G. L. et al. Robust, high-throughput solution structural analyses by small angle X-ray scattering (SAXS). *Nat. Methods* 6, 606-612 (2009).
11. Schneidman-Duhovny, D., Hammel, M., Tainer, J. A. & Sali, A. Accurate SAXS Profile Computation and its Assessment by Contrast Variation Experiments. *Biophys. J.* 105, 962-974 (2013).
12. Schneidman-Duhovny, D., Hammel, M. & Sali, A. FoXS: a web server for rapid computation and fitting of SAXS profiles. *Nucleic Acids Res.* 38, W540-W544 (2010).

We claim:

1. An isolated polypeptide comprising an amino acid sequence that is at least 75% identical over its length, and identical at least at one identified interface position, to the amino acid sequence of a polypeptide selected from the group consisting of SEQ ID NOS:1-34:

| Name | Amino Acid Sequence | Identified interface residues |
|---|---|---|
| I53-34A SEQ ID NO: 1 | MEGMDPLAVLAESRLLPLLTVRGGE DLAGLATVLELMGVGALEITLRTEK GLEALKALRKSGLLLGAGTVRSPKE AEAALEAGAAFLVSPGLLEEVAALA QARGVPYLPGVLTPTEVERALALGL SALKFFPAEPFQGVRVLRAYAEVFP EVRFLPTGGIKEEHLPHYAALPNLL AVGGSWLLQGDLAAVMKKVKAAKAL LSPQAPG | I53-34A: 28,32,36, 37,186, 188,191, 192,195 |
| I53-34B SEQ ID NO: 2 | MTKKVGIVDTTFARVDMAEAAIRTL KALSPNIKIIRKTVPGIKDLPVACK KLLEEEGCDIVMALGMPGKAEKDKV CAHEASLGLMLAQLMTNKHIIEVFV HEDEAKDDDELDILALVRAIEHAAN VYYLLFKPEYLTRMAGKGLRQGRED AGPARE | I53-34B: 19,20,23, 24,27, 109,113, 116,117, 120,124, 148 |
| I53-40A SEQ ID NO: 3 | MTKKVGIVDTTFARVDMASAAILTL KMESPNIKIIRKTVPGIKDLPVACK KLLEEEGCDIVMALGMPGKAEKDKV CAHEASLGLMLAQLMTNKHIIEVFV HEDEAKDDAELKILAARRAIEHALN VYYLLFKPEYLTRMAGKGLRQGFED AGPARE | I53-40A: 20,23,24, 27,28, 109,112, 113,116, 120,124 |
| I53-40B SEQ ID NO: 4 | MSTINNQLKALKVIPVIAIDNAEDI IPLGKVLAENGLPAAEITFRSSAAV KAIMLLRSAQPEMLIGAGTILNGVQ ALAAKEAGATFVVSPGFNPNTVRAC QIIGIDIVPGVNNPSTVEAALEMGL TTLKFFPAEASGGISMVKSLVGPYG DIRLMPTGGITPSNIDNYLAIPQVL ACGGTWMVDKKLVTNGEWDEIARLT REIVEQVNP | I53-40B: 47,51,54, 58,74,102 |
| I53-47A SEQ ID NO: 5 | MPIFTLNTNIKATDVPSDFLSLTSR LVGLILSKPGSYVAVHINTDQQLSF GGSTNPAAFGTLMSIGGIEPSKNRD HSAVLFDHLNAMLGIPKNRMYIHFV NLNGDDVGWNGTTF | I53-47A: 22,25,29, 72,79,86, 87 |
| I53-47B SEQ ID NO: 6 | MNQHSHKDYETVRIAVVRARWHADI VDACVEAFEIAMAAIGGDRFAVDVF DVPGAYEIPLHARTLAETGRYGAVL GTAFVVNGGIYRHEFVASAVIDGMM NVQLSTGVPVLSAVLTPHRYRDSAE HHRFFAAHFAVKGVEAARACIEILA AREKIAA | I53-47B: 28,31,35, 36,39, 131,132, 135,139, 146 |
| I53-50A SEQ ID NO: 7 | MKMEELFKKHKIVAVLRANSVEEAI EKAVAVFAGGVHLIEITFTVPDADT VIKALSVLKEKGAIIGAGTVTSVEQ | I53-50A: 25,29,33, 54,57 |

| Name | Amino Acid Sequence | Identified interface residues |
|---|---|---|
| | CRKAVESGAEFIVSPHLDEEISQFC KEKGVFYMPGVMTPTELVKAMKLGH TILKLFPGEVVGPQEVKAMKGPFPN VKEVPTGGVNLDNVCEWEKAGVLAV GVGSALVKGTPDEVREKAKAFVEKI RGCTE | |
| I53-50B SEQ ID NO: 8 | MNQHSHKDYETVRIAVVRARWHAEI VDACVSAFEAAMADIGGDRFAVDVE DVPGAYEIPLHARTLAETGRYGAVL GTAFVVNGGIYRHEEVASAVIDGMM NVQLSTGVPVLSAVLTPHRYRDSDA HTLLFLALFAVKGMEAARACVEILA AREKIAA | I53-50B: 24,28,36, 124,125, 127,128, 129,131, 132,133, 135,139 |
| I53-51A SEQ ID NO: 9 | MFTKSGDDGNTNVINKRVGKDSPLV NFLGDLDELNSFIGFAISKIPWEDM KKDLERVQVELFEIGEDLSTQSSKK KIDESYVLWLLAATAIYRIESGPVK LFVIPGGSEEASVLHVTRSVARRVE RNAVKYTKELPEINRMIIVYLNRLS SLLFAMALVANKRRNQSEKIYEIGK SW | I53-51A: 80,83,86, 87,88,90, 91,94, 166,172, 176 |
| I53-51B SEQ ID NO: 10 | MNQHSHKDYETVRIAVVRARWHADI VDQCVRAFEEAMADAGGDRFAVDVE DVPGAYEIPLHARTLAETGRYGAVL GTAFVVNGGIYRHEFVASAVIDGMM NVQLSTGVPVLSAVLTPHRYRSSRE HHEFFREHFMVKGVEAAAACITILA AREKIAA | I53-51B: 31,35,36, 40,122, 124,128, 131,135, 139,143, 146,147 |
| I52-03A SEQ ID NO: 11 | MGHTKGPTPQQHDGSALRIGWHARW NKTIIMPLLIGTIAKLLECGVKASN IVVQSVPGSWELPIAVQRLYSASQL QTPSSGPSLSAGDLLGSSTTDLTAL PTTTASSTGPFDALIAIGVLIKGET MHFEYIADSVSHGLMRVQLDTGVPV IFGVLTVLTDDQAKARAGVIEGSHN HGEDWGLAAVEMGVRRRDWAAGKTE | I52-03A: 28,32,36, 39,44,49 |
| I52-03B SEQ ID NO: 12 | MYEVDHADVYDLFYLGRGKDYAAEA SDIADLVRSRTPEASSLLDVACGTG THLEHFTKEFGDTAGLELSEDMLTH ARKRLPDATLHQGDMRDFQLGRKFS AVVSMFSSVGYLKTVAELGAAVASF AEHLEPGGVVVVEPWWFPETFADGW VSADVVRRDGRTVARVSHSVREGNA TRMEVHFTVADPGKGVRHFSDVHLI TLFHQREYEAAFMAAGLRVEYLEGG PSGRGLFVGVPA | I52-03B: 94,115, 116,206, 213 |
| I52-32A SEQ ID NO: 13 | MGMKEKFVLIITHGDFGKGLLSGAE VIIGKQENVHTVGLNLGDNIEKVAK EVMRIIIAKLAEDKEIIIVVDLFGG SPFNIALEMMKTFDVKVITGINMPM LVELLTSINVYDTTELLENISKIGK DGIKVIEKSSLKM | I52-32A: 47,49,53, 54,57,58, 61,83,87, 88 |
| I52-32B SEQ ID NO: 14 | MKYDGSKLRIGILHARWNLEIIAAL VAGAIKRLQEFGVKAENIIIETVPG SFELPYGSKLFVEKQKRLGKPLDAI IPIGVLIKGSTMHFEYICDSTTHQL MKLNFELGIPVIFGVLTCLTDEQAE ARAGLIEGKMHNHGEDWGAAAVEMA TKFN | I52-32B: 19,20,23, 30,40 |
| I52-33A SEQ ID NO: 15 | MAVKGLGEVDQKYDGSKLRIGILHA RWNRKIILALVAGAVLRLLEFGVKA ENIIIETVPGSFELPYGSKLFVEKQ KRLGKPLDAIIPIGVLIKGSTMHFE YICDSTTHQLMKLNFELGIPVIFGV LTCLTDEQAERAGLIEGKMHNHGE DWGAAAVEMATKFN | I52-33A: 33,41,44, 50 |
| I52-33B SEQ ID NO: 16 | MGANWYLDNESSRLSFTSTKNADIA EVHRFLVLHGKVDPKGLAEVEVETE SISTGIPLRDMLLRVLVFQVSKFPV AQINAQLDMRPINNLAPGAQLELRL PLTVSLRGKSHSYNAELLATRLDER RFQVVTLEPLVIHAQDFDMVRAFNA LRLVAGLSAVSLSVPVGAVLIFTAR | I52-33B: 61,63,66, 67,72, 147,148, 154,155 |
| I32-06A SEQ ID NO: 17 | MTDYIRDGSAIKALSFAIILAEADL RHIPQDLQRLAVRVIHACGMVDVAN DLAFSEGAGKAGRNALLAGAPILCD ARMVAEGITRSRLPADNRVIYTLSD PSVPELAKKIGNTRSAAALDLWLPH IEGSIVAIGNAPTALFRLFELLDAG APKPALIIGMPVGFVGAAESKDELA ANSRGVPYVIVRGRRGGSAMTAAAV NALASERE | I32-06A: 9,12,13, 14,20,30, 33,34 |
| I32-06B SEQ ID NO: 18 | MITVFGLKSKLAPRREKLAEVIYSS LHLGLDIPKGKHAIRFLCLEKEDFY YPFDRSDDYTVIEINLMAGRSEETK MLLIFLLFIALERKLGIRAHDVEIT IKEQPAHCWGFRGRTGDSARDLDYD IYV | I32-06B: 24,71,73, 76,77,80, 81,84,85, 88,114, 118 |
| I32-19A SEQ ID NO: 19 | MGSDLQKLQRFSTCDISDGLLNVYN IPTGGYFPNLTAISPPQNSSIVGTA YTVLFAPIDDPRPAVNYIDSVPPNS ILVLALEPHLQSQFHPFIKITQAMY GGLMSTRAQYLKSNGTVVFGRIRDV DEHRTLNHPVFAYGVGSCAPKAVVK AVGTNVQLKILTSDGVTQTICPGDY IAGDNNGIVRIPVQETDISKLVTYI EKSIEVDRLVSEAIKNGLPAKAQT ARRMVLKDYI | I32-19A: 208,213, 218,222, 225,226, 229,233 |
| I32-19B SEQ ID NO: 20 | MSGMRVYLGADHAGYELKQAIIAFL KMTGHEPIDCGALRYDADDDYPAFC IAAATRTVADPGSLGIVLGGSGNGE QIAANKVPGARCALAWSVQTAALAR EHNNAQLIGIGGRMHTLEEALRIVK AFVTTPWSKAQRHQRRIDILAEYER THEAPPVPGAPA | I32-19B: 20,23,24, 27,117, 118,122, 125 |
| I32-28A SEQ ID NO: 21 | MGDDARIAAIGDVDELNSQIGVLLA EPLPDDVRAALSAIQHDLFDLGGEL CIPGHAAITEDHLLRLALWLVHYNG QLPPLEEFILPGGARGAALAHVCRT VCRRAERSIKALGASEPLNIAPAAY VNLLSDLLFVLARVLNRAAGGADVL WDRTRAH | I32-28A: 60,61,64, 67,68,71, 110,120, 123,124, 128 |
| I32-28B SEQ ID NO: 22 | MILSAEQSFTLRHPHGQAAALAFVR EPAAALAGVQRLRGLDSDGEQVWGE LLVRVPLLGEVDLPFRSEIVRTPQG AELRPLTLTGERAWVAVSGQATAAE GGEMAFAFQFQAHLATPEAEGEGGA AFEVMVQAAAGVTLLLVAMALPQGL AAGLPPA | I32-28B: 35,36,54, 122,129, 137,140, 141,144, 148 |
| I53-40A.1 SEQ ID NO: 23 | MTKKVGIVDTTFARVDMASAAILTL KMESPNIKIIRKTVPGIKDLPVACK KLLEEEGCDIVMALGMPGKKEKDKV CAHEASLGLMLAQLMTNKHIIEVFV HEDEAKDDAELKILAARRAIEHALN VYYLLFKPEYLTRMAGKGLRQGFED AGPARE | I53-40A: 20,23,24, 27,28, 109,112, 113,116, 120,124 |
| I53-40B.1 SEQ ID NO: 24 | MDDINNQLKRLKVIPVIAIDNAEDI IPLGKVLAENGLPAAEITERSSAAV KAIMLLRSAQPEMLIGAGTILNGVQ ALAAKEAGADFVVSPGFNPNTVRAC QIIGIDIVPGVNNPSTVEQALEMGL TTLKFFPAEASGGISMVKSLVGPYG DIRLMPTGGITPDNIDNYLAIPQVL | I53-40B: 47,51,54, 58,74,102 |

-continued

| Name | Amino Acid Sequence | Identified interface residues |
|---|---|---|
| | ACGGTWMVDKKLVRNGEWDEIARLT REIVEQVNP | |
| I53-47A.1 SEQ ID NO: 25 | MPIFTLNTNIKADDVPSDFLSLTSR LVGLILSKPGSYVAVHINTDQQLSF GGSTNPAAFGTLMSIGGIEPDKNRD HSAVLFDHLNAMLGIPKNRMYIHFV NLNGDDVGWNGTTF | I53-47A: 22,25,29, 72,79,86, 87 |
| I53-47A.1 NegT2 SEQ ID NO: 26 | MPIFTLNTNIKADDVPSDFLSLTSR LVGLILSEPGSYVAVHINTDQQLSF GGSTNPAAFGTLMSIGGIEPDKNED HSAVLFDHLNAMLGIPKNRMYIHFV DLDGDDVGWNGTTF | I53-47A: 22,25,29, 72,79,86, 87 |
| I53-47B.1 SEQ ID NO: 27 | MNQHSHKDHETVRIAVVRARWHADI VDACVEAFEIAMAAIGGDRFAVDVF DVPGAYEIPLHARTLAETGRYGAVL GTAFVVNGGIYRHEFVASAVIDGMM NVQLDTGVPVLSAVLTPHRYRDSDE HHRFFAAHFAVKGVEAARACIEILN AREKIAA | I53-47B: 28,31,35, 36,39, 131,132, 135,139, 146 |
| I53-47B.1 NegT2 SEQ ID NO: 28 | MNQHSHKDHETVRIAVVRARWHADI VDACVEAFEIAMAAIGGDRFAVDVE DVPGAYEIPLHARTLAETGRYGAVL GTAFVVDGGIYDHEEVASAVIDGMM NVQLDTGVPVLSAVLTPHEYEDSDE DHEFFAAHFAVKGVEAARACIEILN AREKIAA | I53-47B: 28,31,35, 36,39, 131,132, 135,139, 146 |
| I53-50A.1 SEQ ID NO: 29 | MKMEELFKKHKIVAVLRANSVEEAI EKAVAVFAGGVHLIEITFTVPDADT VIKALSVLKEKGAIIGAGTVTSVEQ CRKAVESGAEFIVSPHLDEEISQFC KEKGVFYMPGVMTPTELVKAMKLGH DILKLFPGEVVGPQFVKAMKGPFPN VKFVPTGGVNLDNVCEWFKAGVLAV GVGDALVKGDPDEVREKAKKFVEKI RGCTE | I53-50A: 25,29,33, 54,57 |
| I53-50A.1 NegT2 SEQ ID NO: 30 | MKMEELFKKHKIVAVLRANSVEEAI EKAVAVFAGGVHLIEITFTVPDADT VIKALSVLKEKGAIIGAGTVTSVEQ CRKAVESGAEFIVSPHLDEEISQFC KEKGVFYMPGVMTPTELVKAMKLGH DILKLFPGEVVGPEFVEAMKGPFPN VKFVPTGGVDLDDVCEWFDAGVLAV GVGDALVEGDPDEVREDAKEFVEEI RGCTE | I53-50A: 25,29,33, 54,57 |
| I53-50A.1 PosT1 SEQ ID NO: 31 | MKMEELFKKHKIVAVLRANSVEEAI EKAVAVFAGGVHLIEITFTVPDADT VIKALSVLKEKGAIIGAGTVTSVEQ CRKAVESGAEFIVSPHLDEEISQFC KEKGVFYMPGVMTPTELVKAMKLGH DILKLFPGEVVGPQFVKAMKGPFPN VKFVPTGGVNLDNVCKWFKAGVLAV GVGKALVKGKPDEVREKAKKFVKKI RGCTE | I53-50A: 25,29,33, 54,57 |
| I53-50B.1 SEQ ID NO: 32 | MNQHSHKDHETVRIAVVRARWHAEI VDACVSAFEAAMRDIGGDRFAVDVF DVPGAYEIPLHARTLAETGRYGAVL GTAFVVNGGIYRHEFVASAVIDGMM NVQLDTGVPVLSAVLTPHRYRDSDA HTLLFLALFAVKGMEAARACVEILA AREKIAA | I53-50B: 24,28,36, 124,125, 127,128, 129,131, 132,133, 135,139 |
| I53-50B.1 NegT2 SEQ ID NO: 33 | MNQHSHKDHETVRIAVVRARWHAEI VDACVSAFEAAMRDIGGDRFAVDVF DVPGAYEIPLHARTLAETGRYGAVL GTAFVVDGGIYDHEFVASAVIDGMM NVQLDTGVPVLSAVLTPHEYEDSDA | I53-50B: 24,28,36, 124,125, 127,128, 129,131, |

-continued

| Name | Amino Acid Sequence | Identified interface residues |
|---|---|---|
| | DTLLFLALFAVKGMEAARACVEILA AREKIAA | 132,133, 135,139 |
| I53-50B.4 Pos1 SEQ ID NO: 34 | MNQHSHKDHETVRIAVVRARWHAEI VDACVSAFEAAMRDIGGDRFTAVDV FDVPGAYEIPLHARTLAETGRYGAV LGTAFVVNGGIYRHEFVASAVINGM MNVQLNTGVPVLSAVLTPHNYDKSK AHTLLFLALFAVKGMEAARACVEIL AAREKIAA | I53-50B: 24,28,36, 124,125, 127,128, 129,131, 132,133, 135,139 |

2. The isolated polypeptide of claim 1, wherein the polypeptide is identical at least at half of the identified interface positions to the amino acid sequence of a polypeptide selected from the group consisting of SEQ ID NO:1-34.

3. The isolated polypeptide of claim 1, wherein the polypeptide is identical at all of the identified interface positions to the amino acid sequence of a polypeptide selected from the group consisting of SEQ ID NO:1-34.

4. The isolated polypeptide of claim 1, wherein the polypeptide comprises an amino acid sequence that is at least 90% identical over its length to the sequence of a polypeptide selected from the group consisting of SEQ ID NO:1-34.

5. The isolated polypeptide of claim 1, wherein the polypeptide comprises the amino acid sequence of a polypeptide selected from the group consisting of SEQ ID NOS: 1-40.

6. A nanostructure, comprising:
(a) a plurality of first assemblies, each first assembly comprising a plurality of identical first polypeptides, wherein the first polypeptides comprise the polypeptide of claim 1; and
(b) a plurality of second assemblies, each second assembly comprising a plurality of identical second polypeptides, wherein the second polypeptides comprise the polypeptide of claim 1, and wherein the second polypeptide differs from the first polypeptide;
wherein the plurality of first assemblies non-covalently interact with the plurality of second assemblies to form a nanostructure.

7. The nanostructure of claim 6, wherein the nanostructure has icosahedral symmetry.

8. The nanostructure of claim 6, wherein the first polypeptides and the second polypeptides comprise polypeptides with the amino acid sequences selected from the following pairs:
(i) SEQ ID NO:1 and SEQ ID NO:2 (I53-34A and I53-34B);
(ii) SEQ ID NO:3 and SEQ ID NO:4 (I53-40A and I53-40B);
(iii) SEQ ID NO:3 and SEQ ID NO:24 (I53-40A and I53-40B.1);
(iv) SEQ ID NO:23 and SEQ ID NO:4 (I53-40A.1 and I53-40B);
(v) SEQ ID NO:35 and SEQ ID NO:36 (I53-40A genus and I53-40B genus);
(vi) SEQ ID NO:5 and SEQ ID NO:6 (I53-47A and I53-47B);
(vii) SEQ ID NO:5 and SEQ ID NO:27 (I53-47A and I53-47B.1);

(viii) SEQ ID NO:5 and SEQ ID NO:28 (I53-47A and I53-47B.1NegT2);
(ix) SEQ ID NO:25 and SEQ ID NO:6 (I53-47A.1 and I53-47B);
(x) SEQ ID NO:25 and SEQ ID NO:27 (I53-47A.1 and I53-47B.1);
(xi) SEQ ID NO:25 and SEQ ID NO:28 (I53-47A.1 and I53-47B.1NegT2);
(xii) SEQ ID NO:26 and SEQ ID NO:6 (I53-47A.1NegT2 and I53-47B);
(xiii) SEQ ID NO:26 and SEQ ID NO:27 (I53-47A.1NegT2 and I53-47B.1);
(xiv) SEQ ID NO:26 and SEQ ID NO:28 (I53-47A.1NegT2 and I53-47B.1NegT2);
(xv) SEQ ID NO:37 and SEQ ID NO:38 (I53-47A genus and I53-47B genus);
(xvi) SEQ ID NO:7 and SEQ ID NO:8 (I53-50A and I53-50B);
(xvii) SEQ ID NO:7 and SEQ ID NO:32 (I53-50A and I53-50B.1);
(xix) SEQ ID NO:7 and SEQ ID NO:33 (I53-50A and I53-50B.1NegT2);
(xx) SEQ ID NO:7 and SEQ ID NO:34 (I53-50A and I53-50B.4PosT1);
(xxi) SEQ ID NO:29 and SEQ ID NO:8 (I53-50A.1 and I53-50B);
(xxii) SEQ ID NO:29 and SEQ ID NO:32 (I53-50A.1 and I53-50B.1);
(xxiii) SEQ ID NO:29 and SEQ ID NO:33 (I53-50A.1 and I53-50B.1NegT2);
(xxiv) SEQ ID NO:29 and SEQ ID NO:34 (I53-50A.1 and I53-50B.4PosT1);
(xxv) SEQ ID NO:30 and SEQ ID NO:8 (I53-50A.1NegT2 and I53-50B);
(xxvi) SEQ ID NO:30 and SEQ ID NO:32 (I53-50A.1NegT2 and I53-50B.1);
(xxvii) SEQ ID NO:30 and SEQ ID NO:33 (I53-50A.1NegT2 and I53-50B.1NegT2);
(xxviii) SEQ ID NO:30 and SEQ ID NO:34 (I53-50A.1NegT2 and I53-50B.4PosT1);
(xxix) SEQ ID NO:31 and SEQ ID NO:8 (I53-50A.1PosT1 and I53-50B);
(xxx) SEQ ID NO:31 and SEQ ID NO:32 (I53-50A.1PosT1 and I53-50B.1);
(xxxi) SEQ ID NO:31 and SEQ ID NO:33 (I53-50A.1PosT1 and I53-50B.1NegT2);
(xxxii) SEQ ID NO:31 and SEQ ID NO:34 (I53-50A.1PosT1 and I53-50B.4PosT1);
(xxxiii) SEQ ID NO:39 and SEQ ID NO:40 (I53-50A genus and I53-50B genus);
(xxxiv) SEQ ID NO:9 and SEQ ID NO:10 (I53-51A and I53-51B);
(xxxv) SEQ ID NO:11 and SEQ ID NO:12 (I52-03A and I52-03B);
(xxxvi) SEQ ID NO:13 and SEQ ID NO:14 (I52-32A and I52-32B);
(xxxv) SEQ ID NO:15 and SEQ ID NO:16 (I52-33A and I52-33B)
(xxxvi) SEQ ID NO:17 and SEQ ID NO:18 (I32-06A and I32-06B);
(xxxvii) SEQ ID NO:19 and SEQ ID NO:20 (I32-19A and I32-19B);
(xxxviii) SEQ ID NO:21 and SEQ ID NO:22 (I32-28A and I32-28B); and
(xxxix) SEQ ID NO:23 and SEQ ID NO:24 (I53-40A.1 and I53-40B.1).

9. The nanostructure of claim 6, wherein the number of identical first polypeptides in each first assembly is different than the number of identical second polypeptides in each second assembly.

10. The nanostructure of claim 9, wherein each first assembly comprises five copies of the identical first polypeptide, and each second assembly comprises three copies of the identical second polypeptide.

11. The nanostructure of claim 10, wherein the nanostructure comprises twelve first assemblies and twenty second assemblies.

12. The nanostructure of claim 9, wherein each first assembly comprises three copies of the identical first polypeptide, and each second assembly comprises two copies of the identical second polypeptide.

13. The nanostructure of claim 12, wherein the nanostructure comprises twenty first assemblies and thirty second assemblies.

14. The nanostructure of claim 9, wherein each first assembly comprises five copies of the identical first polypeptide, and each second assembly comprises two copies of the identical second polypeptide.

15. The nanostructure of claim 14, wherein the nanostructure comprises twelve first assemblies and thirty second assemblies.

16. The nanostructure of claim 6, further comprising a cargo within the nanostructure.

17. The nanostructure of claim 16, wherein the cargo comprises a nucleic acid.

* * * * *

SEQUENCE LISTING

<160> NUMBER OF SEQ ID NOS: 43

<210> SEQ ID NO 1
<211> LENGTH: 207
<212> TYPE: PRT
<213> ORGANISM: Artificial Sequence
<220> FEATURE:
<223> OTHER INFORMATION: Synthetic

<400> SEQUENCE: 1

Met Glu Gly Met Asp Pro Leu Ala Val Leu Ala Glu Ser Arg Leu Leu
1               5                   10                  15

Pro Leu Leu Thr Val Arg Gly Gly Glu Asp Leu Ala Gly Leu Ala Thr
                20                  25                  30

Val Leu Glu Leu Met Gly Val Gly Ala Leu Glu Ile Thr Leu Arg Thr
            35                  40                  45

Glu Lys Gly Leu Glu Ala Leu Lys Ala Leu Arg Lys Ser Gly Leu Leu
        50                  55                  60

Leu Gly Ala Gly Thr Val Arg Ser Pro Lys Glu Ala Glu Ala Ala Leu
65                  70                  75                  80

Glu Ala Gly Ala Ala Phe Leu Val Ser Pro Gly Leu Leu Glu Glu Val
                85                  90                  95

Ala Ala Leu Ala Gln Ala Arg Gly Val Pro Tyr Leu Pro Gly Val Leu
            100                 105                 110

Thr Pro Thr Glu Val Glu Arg Ala Leu Ala Leu Gly Leu Ser Ala Leu
        115                 120                 125

Lys Phe Phe Pro Ala Glu Pro Phe Gln Gly Val Arg Val Leu Arg Ala
    130                 135                 140

Tyr Ala Glu Val Phe Pro Glu Val Arg Phe Leu Pro Thr Gly Gly Ile
145                 150                 155                 160

Lys Glu Glu His Leu Pro His Tyr Ala Ala Leu Pro Asn Leu Leu Ala
                165                 170                 175

Val Gly Gly Ser Trp Leu Leu Gln Gly Asp Leu Ala Ala Val Met Lys
            180                 185                 190

Lys Val Lys Ala Ala Lys Ala Leu Leu Ser Pro Gln Ala Pro Gly
        195                 200                 205

<210> SEQ ID NO 2
<211> LENGTH: 156
<212> TYPE: PRT
<213> ORGANISM: Artificial Sequence
<220> FEATURE:
<223> OTHER INFORMATION: Synthetic

<400> SEQUENCE: 2

Met Thr Lys Lys Val Gly Ile Val Asp Thr Thr Phe Ala Arg Val Asp
1               5                   10                  15

Met Ala Glu Ala Ala Ile Arg Thr Leu Lys Ala Leu Ser Pro Asn Ile
                20                  25                  30

Lys Ile Ile Arg Lys Thr Val Pro Gly Ile Lys Asp Leu Pro Val Ala
            35                  40                  45

Cys Lys Lys Leu Leu Glu Glu Gly Cys Asp Ile Val Met Ala Leu
        50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Asp Asp Glu Leu Asp
            100                 105                 110

Ile Leu Ala Leu Val Arg Ala Ile Glu His Ala Ala Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Arg Glu Asp Ala Gly Pro Ala Arg Glu
145                 150                 155

<210> SEQ ID NO 3
<211> LENGTH: 156
<212> TYPE: PRT
<213> ORGANISM: Artificial Sequence
<220> FEATURE:
<223> OTHER INFORMATION: Synthetic

<400> SEQUENCE: 3

```
Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Gly Cys Asp Ile Val Met Ala Leu
    50                  55                  60

Gly Met Pro Gly Lys Ala Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155
```

<210> SEQ ID NO 4
<211> LENGTH: 209
<212> TYPE: PRT
<213> ORGANISM: Artificial Sequence
<220> FEATURE:
<223> OTHER INFORMATION: Synthetic

<400> SEQUENCE: 4

```
Met Ser Thr Ile Asn Asn Gln Leu Lys Ala Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Thr Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Ala Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
```

```
            145                 150                 155                 160
Thr Pro Ser Asn Ile Asp Asn Tyr Leu Ala Ile Pro Gln Val Leu Ala
                165                 170                 175

Cys Gly Gly Thr Trp Met Val Asp Lys Lys Leu Val Thr Asn Gly Glu
                180                 185                 190

Trp Asp Glu Ile Ala Arg Leu Thr Arg Glu Ile Val Glu Gln Val Asn
            195                 200                 205

Pro

<210> SEQ ID NO 5
<211> LENGTH: 114
<212> TYPE: PRT
<213> ORGANISM: Artificial Sequence
<220> FEATURE:
<223> OTHER INFORMATION: Synthetic

<400> SEQUENCE: 5

Met Pro Ile Phe Thr Leu Asn Thr Asn Ile Lys Ala Thr Asp Val Pro
1               5                   10                  15

Ser Asp Phe Leu Ser Leu Thr Ser Arg Leu Val Gly Leu Ile Leu Ser
                20                  25                  30

Lys Pro Gly Ser Tyr Val Ala Val His Ile Asn Thr Asp Gln Gln Leu
            35                  40                  45

Ser Phe Gly Gly Ser Thr Asn Pro Ala Ala Phe Gly Thr Leu Met Ser
        50                  55                  60

Ile Gly Gly Ile Glu Pro Ser Lys Asn Arg Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Asn Leu Asn Gly Asp Asp Val Gly Trp Asn Gly Thr
            100                 105                 110

Thr Phe

<210> SEQ ID NO 6
<211> LENGTH: 157
<212> TYPE: PRT
<213> ORGANISM: Artificial Sequence
<220> FEATURE:
<223> OTHER INFORMATION: Synthetic

<400> SEQUENCE: 6

Met Asn Gln His Ser His Lys Asp Tyr Glu Thr Val Arg Ile Ala Val
1               5                   10                  15

Val Arg Ala Arg Trp His Ala Asp Ile Val Asp Ala Cys Val Glu Ala
                20                  25                  30

Phe Glu Ile Ala Met Ala Ala Ile Gly Gly Asp Arg Phe Ala Val Asp
            35                  40                  45

Val Phe Asp Val Pro Gly Ala Tyr Glu Ile Pro Leu His Ala Arg Thr
        50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Ser Thr Gly Val Pro Val Leu Ser
            100                 105                 110

Ala Val Leu Thr Pro His Arg Tyr Arg Asp Ser Ala Glu His His Arg
        115                 120                 125
```

```
Phe Phe Ala Ala His Phe Ala Val Lys Gly Val Glu Ala Ala Arg Ala
    130                 135                 140

Cys Ile Glu Ile Leu Ala Ala Arg Glu Lys Ile Ala Ala
145                 150                 155
```

<210> SEQ ID NO 7
<211> LENGTH: 205
<212> TYPE: PRT
<213> ORGANISM: Artificial Sequence
<220> FEATURE:
<223> OTHER INFORMATION: Synthetic

<400> SEQUENCE: 7

```
Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
                180                 185                 190

Ala Lys Ala Phe Val Glu Lys Ile Arg Gly Cys Thr Glu
            195                 200                 205
```

<210> SEQ ID NO 8
<211> LENGTH: 157
<212> TYPE: PRT
<213> ORGANISM: Artificial Sequence
<220> FEATURE:
<223> OTHER INFORMATION: Synthetic

<400> SEQUENCE: 8

```
Met Asn Gln His Ser His Lys Asp Tyr Glu Thr Val Arg Ile Ala Val
1               5                   10                  15

Val Arg Ala Arg Trp His Ala Glu Ile Val Asp Ala Cys Val Ser Ala
                20                  25                  30

Phe Glu Ala Ala Met Ala Asp Ile Gly Gly Asp Arg Phe Ala Val Asp
            35                  40                  45

Val Phe Asp Val Pro Gly Ala Tyr Glu Ile Pro Leu His Ala Arg Thr
        50                  55                  60

Leu Ala Glu Thr Gly Arg Tyr Gly Ala Val Leu Gly Thr Ala Phe Val
```

```
                65                  70                  75                  80
Val Asn Gly Gly Ile Tyr Arg His Glu Phe Val Ala Ser Ala Val Ile
                    85                  90                  95

Asp Gly Met Met Asn Val Gln Leu Ser Thr Gly Val Pro Val Leu Ser
                100                 105                 110

Ala Val Leu Thr Pro His Arg Tyr Arg Asp Ser Asp Ala His Thr Leu
                115                 120                 125

Leu Phe Leu Ala Leu Phe Ala Val Lys Gly Met Glu Ala Ala Arg Ala
            130                 135                 140

Cys Val Glu Ile Leu Ala Ala Arg Glu Lys Ile Ala Ala
145                 150                 155

<210> SEQ ID NO 9
<211> LENGTH: 177
<212> TYPE: PRT
<213> ORGANISM: Artificial Sequence
<220> FEATURE:
<223> OTHER INFORMATION: Synthetic

<400> SEQUENCE: 9

Met Phe Thr Lys Ser Gly Asp Asp Gly Asn Thr Asn Val Ile Asn Lys
1               5                   10                  15

Arg Val Gly Lys Asp Ser Pro Leu Val Asn Phe Leu Gly Asp Leu Asp
                20                  25                  30

Glu Leu Asn Ser Phe Ile Gly Phe Ala Ile Ser Lys Ile Pro Trp Glu
            35                  40                  45

Asp Met Lys Lys Asp Leu Glu Arg Val Gln Val Glu Leu Phe Glu Ile
        50                  55                  60

Gly Glu Asp Leu Ser Thr Gln Ser Ser Lys Lys Ile Asp Glu Ser
65                  70                  75                  80

Tyr Val Leu Trp Leu Leu Ala Ala Thr Ala Ile Tyr Arg Ile Glu Ser
                85                  90                  95

Gly Pro Val Lys Leu Phe Val Ile Pro Gly Gly Ser Glu Glu Ala Ser
                100                 105                 110

Val Leu His Val Thr Arg Ser Val Ala Arg Arg Val Glu Arg Asn Ala
                115                 120                 125

Val Lys Tyr Thr Lys Glu Leu Pro Glu Ile Asn Arg Met Ile Ile Val
            130                 135                 140

Tyr Leu Asn Arg Leu Ser Ser Leu Leu Phe Ala Met Ala Leu Val Ala
145                 150                 155                 160

Asn Lys Arg Arg Asn Gln Ser Glu Lys Ile Tyr Glu Ile Gly Lys Ser
                165                 170                 175

Trp

<210> SEQ ID NO 10
<211> LENGTH: 157
<212> TYPE: PRT
<213> ORGANISM: Artificial Sequence
<220> FEATURE:
<223> OTHER INFORMATION: Synthetic

<400> SEQUENCE: 10

Met Asn Gln His Ser His Lys Asp Tyr Glu Thr Val Arg Ile Ala Val
1               5                   10                  15

Val Arg Ala Arg Trp His Ala Asp Ile Val Asp Gln Cys Val Arg Ala
                20                  25                  30

Phe Glu Glu Ala Met Ala Asp Ala Gly Gly Asp Arg Phe Ala Val Asp
```

```
                    35                  40                  45
Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asn Gly Gly Ile Tyr Arg His Glu Phe Val Ala Ser Ala Val Ile
                 85                  90                  95

Asp Gly Met Met Asn Val Gln Leu Ser Thr Gly Val Pro Val Leu Ser
                100                 105                 110

Ala Val Leu Thr Pro His Arg Tyr Arg Ser Ser Arg Glu His His Glu
                115                 120                 125

Phe Phe Arg Glu His Phe Met Val Lys Gly Val Glu Ala Ala Ala Ala
                130                 135                 140

Cys Ile Thr Ile Leu Ala Ala Arg Glu Lys Ile Ala Ala
145                 150                 155

<210> SEQ ID NO 11
<211> LENGTH: 201
<212> TYPE: PRT
<213> ORGANISM: Artificial Sequence
<220> FEATURE:
<223> OTHER INFORMATION: Synthetic

<400> SEQUENCE: 11

Met Gly His Thr Lys Gly Pro Thr Pro Gln Gln His Asp Gly Ser Ala
 1               5                  10                  15

Leu Arg Ile Gly Ile Val His Ala Arg Trp Asn Lys Thr Ile Ile Met
                20                  25                  30

Pro Leu Leu Ile Gly Thr Ile Ala Lys Leu Leu Glu Cys Gly Val Lys
                35                  40                  45

Ala Ser Asn Ile Val Val Gln Ser Val Pro Gly Ser Trp Glu Leu Pro
 50                  55                  60

Ile Ala Val Gln Arg Leu Tyr Ser Ala Ser Gln Leu Gln Thr Pro Ser
 65                  70                  75                  80

Ser Gly Pro Ser Leu Ser Ala Gly Asp Leu Leu Gly Ser Ser Thr Thr
                85                  90                  95

Asp Leu Thr Ala Leu Pro Thr Thr Ala Ser Ser Thr Gly Pro Phe
                100                 105                 110

Asp Ala Leu Ile Ala Ile Gly Val Leu Ile Lys Gly Glu Thr Met His
                115                 120                 125

Phe Glu Tyr Ile Ala Asp Ser Val Ser His Gly Leu Met Arg Val Gln
                130                 135                 140

Leu Asp Thr Gly Val Pro Val Ile Phe Gly Val Leu Thr Val Leu Thr
145                 150                 155                 160

Asp Asp Gln Ala Lys Ala Arg Ala Gly Val Ile Glu Gly Ser His Asn
                165                 170                 175

His Gly Glu Asp Trp Gly Leu Ala Ala Val Glu Met Gly Val Arg Arg
                180                 185                 190

Arg Asp Trp Ala Ala Gly Lys Thr Glu
                195                 200

<210> SEQ ID NO 12
<211> LENGTH: 237
<212> TYPE: PRT
<213> ORGANISM: Artificial Sequence
<220> FEATURE:
<223> OTHER INFORMATION: Synthetic
```

<400> SEQUENCE: 12

Met Tyr Glu Val Asp His Ala Asp Val Tyr Asp Leu Phe Tyr Leu Gly
1               5                   10                  15

Arg Gly Lys Asp Tyr Ala Ala Glu Ala Ser Asp Ile Ala Asp Leu Val
            20                  25                  30

Arg Ser Arg Thr Pro Glu Ala Ser Ser Leu Leu Asp Val Ala Cys Gly
        35                  40                  45

Thr Gly Thr His Leu Glu His Phe Thr Lys Glu Phe Gly Asp Thr Ala
    50                  55                  60

Gly Leu Glu Leu Ser Glu Asp Met Leu Thr His Ala Arg Lys Arg Leu
65                  70                  75                  80

Pro Asp Ala Thr Leu His Gln Gly Asp Met Arg Asp Phe Gln Leu Gly
                85                  90                  95

Arg Lys Phe Ser Ala Val Val Ser Met Phe Ser Ser Val Gly Tyr Leu
            100                 105                 110

Lys Thr Val Ala Glu Leu Gly Ala Ala Val Ala Ser Phe Ala Glu His
        115                 120                 125

Leu Glu Pro Gly Gly Val Val Val Glu Pro Trp Trp Phe Pro Glu
    130                 135                 140

Thr Phe Ala Asp Gly Trp Val Ser Ala Asp Val Val Arg Arg Asp Gly
145                 150                 155                 160

Arg Thr Val Ala Arg Val Ser His Ser Val Arg Glu Gly Asn Ala Thr
                165                 170                 175

Arg Met Glu Val His Phe Thr Val Ala Asp Pro Gly Lys Gly Val Arg
            180                 185                 190

His Phe Ser Asp Val His Leu Ile Thr Leu Phe His Gln Arg Glu Tyr
        195                 200                 205

Glu Ala Ala Phe Met Ala Ala Gly Leu Arg Val Glu Tyr Leu Glu Gly
    210                 215                 220

Gly Pro Ser Gly Arg Gly Leu Phe Val Gly Val Pro Ala
225                 230                 235

<210> SEQ ID NO 13
<211> LENGTH: 138
<212> TYPE: PRT
<213> ORGANISM: Artificial Sequence
<220> FEATURE:
<223> OTHER INFORMATION: Synthetic

<400> SEQUENCE: 13

Met Gly Met Lys Glu Lys Phe Val Leu Ile Ile Thr His Gly Asp Phe
1               5                   10                  15

Gly Lys Gly Leu Leu Ser Gly Ala Glu Val Ile Ile Gly Lys Gln Glu
            20                  25                  30

Asn Val His Thr Val Gly Leu Asn Leu Gly Asp Asn Ile Glu Lys Val
        35                  40                  45

Ala Lys Glu Val Met Arg Ile Ile Ala Lys Leu Ala Glu Asp Lys
    50                  55                  60

Glu Ile Ile Ile Val Val Asp Leu Phe Gly Gly Ser Pro Phe Asn Ile
65                  70                  75                  80

Ala Leu Glu Met Met Lys Thr Phe Asp Val Lys Val Ile Thr Gly Ile
                85                  90                  95

Asn Met Pro Met Leu Val Glu Leu Leu Thr Ser Ile Asn Val Tyr Asp
            100                 105                 110

Thr Thr Glu Leu Leu Glu Asn Ile Ser Lys Ile Gly Lys Asp Gly Ile
            115                 120                 125

Lys Val Ile Glu Lys Ser Ser Leu Lys Met
        130                 135

<210> SEQ ID NO 14
<211> LENGTH: 154
<212> TYPE: PRT
<213> ORGANISM: Artificial Sequence
<220> FEATURE:
<223> OTHER INFORMATION: Synthetic

<400> SEQUENCE: 14

Met Lys Tyr Asp Gly Ser Lys Leu Arg Ile Gly Ile Leu His Ala Arg
1               5                   10                  15

Trp Asn Leu Glu Ile Ile Ala Ala Leu Val Ala Gly Ala Ile Lys Arg
            20                  25                  30

Leu Gln Glu Phe Gly Val Lys Ala Glu Asn Ile Ile Glu Thr Val
        35                  40                  45

Pro Gly Ser Phe Glu Leu Pro Tyr Gly Ser Lys Leu Phe Val Glu Lys
    50                  55                  60

Gln Lys Arg Leu Gly Lys Pro Leu Asp Ala Ile Pro Ile Gly Val
65                  70                  75                  80

Leu Ile Lys Gly Ser Thr Met His Phe Glu Tyr Ile Cys Asp Ser Thr
                85                  90                  95

Thr His Gln Leu Met Lys Leu Asn Phe Glu Leu Gly Ile Pro Val Ile
            100                 105                 110

Phe Gly Val Leu Thr Cys Leu Thr Asp Glu Gln Ala Glu Ala Arg Ala
        115                 120                 125

Gly Leu Ile Glu Gly Lys Met His Asn His Gly Glu Asp Trp Gly Ala
    130                 135                 140

Ala Ala Val Glu Met Ala Thr Lys Phe Asn
145                 150

<210> SEQ ID NO 15
<211> LENGTH: 164
<212> TYPE: PRT
<213> ORGANISM: Artificial Sequence
<220> FEATURE:
<223> OTHER INFORMATION: Synthetic

<400> SEQUENCE: 15

Met Ala Val Lys Gly Leu Gly Glu Val Asp Gln Lys Tyr Asp Gly Ser
1               5                   10                  15

Lys Leu Arg Ile Gly Ile Leu His Ala Arg Trp Asn Arg Lys Ile Ile
            20                  25                  30

Leu Ala Leu Val Ala Gly Ala Val Arg Leu Leu Glu Phe Gly Val
        35                  40                  45

Lys Ala Glu Asn Ile Ile Glu Thr Val Pro Gly Ser Phe Glu Leu
    50                  55                  60

Pro Tyr Gly Ser Lys Leu Phe Val Glu Lys Gln Lys Arg Leu Gly Lys
65                  70                  75                  80

Pro Leu Asp Ala Ile Pro Ile Gly Val Leu Ile Lys Gly Ser Thr
                85                  90                  95

Met His Phe Glu Tyr Ile Cys Asp Ser Thr His Gln Leu Met Lys
            100                 105                 110

Leu Asn Phe Glu Leu Gly Ile Pro Val Ile Phe Gly Val Leu Thr Cys
        115                 120                 125

Leu Thr Asp Glu Gln Ala Glu Ala Arg Ala Gly Leu Ile Glu Gly Lys
        130                 135                 140

Met His Asn His Gly Glu Asp Trp Gly Ala Ala Ala Val Glu Met Ala
145                 150                 155                 160

Thr Lys Phe Asn

<210> SEQ ID NO 16
<211> LENGTH: 175
<212> TYPE: PRT
<213> ORGANISM: Artificial Sequence
<220> FEATURE:
<223> OTHER INFORMATION: Synthetic

<400> SEQUENCE: 16

Met Gly Ala Asn Trp Tyr Leu Asp Asn Glu Ser Ser Arg Leu Ser Phe
1               5                   10                  15

Thr Ser Thr Lys Asn Ala Asp Ile Ala Glu Val His Arg Phe Leu Val
            20                  25                  30

Leu His Gly Lys Val Asp Pro Lys Gly Leu Ala Glu Val Glu Val Glu
        35                  40                  45

Thr Glu Ser Ile Ser Thr Gly Ile Pro Leu Arg Asp Met Leu Leu Arg
    50                  55                  60

Val Leu Val Phe Gln Val Ser Lys Phe Pro Val Ala Gln Ile Asn Ala
65                  70                  75                  80

Gln Leu Asp Met Arg Pro Ile Asn Asn Leu Ala Pro Gly Ala Gln Leu
                85                  90                  95

Glu Leu Arg Leu Pro Leu Thr Val Ser Leu Arg Gly Lys Ser His Ser
            100                 105                 110

Tyr Asn Ala Glu Leu Leu Ala Thr Arg Leu Asp Glu Arg Arg Phe Gln
        115                 120                 125

Val Val Thr Leu Glu Pro Leu Val Ile His Ala Gln Asp Phe Asp Met
    130                 135                 140

Val Arg Ala Phe Asn Ala Leu Arg Leu Val Ala Gly Leu Ser Ala Val
145                 150                 155                 160

Ser Leu Ser Val Pro Val Gly Ala Val Leu Ile Phe Thr Ala Arg
                165                 170                 175

<210> SEQ ID NO 17
<211> LENGTH: 208
<212> TYPE: PRT
<213> ORGANISM: Artificial Sequence
<220> FEATURE:
<223> OTHER INFORMATION: Synthetic

<400> SEQUENCE: 17

Met Thr Asp Tyr Ile Arg Asp Gly Ser Ala Ile Lys Ala Leu Ser Phe
1               5                   10                  15

Ala Ile Ile Leu Ala Glu Ala Asp Leu Arg His Ile Pro Gln Asp Leu
            20                  25                  30

Gln Arg Leu Ala Val Arg Val Ile His Ala Cys Gly Met Val Asp Val
        35                  40                  45

Ala Asn Asp Leu Ala Phe Ser Glu Gly Ala Gly Lys Ala Gly Arg Asn
    50                  55                  60

Ala Leu Leu Ala Gly Ala Pro Ile Leu Cys Asp Ala Arg Met Val Ala
65                  70                  75                  80

Glu Gly Ile Thr Arg Ser Arg Leu Pro Ala Asp Asn Arg Val Ile Tyr
                85                  90                  95

Thr Leu Ser Asp Pro Ser Val Pro Glu Leu Ala Lys Lys Ile Gly Asn
            100                 105                 110

Thr Arg Ser Ala Ala Ala Leu Asp Leu Trp Leu Pro His Ile Glu Gly
            115                 120                 125

Ser Ile Val Ala Ile Gly Asn Ala Pro Thr Ala Leu Phe Arg Leu Phe
    130                 135                 140

Glu Leu Leu Asp Ala Gly Ala Pro Lys Pro Ala Leu Ile Ile Gly Met
145                 150                 155                 160

Pro Val Gly Phe Val Gly Ala Ala Glu Ser Lys Asp Glu Leu Ala Ala
                165                 170                 175

Asn Ser Arg Gly Val Pro Tyr Val Ile Val Arg Gly Arg Gly Gly
            180                 185                 190

Ser Ala Met Thr Ala Ala Ala Val Asn Ala Leu Ala Ser Glu Arg Glu
            195                 200                 205

<210> SEQ ID NO 18
<211> LENGTH: 128
<212> TYPE: PRT
<213> ORGANISM: Artificial Sequence
<220> FEATURE:
<223> OTHER INFORMATION: Synthetic

<400> SEQUENCE: 18

Met Ile Thr Val Phe Gly Leu Lys Ser Lys Leu Ala Pro Arg Arg Glu
1               5                   10                  15

Lys Leu Ala Glu Val Ile Tyr Ser Ser Leu His Leu Gly Leu Asp Ile
            20                  25                  30

Pro Lys Gly Lys His Ala Ile Arg Phe Leu Cys Leu Glu Lys Glu Asp
        35                  40                  45

Phe Tyr Tyr Pro Phe Asp Arg Ser Asp Asp Tyr Thr Val Ile Glu Ile
    50                  55                  60

Asn Leu Met Ala Gly Arg Ser Glu Glu Thr Lys Met Leu Leu Ile Phe
65                  70                  75                  80

Leu Leu Phe Ile Ala Leu Glu Arg Lys Leu Gly Ile Arg Ala His Asp
                85                  90                  95

Val Glu Ile Thr Ile Lys Glu Gln Pro Ala His Cys Trp Gly Phe Arg
            100                 105                 110

Gly Arg Thr Gly Asp Ser Ala Arg Asp Leu Asp Tyr Asp Ile Tyr Val
        115                 120                 125

<210> SEQ ID NO 19
<211> LENGTH: 235
<212> TYPE: PRT
<213> ORGANISM: Artificial Sequence
<220> FEATURE:
<223> OTHER INFORMATION: Synthetic

<400> SEQUENCE: 19

Met Gly Ser Asp Leu Gln Lys Leu Gln Arg Phe Ser Thr Cys Asp Ile
1               5                   10                  15

Ser Asp Gly Leu Leu Asn Val Tyr Asn Ile Pro Thr Gly Gly Tyr Phe
            20                  25                  30

Pro Asn Leu Thr Ala Ile Ser Pro Gln Asn Ser Ser Ile Val Gly
        35                  40                  45

Thr Ala Tyr Thr Val Leu Phe Ala Pro Ile Asp Pro Arg Pro Ala
    50                  55                  60

Val Asn Tyr Ile Asp Ser Val Pro Pro Asn Ser Ile Leu Val Leu Ala

```
                65                  70                  75                  80
Leu Glu Pro His Leu Gln Ser Gln Phe His Pro Phe Ile Lys Ile Thr
                    85                  90                  95
Gln Ala Met Tyr Gly Gly Leu Met Ser Thr Arg Ala Gln Tyr Leu Lys
                100                 105                 110
Ser Asn Gly Thr Val Val Phe Gly Arg Ile Arg Asp Val Asp Glu His
                115                 120                 125
Arg Thr Leu Asn His Pro Val Phe Ala Tyr Gly Val Gly Ser Cys Ala
130                 135                 140
Pro Lys Ala Val Val Lys Ala Val Gly Thr Asn Val Gln Leu Lys Ile
145                 150                 155                 160
Leu Thr Ser Asp Gly Val Thr Gln Thr Ile Cys Pro Gly Asp Tyr Ile
                165                 170                 175
Ala Gly Asp Asn Asn Gly Ile Val Arg Ile Pro Val Gln Glu Thr Asp
                180                 185                 190
Ile Ser Lys Leu Val Thr Tyr Ile Glu Lys Ser Ile Glu Val Asp Arg
                195                 200                 205
Leu Val Ser Glu Ala Ile Lys Asn Gly Leu Pro Ala Lys Ala Ala Gln
            210                 215                 220
Thr Ala Arg Arg Met Val Leu Lys Asp Tyr Ile
225                 230                 235

<210> SEQ ID NO 20
<211> LENGTH: 162
<212> TYPE: PRT
<213> ORGANISM: Artificial Sequence
<220> FEATURE:
<223> OTHER INFORMATION: Synthetic

<400> SEQUENCE: 20

Met Ser Gly Met Arg Val Tyr Leu Gly Ala Asp His Ala Gly Tyr Glu
1               5                   10                  15
Leu Lys Gln Ala Ile Ile Ala Phe Leu Lys Met Thr Gly His Glu Pro
                20                  25                  30
Ile Asp Cys Gly Ala Leu Arg Tyr Asp Ala Asp Asp Tyr Pro Ala
            35                  40                  45
Phe Cys Ile Ala Ala Ala Thr Arg Thr Val Ala Asp Pro Gly Ser Leu
    50                  55                  60
Gly Ile Val Leu Gly Gly Ser Gly Asn Gly Glu Gln Ile Ala Ala Asn
65                  70                  75                  80
Lys Val Pro Gly Ala Arg Cys Ala Leu Ala Trp Ser Val Gln Thr Ala
                85                  90                  95
Ala Leu Ala Arg Glu His Asn Asn Ala Gln Leu Ile Gly Ile Gly Gly
                100                 105                 110
Arg Met His Thr Leu Glu Glu Ala Leu Arg Ile Val Lys Ala Phe Val
                115                 120                 125
Thr Thr Pro Trp Ser Lys Ala Gln Arg His Arg Arg Ile Asp Ile
            130                 135                 140
Leu Ala Glu Tyr Glu Arg Thr His Glu Ala Pro Pro Val Pro Gly Ala
145                 150                 155                 160
Pro Ala

<210> SEQ ID NO 21
<211> LENGTH: 157
<212> TYPE: PRT
<213> ORGANISM: Artificial Sequence
```

<220> FEATURE:
<223> OTHER INFORMATION: Synthetic

<400> SEQUENCE: 21

Met Gly Asp Asp Ala Arg Ile Ala Ala Ile Gly Asp Val Asp Glu Leu
1               5                   10                  15

Asn Ser Gln Ile Gly Val Leu Leu Ala Glu Pro Leu Pro Asp Asp Val
            20                  25                  30

Arg Ala Ala Leu Ser Ala Ile Gln His Asp Leu Phe Asp Leu Gly Gly
        35                  40                  45

Glu Leu Cys Ile Pro Gly His Ala Ala Ile Thr Glu Asp His Leu Leu
    50                  55                  60

Arg Leu Ala Leu Trp Leu Val His Tyr Asn Gly Gln Leu Pro Pro Leu
65                  70                  75                  80

Glu Glu Phe Ile Leu Pro Gly Gly Ala Arg Gly Ala Ala Leu Ala His
                85                  90                  95

Val Cys Arg Thr Val Cys Arg Arg Ala Glu Arg Ser Ile Lys Ala Leu
            100                 105                 110

Gly Ala Ser Glu Pro Leu Asn Ile Ala Pro Ala Ala Tyr Val Asn Leu
        115                 120                 125

Leu Ser Asp Leu Leu Phe Val Leu Ala Arg Val Leu Asn Arg Ala Ala
    130                 135                 140

Gly Gly Ala Asp Val Leu Trp Asp Arg Thr Arg Ala His
145                 150                 155

<210> SEQ ID NO 22
<211> LENGTH: 157
<212> TYPE: PRT
<213> ORGANISM: Artificial Sequence
<220> FEATURE:
<223> OTHER INFORMATION: Synthetic

<400> SEQUENCE: 22

Met Ile Leu Ser Ala Glu Gln Ser Phe Thr Leu Arg His Pro His Gly
1               5                   10                  15

Gln Ala Ala Ala Leu Ala Phe Val Arg Glu Pro Ala Ala Ala Leu Ala
            20                  25                  30

Gly Val Gln Arg Leu Arg Gly Leu Asp Ser Asp Gly Glu Gln Val Trp
        35                  40                  45

Gly Glu Leu Leu Val Arg Val Pro Leu Leu Gly Glu Val Asp Leu Pro
    50                  55                  60

Phe Arg Ser Glu Ile Val Arg Thr Pro Gln Gly Ala Glu Leu Arg Pro
65                  70                  75                  80

Leu Thr Leu Thr Gly Glu Arg Ala Trp Val Ala Val Ser Gly Gln Ala
                85                  90                  95

Thr Ala Ala Glu Gly Gly Glu Met Ala Phe Ala Phe Gln Phe Gln Ala
            100                 105                 110

His Leu Ala Thr Pro Glu Ala Glu Gly Glu Gly Ala Ala Phe Glu
        115                 120                 125

Val Met Val Gln Ala Ala Ala Gly Val Thr Leu Leu Leu Val Ala Met
    130                 135                 140

Ala Leu Pro Gln Gly Leu Ala Ala Gly Leu Pro Pro Ala
145                 150                 155

<210> SEQ ID NO 23
<211> LENGTH: 156
<212> TYPE: PRT

<213> ORGANISM: Artificial Sequence
<220> FEATURE:
<223> OTHER INFORMATION: Synthetic

<400> SEQUENCE: 23

Met Thr Lys Lys Val Gly Ile Val Asp Thr Thr Phe Ala Arg Val Asp
1               5                   10                  15

Met Ala Ser Ala Ala Ile Leu Thr Leu Lys Met Glu Ser Pro Asn Ile
            20                  25                  30

Lys Ile Ile Arg Lys Thr Val Pro Gly Ile Lys Asp Leu Pro Val Ala
        35                  40                  45

Cys Lys Lys Leu Leu Glu Glu Glu Gly Cys Asp Ile Val Met Ala Leu
    50                  55                  60

Gly Met Pro Gly Lys Lys Glu Lys Asp Lys Val Cys Ala His Glu Ala
65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
            100                 105                 110

Ile Leu Ala Ala Arg Arg Ala Ile Glu His Ala Leu Asn Val Tyr Tyr
        115                 120                 125

Leu Leu Phe Lys Pro Glu Tyr Leu Thr Arg Met Ala Gly Lys Gly Leu
    130                 135                 140

Arg Gln Gly Phe Glu Asp Ala Gly Pro Ala Arg Glu
145                 150                 155

<210> SEQ ID NO 24
<211> LENGTH: 209
<212> TYPE: PRT
<213> ORGANISM: Artificial Sequence
<220> FEATURE:
<223> OTHER INFORMATION: Synthetic

<400> SEQUENCE: 24

Met Asp Asp Ile Asn Asn Gln Leu Lys Arg Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
    50                  55                  60

Ile Gly Ala Gly Thr Ile Leu Asn Gly Val Gln Ala Leu Ala Ala Lys
65                  70                  75                  80

Glu Ala Gly Ala Asp Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Gln Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Asp Asn Ile Asp Asn Tyr Leu Ala Ile Pro Gln Val Leu Ala
                165                 170                 175

```
Cys Gly Gly Thr Trp Met Val Asp Lys Lys Leu Val Arg Asn Gly Glu
            180                 185                 190
Trp Asp Glu Ile Ala Arg Leu Thr Arg Glu Ile Val Glu Gln Val Asn
        195                 200                 205
Pro
```

<210> SEQ ID NO 25
<211> LENGTH: 114
<212> TYPE: PRT
<213> ORGANISM: Artificial Sequence
<220> FEATURE:
<223> OTHER INFORMATION: Synthetic

<400> SEQUENCE: 25

```
Met Pro Ile Phe Thr Leu Asn Thr Asn Ile Lys Ala Asp Asp Val Pro
1               5                   10                  15
Ser Asp Phe Leu Ser Leu Thr Ser Arg Leu Val Gly Leu Ile Leu Ser
            20                  25                  30
Lys Pro Gly Ser Tyr Val Ala Val His Ile Asn Thr Asp Gln Gln Leu
        35                  40                  45
Ser Phe Gly Gly Ser Thr Asn Pro Ala Ala Phe Gly Thr Leu Met Ser
    50                  55                  60
Ile Gly Gly Ile Glu Pro Asp Lys Asn Arg Asp His Ser Ala Val Leu
65                  70                  75                  80
Phe Asp His Leu Asn Ala Met Leu Gly Ile Pro Lys Asn Arg Met Tyr
                85                  90                  95
Ile His Phe Val Asn Leu Asn Gly Asp Asp Val Gly Trp Asn Gly Thr
            100                 105                 110
Thr Phe
```

<210> SEQ ID NO 26
<211> LENGTH: 114
<212> TYPE: PRT
<213> ORGANISM: Artificial Sequence
<220> FEATURE:
<223> OTHER INFORMATION: Synthetic

<400> SEQUENCE: 26

```
Met Pro Ile Phe Thr Leu Asn Thr Asn Ile Lys Ala Asp Asp Val Pro
1               5                   10                  15
Ser Asp Phe Leu Ser Leu Thr Ser Arg Leu Val Gly Leu Ile Leu Ser
            20                  25                  30
Glu Pro Gly Ser Tyr Val Ala Val His Ile Asn Thr Asp Gln Gln Leu
        35                  40                  45
Ser Phe Gly Gly Ser Thr Asn Pro Ala Ala Phe Gly Thr Leu Met Ser
    50                  55                  60
Ile Gly Gly Ile Glu Pro Asp Lys Asn Glu Asp His Ser Ala Val Leu
65                  70                  75                  80
Phe Asp His Leu Asn Ala Met Leu Gly Ile Pro Lys Asn Arg Met Tyr
                85                  90                  95
Ile His Phe Val Asp Leu Asp Gly Asp Asp Val Gly Trp Asn Gly Thr
            100                 105                 110
Thr Phe
```

<210> SEQ ID NO 27
<211> LENGTH: 157
<212> TYPE: PRT
<213> ORGANISM: Artificial Sequence
<220> FEATURE:
<223> OTHER INFORMATION: Synthetic

<400> SEQUENCE: 27

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asn Gly Gly Ile Tyr Arg His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Arg Tyr Arg Asp Ser Asp Glu His His Arg
        115                 120                 125

Phe Phe Ala Ala His Phe Ala Val Lys Gly Val Glu Ala Ala Arg Ala
    130                 135                 140

Cys Ile Glu Ile Leu Asn Ala Arg Glu Lys Ile Ala Ala
145                 150                 155

<210> SEQ ID NO 28
<211> LENGTH: 157
<212> TYPE: PRT
<213> ORGANISM: Artificial Sequence
<220> FEATURE:
<223> OTHER INFORMATION: Synthetic

<400> SEQUENCE: 28

Met Asn Gln His Ser His Lys Asp His Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Asp Gly Gly Ile Tyr Asp His Glu Phe Val Ala Ser Ala Val Ile
                85                  90                  95

Asp Gly Met Met Asn Val Gln Leu Asp Thr Gly Val Pro Val Leu Ser
            100                 105                 110

Ala Val Leu Thr Pro His Glu Tyr Glu Asp Ser Asp Glu Asp His Glu
        115                 120                 125

Phe Phe Ala Ala His Phe Ala Val Lys Gly Val Glu Ala Ala Arg Ala
    130                 135                 140

Cys Ile Glu Ile Leu Asn Ala Arg Glu Lys Ile Ala Ala
145                 150                 155

<210> SEQ ID NO 29
<211> LENGTH: 205
<212> TYPE: PRT

<213> ORGANISM: Artificial Sequence
<220> FEATURE:
<223> OTHER INFORMATION: Synthetic

<400> SEQUENCE: 29

```
Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Asp Ala Leu Val Lys Gly Asp Pro Asp Glu Val Arg Glu Lys
            180                 185                 190

Ala Lys Lys Phe Val Glu Lys Ile Arg Gly Cys Thr Glu
        195                 200                 205
```

<210> SEQ ID NO 30
<211> LENGTH: 205
<212> TYPE: PRT
<213> ORGANISM: Artificial Sequence
<220> FEATURE:
<223> OTHER INFORMATION: Synthetic

<400> SEQUENCE: 30

```
Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125
```

Lys Leu Phe Pro Gly Glu Val Val Gly Pro Glu Phe Val Glu Ala Met
    130                 135                 140

Lys Gly Pro Phe Pro Asn Val Lys Phe Val Pro Thr Gly Gly Val Asp
145                 150                 155                 160

Leu Asp Asp Val Cys Glu Trp Phe Asp Ala Gly Val Leu Ala Val Gly
                165                 170                 175

Val Gly Asp Ala Leu Val Glu Gly Asp Pro Asp Val Arg Glu Asp
            180                 185                 190

Ala Lys Glu Phe Val Glu Glu Ile Arg Gly Cys Thr Glu
        195                 200                 205

<210> SEQ ID NO 31
<211> LENGTH: 205
<212> TYPE: PRT
<213> ORGANISM: Artificial Sequence
<220> FEATURE:
<223> OTHER INFORMATION: Synthetic

<400> SEQUENCE: 31

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
            20                  25                  30

Ala Gly Gly Val His Leu Ile Glu Ile Thr Phe Thr Val Pro Asp Ala
        35                  40                  45

Asp Thr Val Ile Lys Ala Leu Ser Val Leu Lys Glu Lys Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Asp Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Lys Trp Phe Lys Ala Gly Val Leu Ala Val Gly
                165                 170                 175

Val Gly Lys Ala Leu Val Lys Gly Lys Pro Asp Glu Val Arg Glu Lys
            180                 185                 190

Ala Lys Lys Phe Val Lys Lys Ile Arg Gly Cys Thr Glu
        195                 200                 205

<210> SEQ ID NO 32
<211> LENGTH: 157
<212> TYPE: PRT
<213> ORGANISM: Artificial Sequence
<220> FEATURE:
<223> OTHER INFORMATION: Synthetic

<400> SEQUENCE: 32

Met Asn Gln His Ser His Lys Asp His Glu Thr Val Arg Ile Ala Val
1               5                   10                  15

Val Arg Ala Arg Trp His Ala Glu Ile Val Asp Ala Cys Val Ser Ala
            20                  25                  30

```
Phe Glu Ala Ala Met Arg Asp Ile Gly Gly Asp Arg Phe Ala Val Asp
            35                  40                  45

Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asn Gly Gly Ile Tyr Arg His Glu Phe Val Ala Ser Ala Val Ile
                 85                  90                  95

Asp Gly Met Met Asn Val Gln Leu Asp Thr Gly Val Pro Val Leu Ser
                100                 105                 110

Ala Val Leu Thr Pro His Arg Tyr Arg Asp Ser Asp Ala His Thr Leu
             115                 120                 125

Leu Phe Leu Ala Leu Phe Ala Val Lys Gly Met Glu Ala Ala Arg Ala
 130                 135                 140

Cys Val Glu Ile Leu Ala Ala Arg Glu Lys Ile Ala Ala
145                 150                 155

<210> SEQ ID NO 33
<211> LENGTH: 157
<212> TYPE: PRT
<213> ORGANISM: Artificial Sequence
<220> FEATURE:
<223> OTHER INFORMATION: Synthetic

<400> SEQUENCE: 33

Met Asn Gln His Ser His Lys Asp His Glu Thr Val Arg Ile Ala Val
  1               5                  10                  15

Val Arg Ala Arg Trp His Ala Glu Ile Val Asp Ala Cys Val Ser Ala
             20                  25                  30

Phe Glu Ala Ala Met Arg Asp Ile Gly Gly Asp Arg Phe Ala Val Asp
            35                  40                  45

Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asp Gly Gly Ile Tyr Asp His Glu Phe Val Ala Ser Ala Val Ile
                 85                  90                  95

Asp Gly Met Met Asn Val Gln Leu Asp Thr Gly Val Pro Val Leu Ser
                100                 105                 110

Ala Val Leu Thr Pro His Glu Tyr Glu Asp Ser Asp Ala Asp Thr Leu
             115                 120                 125

Leu Phe Leu Ala Leu Phe Ala Val Lys Gly Met Glu Ala Ala Arg Ala
 130                 135                 140

Cys Val Glu Ile Leu Ala Ala Arg Glu Lys Ile Ala Ala
145                 150                 155

<210> SEQ ID NO 34
<211> LENGTH: 157
<212> TYPE: PRT
<213> ORGANISM: Artificial Sequence
<220> FEATURE:
<223> OTHER INFORMATION: Synthetic

<400> SEQUENCE: 34

Met Asn Gln His Ser His Lys Asp His Glu Thr Val Arg Ile Ala Val
  1               5                  10                  15

Val Arg Ala Arg Trp His Ala Glu Ile Val Asp Ala Cys Val Ser Ala
```

```
                   20                  25                  30
Phe Glu Ala Ala Met Arg Asp Ile Gly Gly Asp Arg Phe Ala Val Asp
                35                  40                  45

Val Phe Asp Val Pro Gly Ala Tyr Glu Ile Pro Leu His Ala Arg Thr
 50                  55                  60

Leu Ala Glu Thr Gly Arg Tyr Gly Ala Val Leu Gly Thr Ala Phe Val
 65                  70                  75                  80

Val Asn Gly Gly Ile Tyr Arg His Glu Phe Val Ala Ser Ala Val Ile
                85                  90                  95

Asn Gly Met Met Asn Val Gln Leu Asn Thr Gly Val Pro Val Leu Ser
                100                 105                 110

Ala Val Leu Thr Pro His Asn Tyr Asp Lys Ser Lys Ala His Thr Leu
            115                 120                 125

Leu Phe Leu Ala Leu Phe Ala Val Lys Gly Met Glu Ala Ala Arg Ala
        130                 135                 140

Cys Val Glu Ile Leu Ala Ala Arg Glu Lys Ile Ala Ala
145                 150                 155

<210> SEQ ID NO 35
<211> LENGTH: 156
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (70)..(70)
<223> OTHER INFORMATION: Xaa is A or K

<400> SEQUENCE: 35

Met Thr Lys Lys Val Gly Ile Val Asp Thr Thr Phe Ala Arg Val Asp
 1               5                  10                  15

Met Ala Ser Ala Ala Ile Leu Thr Leu Lys Met Glu Ser Pro Asn Ile
                20                  25                  30

Lys Ile Ile Arg Lys Thr Val Pro Gly Ile Lys Asp Leu Pro Val Ala
            35                  40                  45

Cys Lys Lys Leu Leu Glu Glu Gly Cys Asp Ile Val Met Ala Leu
 50                  55                  60

Gly Met Pro Gly Lys Xaa Glu Lys Asp Lys Val Cys Ala His Glu Ala
 65                  70                  75                  80

Ser Leu Gly Leu Met Leu Ala Gln Leu Met Thr Asn Lys His Ile Ile
                85                  90                  95

Glu Val Phe Val His Glu Asp Glu Ala Lys Asp Ala Glu Leu Lys
                100                 105                 110

Ile Leu Ala Ala Arg Arg Ala Ile Glu His Ala Leu Asn Val Tyr Tyr
            115                 120                 125

Leu Leu Phe Lys Pro Glu Tyr Leu Thr Arg Met Ala Gly Lys Gly Leu
        130                 135                 140

Arg Gln Gly Phe Glu Asp Ala Gly Pro Ala Arg Glu
145                 150                 155

<210> SEQ ID NO 36
<211> LENGTH: 209
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (2)..(2)
<223> OTHER INFORMATION: Xaa is S or D
<220> FEATURE:
<221> NAME/KEY: MISC_FEATURE
<222> LOCATION: (3)..(3)
<223> OTHER INFORMATION: Xaa is T or D
<220> FEATURE:
<221> NAME/KEY: MISC_FEATURE
<222> LOCATION: (10)..(10)
<223> OTHER INFORMATION: Xaa is A or R
<220> FEATURE:
<221> NAME/KEY: MISC_FEATURE
<222> LOCATION: (85)..(85)
<223> OTHER INFORMATION: Xaa is T or D
<220> FEATURE:
<221> NAME/KEY: MISC_FEATURE
<222> LOCATION: (119)..(119)
<223> OTHER INFORMATION: Xaa is A or Q
<220> FEATURE:
<221> NAME/KEY: MISC_FEATURE
<222> LOCATION: (163)..(163)
<223> OTHER INFORMATION: Xaa is S or D
<220> FEATURE:
<221> NAME/KEY: MISC_FEATURE
<222> LOCATION: (189)..(189)
<223> OTHER INFORMATION: Xaa is T or R

<400> SEQUENCE: 36

Met Xaa Xaa Ile Asn Asn Gln Leu Lys Xaa Leu Lys Val Ile Pro Val
1               5                   10                  15

Ile Ala Ile Asp Asn Ala Glu Asp Ile Ile Pro Leu Gly Lys Val Leu
            20                  25                  30

Ala Glu Asn Gly Leu Pro Ala Ala Glu Ile Thr Phe Arg Ser Ser Ala
        35                  40                  45

Ala Val Lys Ala Ile Met Leu Leu Arg Ser Ala Gln Pro Glu Met Leu
50                  55                  60

Ile Gly Ala Gly Thr Ile Leu Asn Gly Val Gln Ala Leu Ala Ala Lys
65                  70                  75                  80

Glu Ala Gly Ala Xaa Phe Val Val Ser Pro Gly Phe Asn Pro Asn Thr
                85                  90                  95

Val Arg Ala Cys Gln Ile Ile Gly Ile Asp Ile Val Pro Gly Val Asn
            100                 105                 110

Asn Pro Ser Thr Val Glu Xaa Ala Leu Glu Met Gly Leu Thr Thr Leu
        115                 120                 125

Lys Phe Phe Pro Ala Glu Ala Ser Gly Gly Ile Ser Met Val Lys Ser
    130                 135                 140

Leu Val Gly Pro Tyr Gly Asp Ile Arg Leu Met Pro Thr Gly Gly Ile
145                 150                 155                 160

Thr Pro Xaa Asn Ile Asp Asn Tyr Leu Ala Ile Pro Gln Val Leu Ala
                165                 170                 175

Cys Gly Gly Thr Trp Met Val Asp Lys Lys Leu Val Xaa Asn Gly Glu
            180                 185                 190

Trp Asp Glu Ile Ala Arg Leu Thr Arg Glu Ile Val Glu Gln Val Asn
        195                 200                 205

Pro

<210> SEQ ID NO 37
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (13)..(13)
<223> OTHER INFORMATION: Xaa is T or D
<220> FEATURE:
<221> NAME/KEY: MISC_FEATURE
<222> LOCATION: (33)..(33)
<223> OTHER INFORMATION: Xaa is K or E
<220> FEATURE:
<221> NAME/KEY: MISC_FEATURE
<222> LOCATION: (71)..(71)
<223> OTHER INFORMATION: Xaa is S or D
<220> FEATURE:
<221> NAME/KEY: MISC_FEATURE
<222> LOCATION: (74)..(74)
<223> OTHER INFORMATION: Xaa is R or E
<220> FEATURE:
<221> NAME/KEY: MISC_FEATURE
<222> LOCATION: (101)..(101)
<223> OTHER INFORMATION: Xaa is N or D
<220> FEATURE:
<221> NAME/KEY: MISC_FEATURE
<222> LOCATION: (103)..(103)
<223> OTHER INFORMATION: Xaa is N or D

<400> SEQUENCE: 37

Met Pro Ile Phe Thr Leu Asn Thr Asn Ile Lys Ala Xaa Asp Val Pro
1               5                   10                  15

Ser Asp Phe Leu Ser Leu Thr Ser Arg Leu Val Gly Leu Ile Leu Ser
            20                  25                  30

Xaa Pro Gly Ser Tyr Val Ala Val His Ile Asn Thr Asp Gln Gln Leu
        35                  40                  45

Ser Phe Gly Gly Ser Thr Asn Pro Ala Ala Phe Gly Thr Leu Met Ser
    50                  55                  60

Ile Gly Gly Ile Glu Pro Xaa Lys Asn Xaa Asp His Ser Ala Val Leu
65                  70                  75                  80

Phe Asp His Leu Asn Ala Met Leu Gly Ile Pro Lys Asn Arg Met Tyr
                85                  90                  95

Ile His Phe Val Xaa Leu Xaa Gly Asp Asp Val Gly Trp Asn Gly Thr
            100                 105                 110

Thr Phe

<210> SEQ ID NO 38
<211> LENGTH: 157
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (105)..(105)
<223> OTHER INFORMATION: Xaa is S or D
<220> FEATURE:
<221> NAME/KEY: MISC_FEATURE
<222> LOCATION: (119)..(119)
<223> OTHER INFORMATION: Xaa is R or E
<220> FEATURE:
<221> NAME/KEY: MISC_FEATURE
<222> LOCATION: (121)..(121)
<223> OTHER INFORMATION: Xaa is R or E
```

```
<220> FEATURE:
<221> NAME/KEY: MISC_FEATURE
<222> LOCATION: (124)..(124)
<223> OTHER INFORMATION: Xaa is A or D
<220> FEATURE:
<221> NAME/KEY: MISC_FEATURE
<222> LOCATION: (126)..(126)
<223> OTHER INFORMATION: Xaa is H or D
<220> FEATURE:
<221> NAME/KEY: MISC_FEATURE
<222> LOCATION: (128)..(128)
<223> OTHER INFORMATION: Xaa is R or E
<220> FEATURE:
<221> NAME/KEY: MISC_FEATURE
<222> LOCATION: (150)..(150)
<223> OTHER INFORMATION: Xaa is A or N

<400> SEQUENCE: 38

Met Asn Gln His Ser His Lys Asp Xaa Glu Thr Val Arg Ile Ala Val
1               5                   10                  15

Val Arg Ala Arg Trp His Ala Asp Ile Val Asp Ala Cys Val Glu Ala
            20                  25                  30

Phe Glu Ile Ala Met Ala Ala Ile Gly Gly Asp Arg Phe Ala Val Asp
        35                  40                  45

Val Phe Asp Val Pro Gly Ala Tyr Glu Ile Pro Leu His Ala Arg Thr
    50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
            85                  90                  95

Asp Gly Met Met Asn Val Gln Leu Xaa Thr Gly Val Pro Val Leu Ser
            100                 105                 110

Ala Val Leu Thr Pro His Xaa Tyr Xaa Asp Ser Xaa Glu Xaa His Xaa
            115                 120                 125

Phe Phe Ala Ala His Phe Ala Val Lys Gly Val Glu Ala Ala Arg Ala
        130                 135                 140

Cys Ile Glu Ile Leu Xaa Ala Arg Glu Lys Ile Ala Ala
145                 150                 155

<210> SEQ ID NO 39
<211> LENGTH: 205
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (126)..(126)
<223> OTHER INFORMATION: Xaa is T or D
<220> FEATURE:
<221> NAME/KEY: MISC_FEATURE
<222> LOCATION: (139)..(139)
<223> OTHER INFORMATION: Xaa is Q or E
<220> FEATURE:
<221> NAME/KEY: MISC_FEATURE
<222> LOCATION: (142)..(142)
<223> OTHER INFORMATION: Xaa is K or E
<220> FEATURE:
<221> NAME/KEY: MISC_FEATURE
<222> LOCATION: (160)..(160)
<223> OTHER INFORMATION: Xaa is N or D
<220> FEATURE:
<221> NAME/KEY: MISC_FEATURE
<222> LOCATION: (163)..(163)
<223> OTHER INFORMATION: Xaa is N or D
<220> FEATURE:
<221> NAME/KEY: MISC_FEATURE
<222> LOCATION: (166)..(166)
```

```
<223> OTHER INFORMATION: Xaa is E or K
<220> FEATURE:
<221> NAME/KEY: MISC_FEATURE
<222> LOCATION: (169)..(169)
<223> OTHER INFORMATION: Xaa is D or K
<220> FEATURE:
<221> NAME/KEY: MISC_FEATURE
<222> LOCATION: (179)..(179)
<223> OTHER INFORMATION: Xaa is S, D or K
<220> FEATURE:
<221> NAME/KEY: MISC_FEATURE
<222> LOCATION: (183)..(183)
<223> OTHER INFORMATION: Xaa is K or E
<220> FEATURE:
<221> NAME/KEY: MISC_FEATURE
<222> LOCATION: (185)..(185)
<223> OTHER INFORMATION: Xaa is T, D, or K
<220> FEATURE:
<221> NAME/KEY: MISC_FEATURE
<222> LOCATION: (192)..(192)
<223> OTHER INFORMATION: Xaa is D or K
<220> FEATURE:
<221> NAME/KEY: MISC_FEATURE
<222> LOCATION: (195)..(195)
<223> OTHER INFORMATION: Xaa is A, E, or K
<220> FEATURE:
<221> NAME/KEY: MISC_FEATURE
<222> LOCATION: (198)..(198)
<223> OTHER INFORMATION: Xaa is E or K
<220> FEATURE:
<221> NAME/KEY: MISC_FEATURE
<222> LOCATION: (199)..(199)
<223> OTHER INFORMATION: Xaa is E or K

<400> SEQUENCE: 39

Met Lys Met Glu Glu Leu Phe Lys Lys His Lys Ile Val Ala Val Leu
1               5                   10                  15

Arg Ala Asn Ser Val Glu Glu Ala Ile Glu Lys Ala Val Ala Val Phe
                20                  25                  30

Ala Gly Gly Val His Leu Ile Glu Ile Thr Phe Thr Val Pro Asp Ala
            35                  40                  45

Asp Thr Val Ile Lys Ala Leu Ser Val Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Xaa Ile Leu
        115                 120                 125

Lys Leu Phe Pro Gly Glu Val Val Gly Pro Xaa Phe Val Xaa Ala Met
130                 135                 140

Lys Gly Pro Phe Pro Asn Val Lys Phe Val Pro Thr Gly Gly Val Xaa
145                 150                 155                 160

Leu Asp Xaa Val Cys Xaa Trp Phe Xaa Ala Gly Val Leu Ala Val Gly
                165                 170                 175

Val Gly Xaa Ala Leu Val Xaa Gly Xaa Pro Asp Glu Val Arg Glu Xaa
            180                 185                 190

Ala Lys Xaa Phe Val Xaa Xaa Ile Arg Gly Cys Thr Glu
        195                 200                 205

<210> SEQ ID NO 40
<211> LENGTH: 157
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa is Y or H
<220> FEATURE:
<221> NAME/KEY: MISC_FEATURE
<222> LOCATION: (38)..(38)
<223> OTHER INFORMATION: Xaa is A or R
<220> FEATURE:
<221> NAME/KEY: MISC_FEATURE
<222> LOCATION: (82)..(82)
<223> OTHER INFORMATION: Xaa is N or D
<220> FEATURE:
<221> NAME/KEY: MISC_FEATURE
<222> LOCATION: (87)..(87)
<223> OTHER INFORMATION: Xaa is R or D
<220> FEATURE:
<221> NAME/KEY: MISC_FEATURE
<222> LOCATION: (97)..(97)
<223> OTHER INFORMATION: Xaa is N or D
<220> FEATURE:
<221> NAME/KEY: MISC_FEATURE
<222> LOCATION: (105)..(105)
<223> OTHER INFORMATION: Xaa is S, N, or D
<220> FEATURE:
<221> NAME/KEY: MISC_FEATURE
<222> LOCATION: (119)..(119)
<223> OTHER INFORMATION: Xaa is R, E, or N
<220> FEATURE:
<221> NAME/KEY: MISC_FEATURE
<222> LOCATION: (121)..(121)
<223> OTHER INFORMATION: Xaa is R, E, or D
<220> FEATURE:
<221> NAME/KEY: MISC_FEATURE
<222> LOCATION: (122)..(122)
<223> OTHER INFORMATION: Xaa is K or D
<220> FEATURE:
<221> NAME/KEY: MISC_FEATURE
<222> LOCATION: (124)..(124)
<223> OTHER INFORMATION: Xaa is K or D
<220> FEATURE:
<221> NAME/KEY: MISC_FEATURE
<222> LOCATION: (126)..(126)
<223> OTHER INFORMATION: Xaa is H or D

<400> SEQUENCE: 40

Met Asn Gln His Ser His Lys Asp Xaa Glu Thr Val Arg Ile Ala Val
1               5                   10                  15

Val Arg Ala Arg Trp His Ala Glu Ile Val Asp Ala Cys Val Ser Ala
            20                  25                  30

Phe Glu Ala Ala Met Xaa Asp Ile Gly Gly Asp Arg Phe Ala Val Asp
        35                  40                  45

Val Phe Asp Val Pro Gly Ala Tyr Glu Ile Pro Leu His Ala Arg Thr
50                  55                  60

Leu Ala Glu Thr Gly Arg Tyr Gly Ala Val Leu Gly Thr Ala Phe Val
65                  70                  75                  80

Val Xaa Gly Gly Ile Tyr Xaa His Glu Phe Val Ala Ser Ala Val Ile
                85                  90                  95

Xaa Gly Met Met Asn Val Gln Leu Xaa Thr Gly Val Pro Val Leu Ser
            100                 105                 110

Ala Val Leu Thr Pro His Xaa Tyr Xaa Xaa Ser Xaa Ala Xaa Thr Leu
        115                 120                 125

Leu Phe Leu Ala Leu Phe Ala Val Lys Gly Met Glu Ala Ala Arg Ala
    130                 135                 140

Cys Val Glu Ile Leu Ala Ala Arg Glu Lys Ile Ala Ala
145                 150                 155
```

<210> SEQ ID NO 41
<211> LENGTH: 142
<212> TYPE: DNA
<213> ORGANISM: Artificial Sequence
<220> FEATURE:
<223> OTHER INFORMATION: Synthetic

<400> SEQUENCE: 41

```
taatgcttaa gtcgaacaga aagtaatcgt attgtacacg gccgcataat cgaaattaat      60
acgactcact ataggggaat tgtgagcgga taacaattcc ccatcttagt atattagtta     120
agtataagaa ggagatatac tt                                              142
```

<210> SEQ ID NO 42
<211> LENGTH: 18
<212> TYPE: DNA
<213> ORGANISM: Artificial Sequence
<220> FEATURE:
<223> OTHER INFORMATION: Synthetic

<400> SEQUENCE: 42

```
taaagaagga gatatcat                                                    18
```

<210> SEQ ID NO 43
<211> LENGTH: 17
<212> TYPE: DNA
<213> ORGANISM: Artificial Sequence
<220> FEATURE:
<223> OTHER INFORMATION: Synthetic

<400> SEQUENCE: 43

```
tgagaaggag atatcat                                                     17
```